(12) United States Patent
Robinson

(10) Patent No.: US 8,399,404 B2
(45) Date of Patent: Mar. 19, 2013

(54) METHODS AND USES FOR INHIBITING PLATELET COAGULATION

(75) Inventor: Lisa Annette Robinson, Toronto (CA)

(73) Assignee: The Hospital for Sick Children, Toronto, Ontario (CA)

( * ) Notice: Subject to any disclaimer, the term of this patent is extended or adjusted under 35 U.S.C. 154(b) by 0 days.

(21) Appl. No.: 13/100,678

(22) Filed: May 4, 2011

(65) Prior Publication Data

US 2011/0305732 A1     Dec. 15, 2011

Related U.S. Application Data

(60) Provisional application No. 61/397,666, filed on Jun. 15, 2010.

(51) Int. Cl.
*A61K 38/00*     (2006.01)
(52) U.S. Cl. ........................................................ 514/1.1
(58) Field of Classification Search ........................ None
See application file for complete search history.

(56) References Cited

U.S. PATENT DOCUMENTS

| | | |
|---|---|---|
| 2009/0028831 A1 | 1/2009 | Van Zant et al. |
| 2011/0034389 A1 | 2/2011 | Li et al. |

FOREIGN PATENT DOCUMENTS

| | | |
|---|---|---|
| WO | 0055195 | 9/2000 |
| WO | 2004003163 | 1/2004 |
| WO | 2008073441 | 6/2008 |
| WO | 2009129408 | 10/2009 |
| WO | 2010068917 | 6/2010 |

OTHER PUBLICATIONS

Chaturvedi, S., "Modulation of Acute Kidney Injury by Slit2", The Hospital for Sick Children, Institute of Medical Sciences, May 19, 2010, Presentation, Renal Research Rounds.
Patel, S., "Slit2/Robo-1: Novel modulators of vascular injury?", The Hospital for Sick Children, Institute of Medical Sciences, May 20, 2010, Presentation, Cell Bio Retreat.
Patel, S., et al., "Slit2/Robo-1: Novel modulators of platelet functions and atherothrombosis?", The Hospital for Sick Children, Institute of Medical Sciences, May 5, 2010, Poster Presentation.
Tole, S., et al., "The axonal repellent, Slit2, inhibits directional migration of circulating neutrophils", Journal of Leukocyte Biology, Dec. 2009, pp. 1-13, vol. 86.

*Primary Examiner* — Nashaat Nashed
(74) *Attorney, Agent, or Firm* — Bereskin & Parr LLP/S.E.N.C.R.L., s.r.l.; Melanie Szweras

(57) ABSTRACT

The present disclosure provides methods and uses of Slit proteins and nucleic acids for inhibiting platelet coagulation and related disorders. Further provided is a vascular device coated with Slit protein or a cell expressing a Slit protein.

10 Claims, 44 Drawing Sheets

HUVEC

HAEC

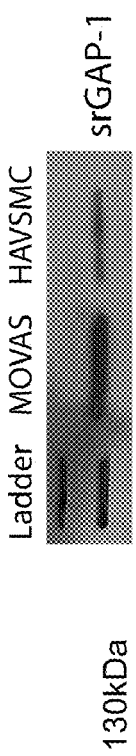
Figure 9B
Figure 9A
Figure 9D HAVSMC
Figure 9C MOVAS

SEQUENCE LISTING

```
<160> NUMBER OF SEQ ID NOS: 8

<210> SEQ ID NO 1
<211> LENGTH: 22
<212> TYPE: DNA
<213> ORGANISM: Homo sapiens

<400> SEQUENCE: 1
ctatcggcca tctggagcca ac                                                  22
```

```
<210> SEQ ID NO 2
<211> LENGTH: 24
<212> TYPE: DNA
<213> ORGANISM: Homo sapiens

<400> SEQUENCE: 2
ggaacaagaa agggaatgac cacg                                          24

<210> SEQ ID NO 3
<211> LENGTH: 23
<212> TYPE: DNA
<213> ORGANISM: Homo sapiens

<400> SEQUENCE: 3
caactggaga cctcacaatc acc                                           23

<210> SEQ ID NO 4
<211> LENGTH: 23
<212> TYPE: DNA
<213> ORGANISM: Homo sapiens

<400> SEQUENCE: 4
gtgccttgct cttgaattgt tgc                                           23

<210> SEQ ID NO 5
<211> LENGTH: 22
<212> TYPE: DNA
<213> ORGANISM: Homo sapiens

<400> SEQUENCE: 5
atcacgatcc gtggagggaa gc                                            22

<210> SEQ ID NO 6
<211> LENGTH: 21
<212> TYPE: DNA
<213> ORGANISM: Homo sapiens

<400> SEQUENCE: 6
tcatcttcgg cactcacatg c                                             21

<210> SEQ ID NO 7
<211> LENGTH: 21
<212> TYPE: DNA
<213> ORGANISM: Homo sapiens

<400> SEQUENCE: 7
agacccacac cacctcctgc c                                             21

<210> SEQ ID NO 8
<211> LENGTH: 22
<212> TYPE: DNA
<213> ORGANISM: Homo sapiens

<400> SEQUENCE: 8
taaactgctc acccaccaca gc                                            22
```

METHODS AND USES FOR INHIBITING PLATELET COAGULATION

RELATED APPLICATIONS

This application claims the benefit under 35 USC §119(e) of U.S. provisional application No. 61/397,666 filed on Jun. 15, 2010, which is incorporated herein in its entirety.

INCORPORATION OF SEQUENCE LISTING

A computer readable form of the Sequence Listing "20925-37_SequenceListing.txt" (1,724 bytes), submitted via EFS-WEB and created on May 4, 2011, is herein incorporated by reference.

FIELD

The present disclosure relates to methods and uses for inhibiting platelet coagulation and for treating associated conditions and diseases comprising administering a Slit protein or nucleic acid. The disclosure also relates to vascular devices coated with Slit proteins or cells expressing Slit proteins and methods and uses thereof.

BACKGROUND

In vascular injury and atherogenesis different cell types are recruited to the injured vessel. Early on, circulating leukocytes, especially monocytes, are recruited to the vessel by chemoattractant signals. After adhering to the endothelial lining of vessels, monocytes migrate across the endothelium, where they differentiate into macrophages and ultimately become lipid-laden foam cells. Attractant signals also recruit VSMC from the medial to the intimal layer, where they proliferate and secrete extracellular matrix proteins, causing neointimal proliferation. In the injured blood vessel, platelets adhere to endothelium, to macrophages, and to exposed collagen. Platelets become activated, spread, and secrete cytokines and other inflammatory mediators. These mediators worsen vascular injury by recruiting and activating more leukocytes, by stimulating migration and proliferation of VSMC, and by recruiting more platelets. Collectively, these individual events promote vascular inflammation, neointimal proliferation, and thrombosis, causing occlusion of both native and stented blood vessels.

Cardiovascular disease leading to heart attack and stroke remains the leading cause of mortality and morbidity in the Western world (Libby 2002; Meadows and Bhatt 2007). Atherosclerosis is a progressive disease characterized by accumulation of inflammatory cells and vascular smooth muscle cells (VSMC) within the intima of injured blood vessels. The atherosclerotic plaque is made up of immune cells, including monocytes, macrophages, neutrophils, T lymphocytes, and VSMC which migrate from the media to the intima, where they proliferate and secrete extracellular matrix proteins. Platelets have also been implicated in the initiation of atherosclerotic lesion formation (Massberg, Brand et al. 2002; Huo, Schober et al. 2003; von Hundelshausen and Weber 2007). These events result in progressive narrowing of the vessel, allowing platelet aggregation and activation to ultimately form vascular occlusive thrombi, precipitating acute coronary syndromes and ischemic stroke (Gawaz, Langer et al. 2005).

Strategies that block recruitment to the intima of immune cells and VSMC are partially protective against vascular injury in both animal models and human patients. Inhibiting monocyte and VSMC recruitment to selected chemoattractants partially prevents atherosclerosis and its clinical manifestations, and simultaneous blockade of two chemotactic pathways confers additional, but not complete, benefit (Boring, Gosling et al. 1998; Gosling, Slaymaker et al. 1999; Libby 2002; Combadiere, Potteaux et al. 2003; Lesnik, Haskell et al. 2003; Saederup, Chan et al. 2008). Medical therapies that inhibit platelet activation and aggregation are a mainstay of treatment for patients at risk for cardiovascular events, making anti-platelet agents the most prescribed drugs worldwide (Meadows and Bhatt 2007). However, these agents also only provide partial protection against cardiovascular events.

Acute kidney injury (AKI) develops in 5% of hospitalized patients and leads to significant morbidity, mortality and financial costs (Brady and Singer 1995; Korkeila, Ruokonen et al. 2000; Bagshaw 2006). Fifty percent of cases of AKI result from ischaemia-reperfusion injury (IRI) (Thadhani, Pascual et al. 1996). Despite significant advances in understanding the cellular and molecular events that cause kidney IRI, specific therapy remains elusive and management is mainly supportive (Jo, Rosner et al. 2007).

The recruitment of circulating leukocytes, particularly neutrophils into the injured kidney is a key component of AKI caused by IRI (Okusa 2002). Once recruited to the injured kidney, the recruited leukocyte subsets promote and perpetuate the organ damage (Furuichi, Wada et al. 2003; Friedewald and Rabb 2004; Fiorina, Ansari et al. 2006). Therapies targeting different leukocyte subsets are partially effective in ameliorating the injury associated with AKI (Kelly, Williams et al. 1994; Singbartl, Green et al. 2000; Jo, Sung et al. 2006). However given the diversity of the recruiting signals and the cells recruited, it is unlikely that a therapy directed at a single leukocyte will be entirely effective (Salmela, Wramner et al. 1999). Early after reperfusion, platelets also adhere within capillaries of the vasa recta. After adhering, platelets become activated, spread, and release acute inflammatory mediators and pro-fibrotic growth factors that intensify kidney injury and scarring (Li, L and Okusa, M D 2006. Nat Clin Pract Nephr 2:432-444). Therapies that inhibit platelet function also partially, but not completely, ameliorate AKI (Singbartl 2000; Chintala M S et al 1994 JPET 271:1203-1208).

The Slit family of secreted proteins, together with their transmembrane receptor, Roundabout (Robo), act as repellents for migrating neurons and axons during development of the central nervous system (Kidd, Brose et al. 1998; Brose, Bland et al. 1999; Kidd, Bland et al. 1999). It has recently been appreciated that Slit and Robo are also expressed in mature organisms, and an isoform of Robo, Robo-1, has been detected on the surface of several cell types involved in vascular injury, IRI and atherogenesis, including VSMC, neutrophils and mononuclear leukocytes (Wu, Feng et al. 2001; Prasad, Fernandis et al. 2004; Liu, Hou et al. 2006; Prasad, Qamri et al. 2007; Tole, Mukovozov et al. 2009). Slit2 has been shown to interact with Robo-1 to prevent directional migration of these cells in response to diverse inflammatory chemoattractant cues both in vitro and in vivo (Wu, Feng et al. 2001; Guan, Zu et al. 2003; Kanellis, Garcia et al. 2004; Prasad, Fernandis et al. 2004; Liu, Hou et al. 2006; Prasad, Qamri et al. 2007; Tole, Mukovozov et al. 2009).

SUMMARY

The present inventor has shown that Robo-1 is expressed in megakaryocytes and platelets, and is present on the platelet cell surface in humans and mice. The present inventor further demonstrated that Slit2 is a potent inhibitor of platelet adhesion, spreading and activation in response to diverse stimuli in vitro, and also impairs platelet procoagulant function in vivo. Also demonstrated is that Slit2 is effective at inhibiting neutrophil adhesion in ischaemia/reperfusion injury of the kidney.

Accordingly, in one aspect, the present disclosure provides a method for inhibiting platelet coagulation comprising administering a Slit protein or nucleic acid to a cell or animal in need thereof. Also provided is use of a Slit protein or nucleic acid for inhibiting platelet coagulation in a cell or animal in need thereof. Further provided is use of a Slit protein or nucleic acid in the manufacture of a medicament for inhibiting platelet coagulation in a cell or animal in need thereof. Also provided is a Slit protein or nucleic acid for use in inhibiting platelet coagulation in a cell or animal in need thereof.

The method of inhibiting platelet coagulation disclosed herein is useful for treating subjects having related conditions and diseases and for treating subjects at risk of excessive platelet coagulation. In one embodiment, the method is for treating thrombosis, clot formation, atherosclerosis, cardiovascular disease, pulmonary embolism and patients with hypercoagulable state.

The present disclosure also provides a method for treating acute kidney injury comprising administering a Slit protein or nucleic acid to a cell or animal in need thereof. Also provided is use of a Slit protein or nucleic acid for treating acute kidney injury in a cell or animal in need thereof. Further provided is use of a Slit protein or nucleic acid in the manufacture of a medicament for treating acute kidney injury in a cell or animal in need thereof. Also provided is a Slit protein or nucleic acid for use in treating acute kidney injury in a cell or animal in need thereof.

In yet another aspect, the present disclosure provides a vascular device coated with a Slit protein or a cell expressing a Slit protein. In one embodiment, the cell comprises an expression vector comprising a nucleic acid encoding the Slit protein. In an embodiment, the vascular device is a vascular stent, vascular graft or a vascular catheter.

In one embodiment, the Slit protein is Slit1, Slit2 or Slit3 or a variant thereof. In another embodiment, the Slit protein is Slit2 or Slit2-N or a variant thereof.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 9 shows vascular smooth muscle cells (VSMC) express Robo-1 and srGAP1. Immunoblot analysis of A) Robo-1 and B) srGAP-1 expression in cultured mouse MOVAS aortic VSMC and human aortic vascular smooth muscle cells (HAVSMC). Immunofluorescence analysis of srGAP1 expression in C) MOVAS cells and D) HAVSMCs.

DETAILED DESCRIPTION

Figure 1:
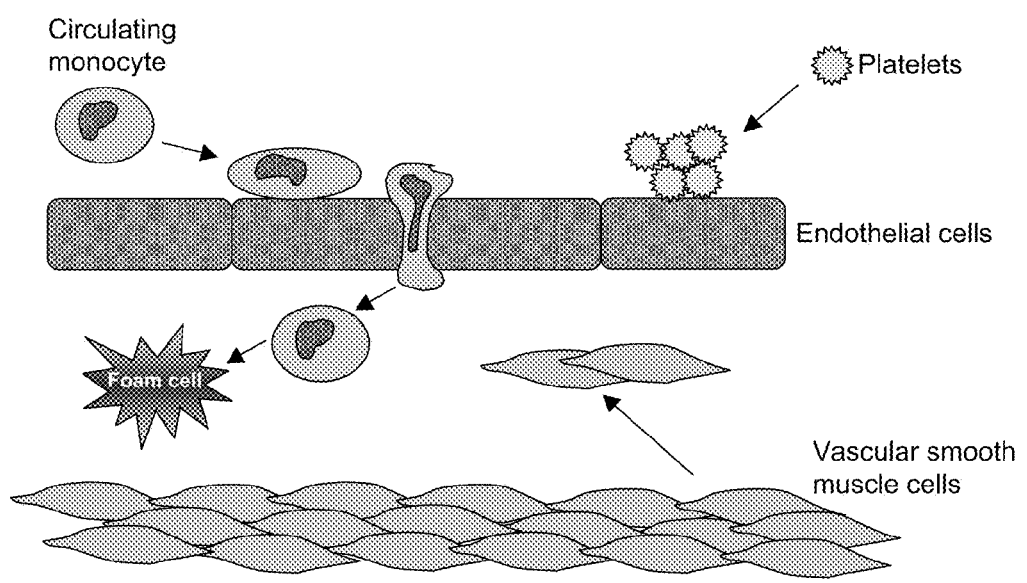
FIG. 1 shows the formation of an atherosclerotic lesion.

Slit proteins act as developmental neuronal repellents, and Slit2 via interaction with its receptor, Robo-1, impairs inflammatory recruitment of leukocytes and vascular smooth muscle cells. Robo-1 expression has presently been shown in human platelets and megakaryocytes, and its presence was confirmed on the surface of human and murine platelets via immunofluorescence microscopy. In static and shear assays, Slit2 impaired platelet adhesion and spreading on extracellular matrix substrates by suppressing activation of Akt but not Rac1, Cdc42, Erk or p38 MAPK. Slit2 also inhibited ADP-mediated platelet activation, and its potent in vivo effects were evident in prolonging mouse tail bleeding times in a dose-dependent manner. Thus in addition to inhibiting vascular inflammation and neointimal proliferation, Slit2 is a powerful negative regulator of platelet activation. The anti-thrombotic properties of Slit2 make it useful as a potent agent capable of simultaneously preventing the vascular inflammation, neointimal proliferation and thrombus formation that collectively result in occlusion of diseased vessels.

Methods and Uses

Accordingly, in one aspect, the present disclosure provides a method for inhibiting platelet coagulation comprising administering a Slit protein or nucleic acid to a cell or animal in need thereof. Also provided is use of a Slit protein or nucleic acid for inhibiting platelet coagulation in a cell or animal in need thereof. Further provided is use of a Slit protein or nucleic acid in the manufacture of a medicament for inhibiting platelet coagulation in a cell or animal in need thereof. Also provided is a Slit protein or nucleic acid for use in inhibiting platelet coagulation in a cell or animal in need thereof.

The phrase "inhibiting platelet coagulation" as used herein refers to preventing or reducing platelet aggregation, adhesion, spreading and/or clotting. Inhibition platelet coagulation as used herein refers to a decrease of at least 5%, 10%, 20%, 30%, 40%, 50%, 60%, 70%, 80% or more of platelet coagulation compared to a control.

Inhibiting platelet coagulation is useful in treating a variety of diseases and conditions, including without limitation, thrombosis, atherosclerosis, cardiovascular disease, in-stent restenosis, clot formation, pulmonary embolism, subjects with hypercoagulable state and acute kidney injury.

Accordingly, the present disclosure provides a method of treating a platelet coagulation related disease or condition comprising administering a Slit protein or nucleic acid to a cell or animal in need thereof. Also provided is use of a Slit protein or nucleic acid for treating a platelet coagulation related disease or condition in a cell or animal in need thereof. Further provided is use of a Slit protein or nucleic acid in the manufacture of a medicament for treating a platelet coagulation related disease or condition in a cell or animal in need thereof. Also provided is a Slit protein or nucleic acid for use in treating a platelet coagulation related disease or condition in a cell or animal in need thereof.

The term "thrombosis" as used herein refers to the formation or presence of coagulated blood attached at the site of formation and includes, without limitation, acute coronary artery thrombosis which can lead to myocardial infarction, acute cerebral artery thrombosis, which can lead to stroke and ischemic attacks, thrombosis in vascular catheters, thrombosis of vascular grafts, thrombosis associated with organ transplantation, venous thrombosis, renal vein thrombosis, clot formation in bypass, hemodialysis or continuous renal replacement therapy (CRRT) circuits, and thrombosis in dialysis vascular fistulas and grafts.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

Inhibiting platelet coagulation is also useful in prophylactically treating a subject at risk of excessive platelet coagulation, including without limitation, post-coronary artery or carotid artery balloon angioplasty, subjects with vascular catheters, bypass circuits, hemodialysis circuits and CRRT circuits, organ transplant recipients, subjects at risk for cardiovascular disease who typically are on aspirin treatment, subjects at risk for venous thrombosis, subjects at risk for thromboembolism, such as subjects with arrhythmias, subjects with dialysis fistulas and grants and subjects with hypercoagulable state. Subjects with hypercoagulable state include, without limitation, subjects with nephrotic syndrome, inherited disorders of Factor V Leiden, protein C or S deficiency, and antithrombin III deficiency.

Accordingly, the present disclosure also provides a method of prophylactically treating a subject at risk of excessive platelet coagulation comprising administering a Slit protein or nucleic acid encoding a Slit protein to a cell or animal in need thereof. Also provided is use of a Slit protein or nucleic acid for prophylactically treating a subject at risk of excessive platelet coagulation in a cell or animal in need thereof. Further provided is use of a Slit protein or nucleic acid in the manufacture of a medicament for prophylactically treating a subject at risk of excessive platelet coagulation in a cell or animal in need thereof. Also provided is a Slit protein or nucleic acid for use in prophylactically treating a subject at risk of excessive platelet coagulation in a cell or animal in need thereof.

In one embodiment, the present disclosure provides a method of prophylactically treating a subject at risk of excessive platelet coagulation comprising instilling a Slit protein or nucleic acid encoding a Slit protein locally during balloon angioplasty. Also provided is use of a Slit protein or nucleic acid encoding a Slit protein for instillation locally during balloon angioplasty. Further provided is use of a Slit protein or nucleic acid encoding a Slit protein in the preparation of a medicament for instillation locally during balloon angioplasty. Also provided is a Slit protein or nucleic acid encoding a Slit protein for use in instillation locally during balloon angioplasty.

The term "a cell" as used herein includes a plurality of cells and refers to all types of cells. Administering a compound to a cell includes in vivo, ex vivo and in vitro treatment.

The term "animal" or "subject" as used herein includes all members of the animal kingdom, optionally mammal. The term "mammal" as used herein is meant to encompass, without limitation, humans, domestic animals such as dogs, cats, horses, cattle, swine, sheep, goats, and the like, as well as wild animals. In an embodiment, the mammal is human.

The term "effective amount" as used herein means a quantity sufficient to, when administered to an animal, effect beneficial or desired results, including clinical results, and as such, an "effective amount" depends upon the context in which it is being applied. For example, in the context of inhibiting platelet coagulation, it is the amount of the a Slit protein or nucleic acid sufficient to achieve such an inhibition as compared to the response obtained without administration of the a Slit protein or nucleic acid.

The term "Slit protein" as used herein is intended to refer to any one of a family of proteins known to be ligands for the Roundabout receptor (Robo), including Slit1, Slit2 and Slit3. The term "Slit" is intended to encompass the protein from any species or source, optionally, human Slit proteins. The term "Slit nucleic acid" is intended to encompass a nucleic acid encoding a Slit protein. The nucleic acid and protein sequences of human Slit1 are set forth as NM_003061 and NP_003052, respectively. The nucleic acid and protein sequences of human Slit2 are set forth as AF133270.1 and AAD25539, respectively. The nucleic acid and protein sequences of human Slit3 are set forth as NM_003062.2 and NP_003053.1, respectively.

In an embodiment, the Slit protein is Slit1, 2 or 3 or a variant thereof. In another embodiment, the Slit protein is Slit2 or Slit2-N or a variant thereof.

The term "Slit2-N" or "N-Slit2" as used herein refers to a truncated Slit2 protein comprising the N-terminal which contains the leucine rich region necessary for binding to the Robo-1 receptor and for downstream signal transduction.

The term "nucleic acid molecule" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "variant" as used herein includes modifications, substitutions, additions, derivatives, analogs, fragments or chemical equivalents of the Slit nucleic acid or amino acid sequences disclosed herein that perform substantially the same function in substantially the same way. For instance, the variants of the Slit peptides would have the same function, for example, of inhibiting platelet adhesion, spreading and/or clotting.

Variants also include peptides with amino acid sequences that are substantially or essentially identical to the amino acid sequences of the Slit protein or nucleic acid molecules with nucleic acid sequence that are substantially or essentially identical to the nucleic acid sequence encoding the Slit proteins.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "sequence identity" as used herein refers to the percentage of sequence identity between two polypeptide and/or nucleotide sequences.

To determine the percent identity of two amino acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues at corresponding amino acid positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The percentage of identity between two polypeptide sequences, the amino acid sequences of such two sequences are aligned, for example using the Clustal W algorithm (Thompson, J D, Higgins D G, Gibson T J, 1994, *Nucleic Acids Res.* 22(22): 4673-4680.), together with BLOSUM 62 scoring matrix (Henikoff S, and Henikoff J. G., 1992, *Proc. Natl. Acad. Sci.* USA 89: 10915-10919.) and a gap opening penalty of 10 and gap extension penalty of 0.1, so that the highest order match is obtained between two sequences wherein at least 50% of the total length of one of the sequences is involved in the alignment.

Other methods that may be used to align sequences are the alignment method of Needleman and Wunsch (Needleman and Wunsch. *J. Mol. Biol.*, 1970, 48:443), as revised by Smith and Waterman (Smith and Waterman. *Adv. Appl. Math.* 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton *SIAM J. Applied Math.* 1988, 48:1073) and those described in Computational Molecular Biology (Computational Molecular Biology, Lesk, e.d. Oxford University Press, New York, 1988, *Biocomputing: Informatics and Genomics Projects*). Generally, computer programs will be employed for such calculations.

The term "analog" means an amino acid or nucleic acid sequence which has been modified as compared to the Slit sequences wherein the modification does not alter the utility of the sequence (e.g. binding to Robo) as described herein. The modified sequence or analog may have improved properties over the Slit sequences. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Slit protein may be modified to contain amino acid substitutions, insertions and/or deletions that do not alter the binding and/or activating properties of the protein. Conserved amino acid substitutions involve replacing one or more amino acids of the protein with amino acids of similar charge, size, and/or hydrophobicity characteristics. When only conserved substitutions are made the resulting analog should be functionally equivalent to Slit. Non-conserved substitutions involve replacing one or more amino acids of the conjugate protein with one or more amino acids which possess dissimilar charge, size, and/or hydrophobicity characteristics.

The disclosure further encompasses nucleic acid molecules that differ from any of the nucleic acid molecules disclosed herein in codon sequences due to the degeneracy of the genetic code.

Administration or use of a nucleic acid encoding Slit protein or variant thereof includes administration or use of a vector containing the nucleic acid molecule and the necessary regulatory sequences for the transcription and translation of the inserted sequence.

Suitable regulatory sequences may be derived from a variety of sources, including bacterial, fungal, viral, mammalian, or insect genes (for example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by Slit sequences and/or its flanking regions.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, California, U.S.A.).

In an embodiment, the methods and uses further comprise administration or use of another anti-coagulant in combination with the Slit protein or nucleic acid. Other anti-coagulants include, without limitation, unfractionated heparin, low molecular weight heparin, warfarin, dipyridamole, and aspirin.

The methods and uses described herein include administration or use of the Slit protein or nucleic acid alone or as part of a pharmaceutical composition comprising the Slit protein.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003-20$^{th}$ Edition) and in The United States Pharmacopeia: The National Formulary (USP 24 NF19) published in 1999).

On this basis, the pharmaceutical compositions for use in the methods and/or uses described herein include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as other anti-coagulants.

Devices

In another aspect, the present disclosure provides a vascular device coated with a Slit protein or a cell expressing a Slit protein. Vascular devices include any device that is insertable in a subject's vasculature such as a blood vessel, typically in the shape of a tube, that permits introduction or withdrawal of fluid or which acts to keep the passageway open and includes without limitation, stents, grafts and catheters. Accordingly, in one embodiment, the vascular device is a vascular stent, graft or catheter.

Typical vascular devices include, without limitation, central venous catheters, hemodialysis catheters, Portacaths, peripherally-inserted central catheters (PICC), and vascular stents.

In one embodiment, the vascular device is coated with Slit1, 2 or 3 or a variant thereof. In another embodiment, the vascular device is coated with Slit2 or Slit2-N or a variant thereof.

The vascular device is either coated directly with the Slit protein or is coated with cells that express the Slit protein.

Cells that express the Slit protein are readily prepared by a person skilled in the art using an expression system as described herein. Typical expression systems include lentiviral expression systems. In one embodiment, the cell is an endothelial cell.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Preliminary Results

Slit2 Inhibits Monocyte/Macrophage Chemotaxis In Vitro and In Vivo.

Figure 2:
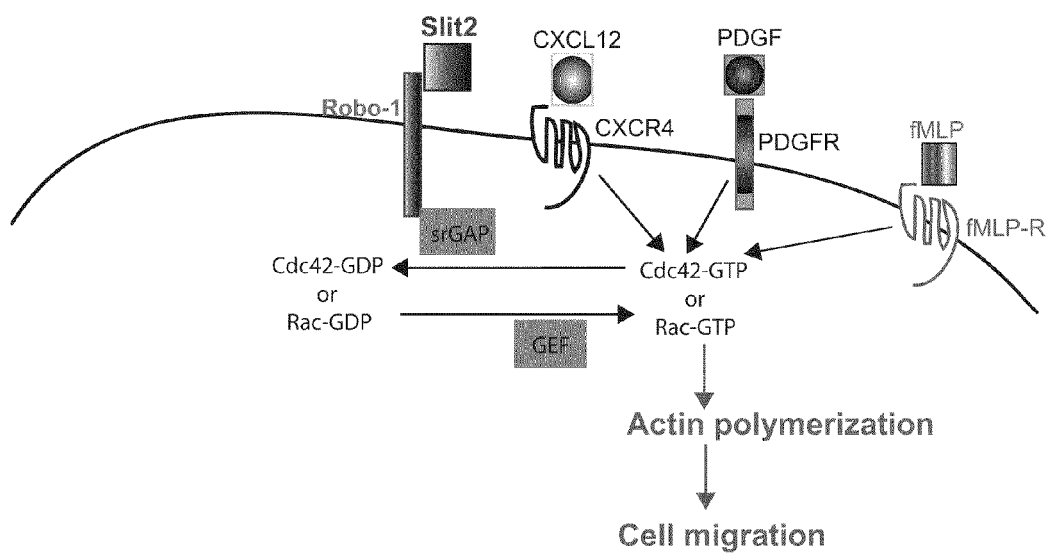
FIG. 2 shows Slit2 inhibits cellular migration by preventing activation of the small GTPases, Cdc42 and Rac. srGAP, Slit-Robo GTPase activating protein; GEF, guanine nucleotide exchange factor; PDGF, platelet-derived growth factor; PDGFR, platelet-derived growth factor receptor.
Figure 3A:
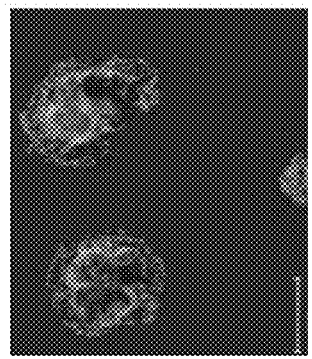
FIG. 3 shows neutrophils express Robo-1 and Slit2 inhibits neutrophil chemotaxis in vitro and in vivo. A) Immunoblot analysis of Robo-1 expression in primary neutrophils isolated from human peripheral blood and murine bone marrow using anti-Robo-1 antibody (Ab). B) Immunofluorescence analysis of Robo-1 expression in human neutrophils. C) To detect cell surface Robo-1, human neutrophils (left) and mouse neutrophils (right) were labeled with anti-Robo-1 Ab and analyzed by flow cytometry. D) Images of human neutrophils incubated with various concentrations of purified Slit2 for 10 mins. then subjected to Transwell migration assays. E) Bar graph analysis of results in D). F) Bar graph analysis of neutrophil numbers in peritoneal lavage of adult CD1 mice one hour after: 1) intravenous tail vein injections of Slit2, and 2) intraperitoneal injection of sodium periodate, C5a, or monocyte inflammatory protein-2 (MIP-2) one hour later.
Figure 3B:
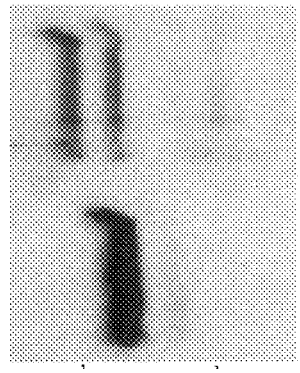
Figure 3C:
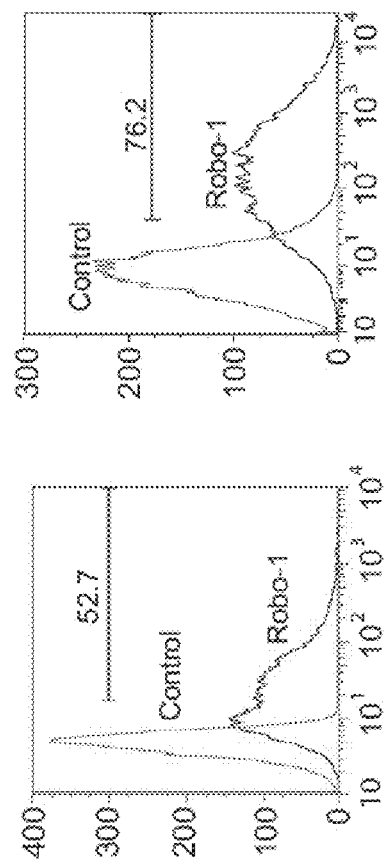
Figure 3D:
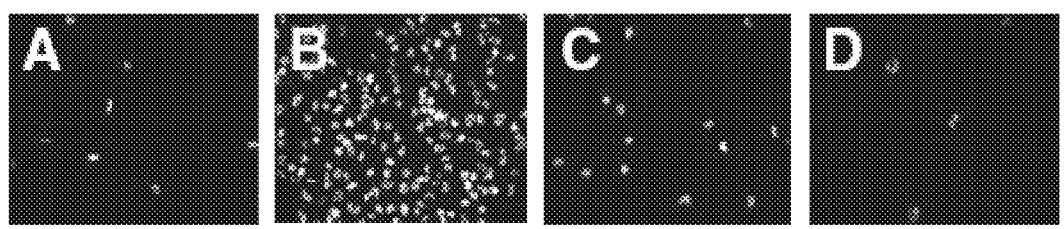
Figure 3E:
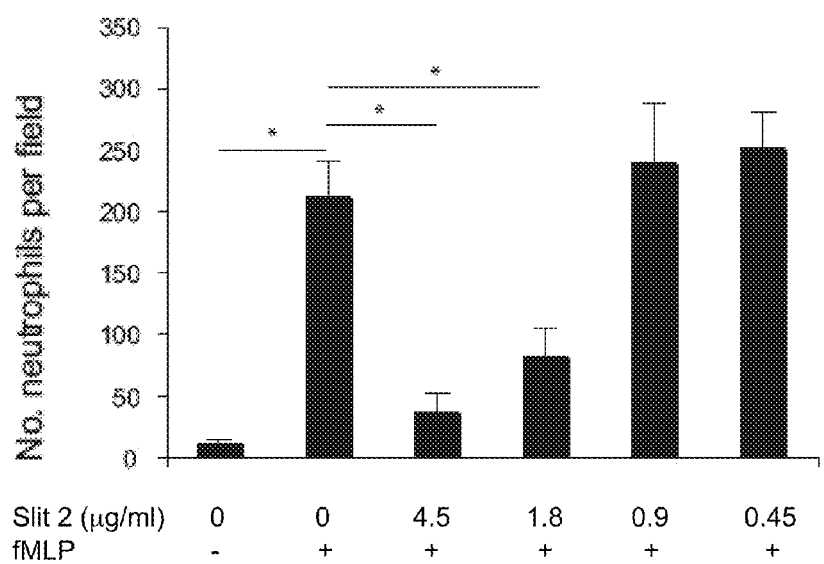
Figure 3F:
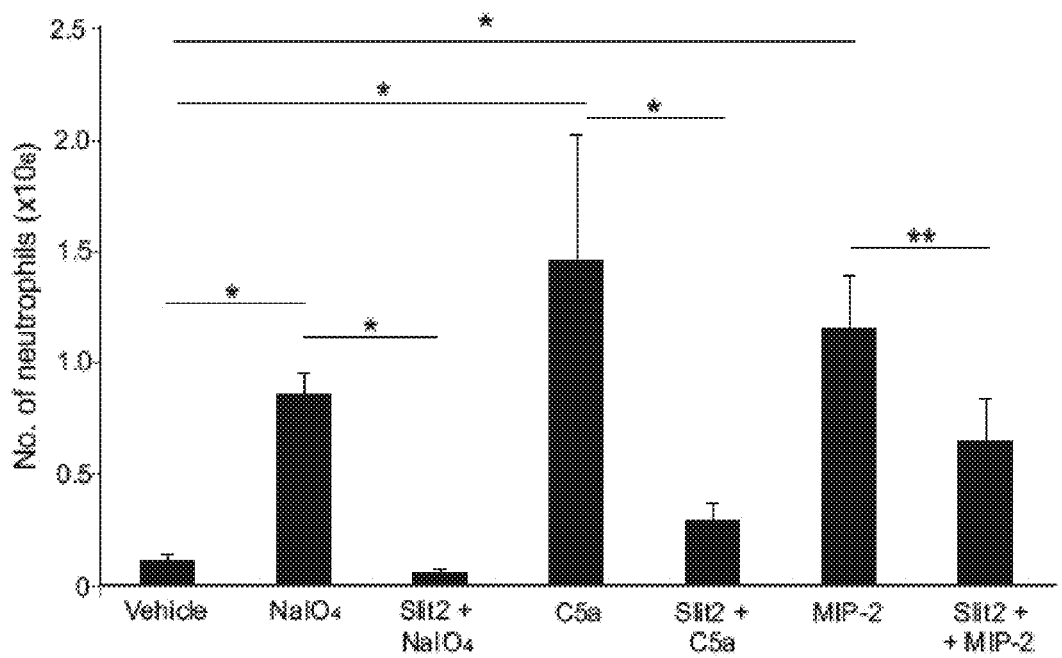

Many of the pathologic events that occur in the formation of an atherosclerotic lesion (FIG. 1), including migration of monocytes and VSMC, and spreading of platelets, require activation of the small Rho-family guanosine triphosphatases (GTPases), Cdc42 and Rac. Slit2 inhibits cellular migration by preventing activation of the small GTPases, Cdc42 and Rac (FIG. 2). Exposure to different chemoattractants, such as fMLP, PDGF, or CXCL12 induces directional movement of neutrophils, vascular smooth muscle cells, lymphocytes and breast cancer cells, respectively. Binding of the chemoattractants to their receptors results in activation of the small GTPases, Cdc42 and Rac, at the leading edge of the polarizing cell. The net result is actin polymerization and directional movement of the cell towards the chemotactic stimulus. Binding of Slit2 to the transmembrane Robo-1 receptor inhibits cell chemotaxis, by enhancing associations between the intracellular domain of Robo-1 and a novel class of Slit Robo GTPase activating proteins (srGAPs). These srGAPS promote conversion of the active, GTP-bound forms of Cdc42 and Rac to the inactive, GDP-bound forms. In this way, Slit2 inhibits directional migration of diverse cell types. srGAP, Slit-Robo GTPase activating protein; GEF, guanine nucleotide exchange factor; PDGF, platelet-derived growth factor; PDGFR, platelet-derived growth factor receptor.

Figure 16A:
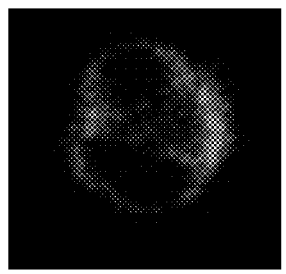
FIG. 16 shows generation of srGAP1 expression plasmids that constitutively localize to the plasma membrane. A) Immunofluorescence analysis of endogenous srGAP1 expression in human peripheral blood neutrophils using srGAP1 Ab. C) Modified Venus- and green fluorescent protein (GFP)-tagged srGAP1 cDNA expression plasmids having a CAAX consensus sequence together with a polycationic stretch added to the carboxy-terminus were generated (srGAP1-CAAX-Venus and srGAP1-CAAX-GFP) and transfected into COS-7 cells. Immunofluorescent analysis was performed to determine localization of srGAP1-CAAX relative to plasma membrane, which was labeled using Alexa594-conjugated wheat germ agglutinin.
Figure 16B:
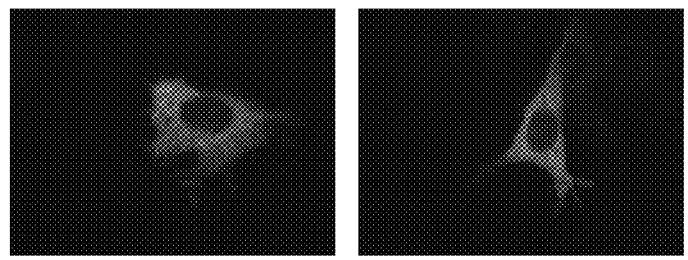
Figure 16C:
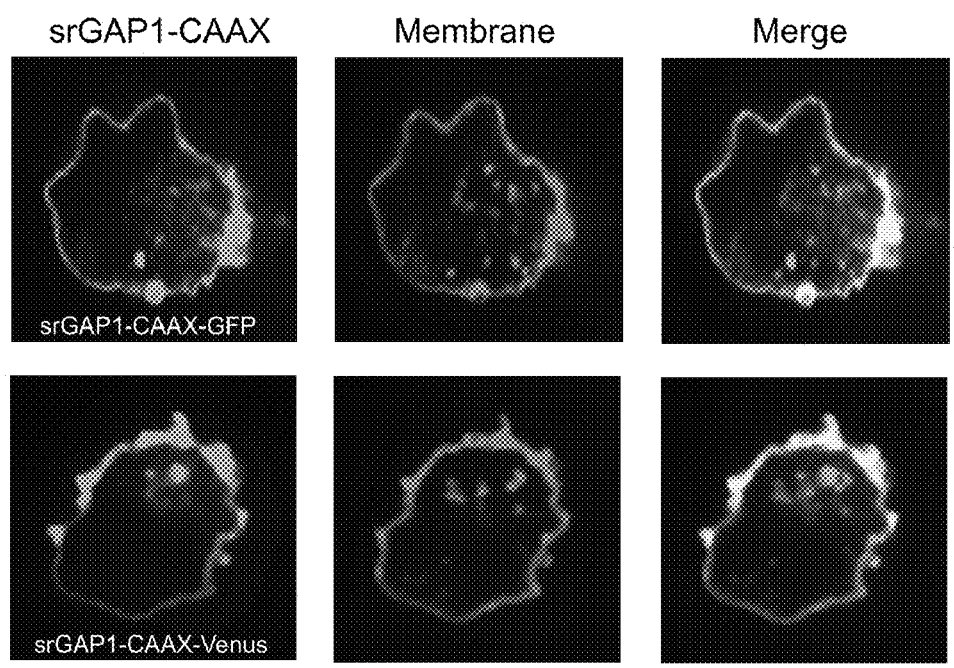

To study whether Slit2 activates srGAP1 through sub-cellular localization, expression plasmids that direct localization of srGAP1 to different cell compartments were used. Referring to FIG. 16: A) To study how Slit2 activates srGAP1, the subcellular distribution of endogenous srGAP1 was first examined. Human peripheral blood neutrophils were fixed, permeabilized, and labeled with an Ab specifically recognizing srGAP1. srGAP was seen in the cytosol and at the plasma membrane. B) COS-7 cells were transfected with a cDNA expression plasmid encoding Venus-tagged srGAP1. The majority of srGAP1-Venus was seen in the cytosol. B) Modified Venus and green fluorescent protein (GFP)-tagged srGAP1cDNA expression plasmids that have a CAAX consensus sequence together with a polycationic stretch added to the carboxy-terminus were generated (srGAP1-CAAX-Venus and srGAP1-CAAX GFP). When COS-7 cells were transfected with srGAP1-CAAX-GFP and srGAP1-CAAX-Venus, the fusion proteins produced localized predominantly to the plasma membrane, which was labeled using Alexa594-conjugated wheat germ agglutinin.

It was found that primary human and murine neutrophils express Robo-1 and Slit2 impairs their migration, in vitro and in vivo, towards diverse attractants. Referring to FIG. 3: A) Primary neutrophils were isolated from human peripheral blood and murine bone marrow, and immunoblotting performed using specific anti-Robo-1 Ab. B) Human neutrophils were labeled with anti-Robo-1 Ab followed by a Cy3-conjugated secondary Ab. C) To detect cell surface Robo-1, human neutrophils (left) and mouse neutrophils (right) were labeled with anti-Robo-1 Ab and analyzed by flow cytometry. D) Human neutrophils were incubated with the indicated concentrations of purified Slit2 for 10 min prior to performing Transwell migration assays. Neutrophils were placed in the top chamber and fMLP ($10^{-6}$ M) in the bottom chamber. E) After 30 min, the number of neutrophils that had migrated into the bottom chamber was quantified. F) Adult CD1 mice received intravenous injections of Slit2 via tail vein. One hour later, mice were given an intraperitoneal injection of sodium periodate, C5a, or monocyte inflammatory protein-2 (MIP-2). After 1 h, peritoneal lavage was performed and the number of neutrophils present determined.

Figure 4A:
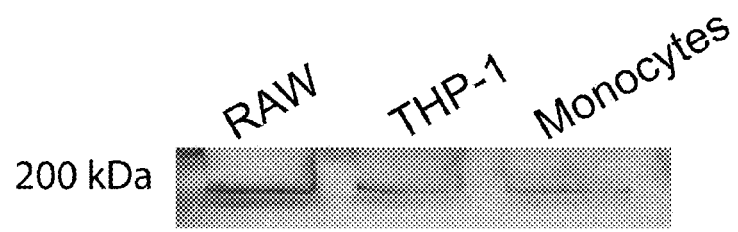
FIG. 4 shows monocytes and macrophages express Robo-1 and srGAP1. A) Immunoblot analysis of Robo-1 expression in cell lysates extracted from murine RAW264.7 macrophage cell line, human THP-1 monocytic cells, and primary human peripheral blood monocytes. B) Immunofluorescence analysis of Robo-1 expression in human peripheral blood monocytes and human THP-1 monocytic cell line. C) Immunofluorescence analysis of srGAP1 expression in THP-1 cells.
Figure 4B:
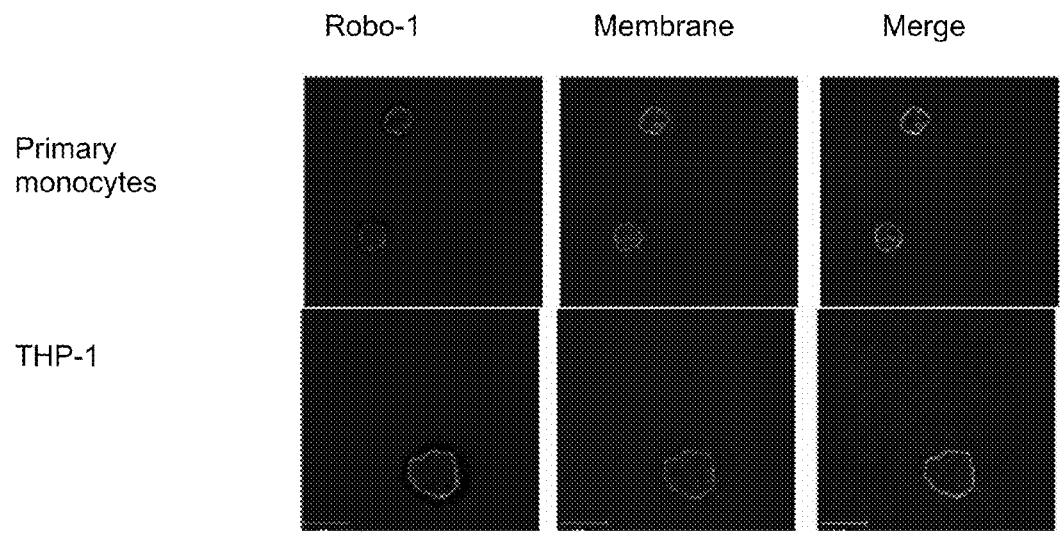
Figure 4C:
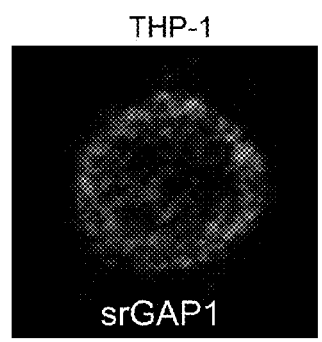
Figure 5A:
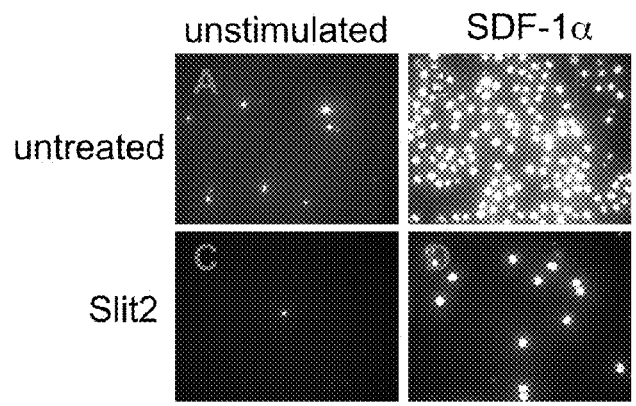
FIG. 5 shows Slit2 inhibits monocyte chemotaxis towards diverse chemokines. A) Transwell analysis of THP-1 cell migration in the absence (untreated) and presence of Slit2 (Slit2) in both unstimulated and SDF-1α-stimulated cells. B) Bar graph analysis of results from A). C) Images of primary human monocytes subjected to chemotaxis assays in the presence of monocyte chemotactic protein-1 (MCP-1) in the presence (+Slit2) or absence (Control) of Slit2 (upper panel). Results are also presented in bar graph format (lower panel). D) Bar graph analysis of results of THP-1 cell transmigration assays in the presence of 3 different classes of chemokines: a CC chemokine (MCP-1), a CXC chemokine (SDF-1α), and a CX3C chemokine (fractalkine, FKN).
Figure 5B:
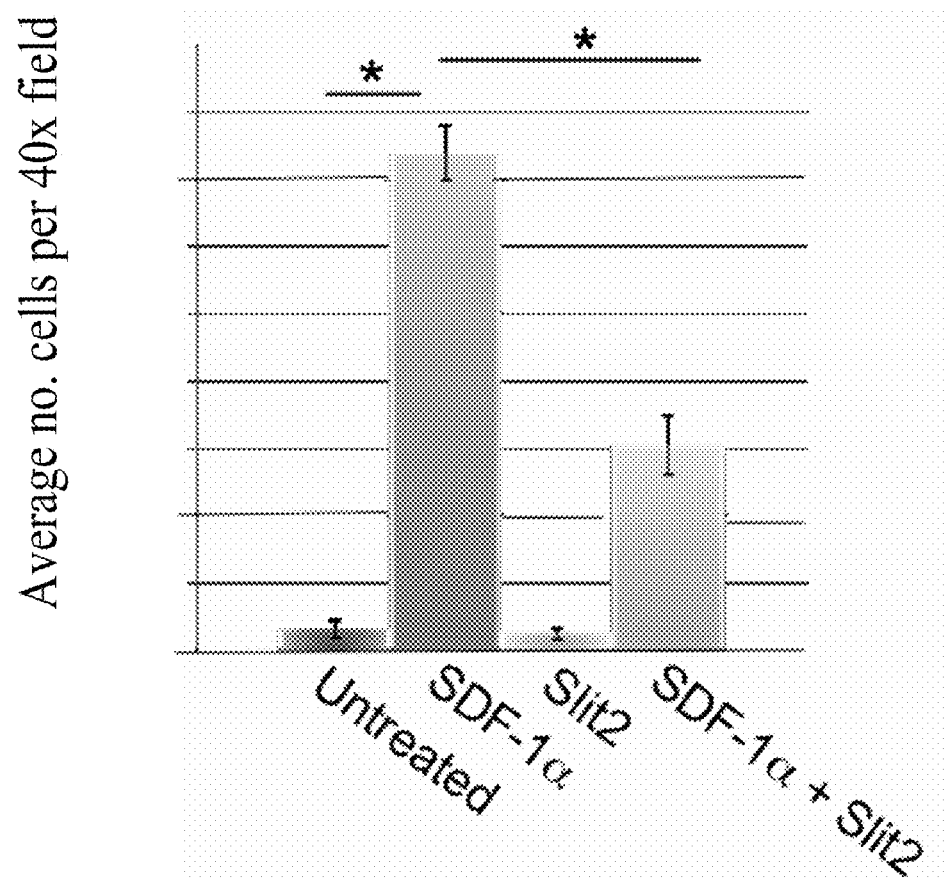
Figure 5C:
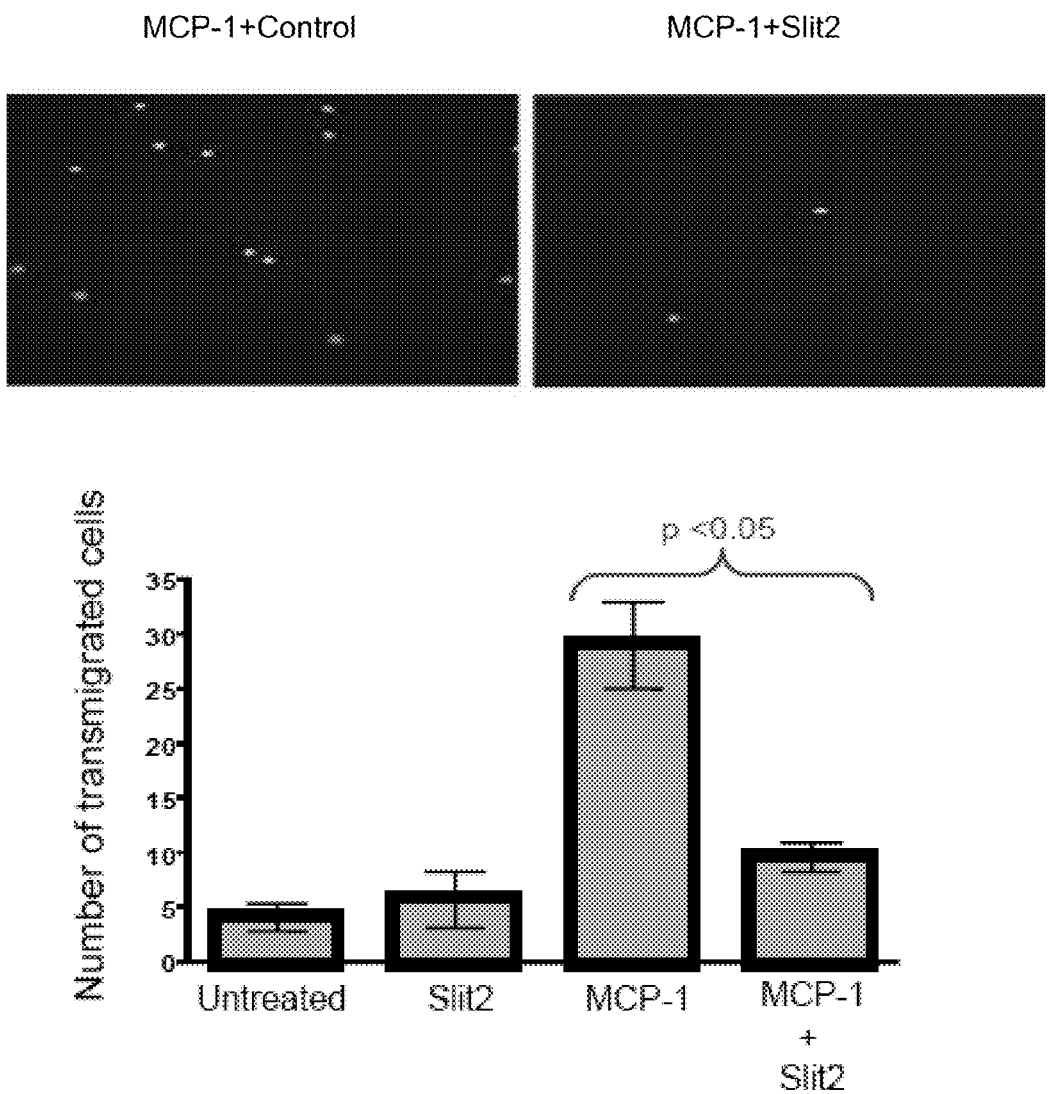
Figure 5D:
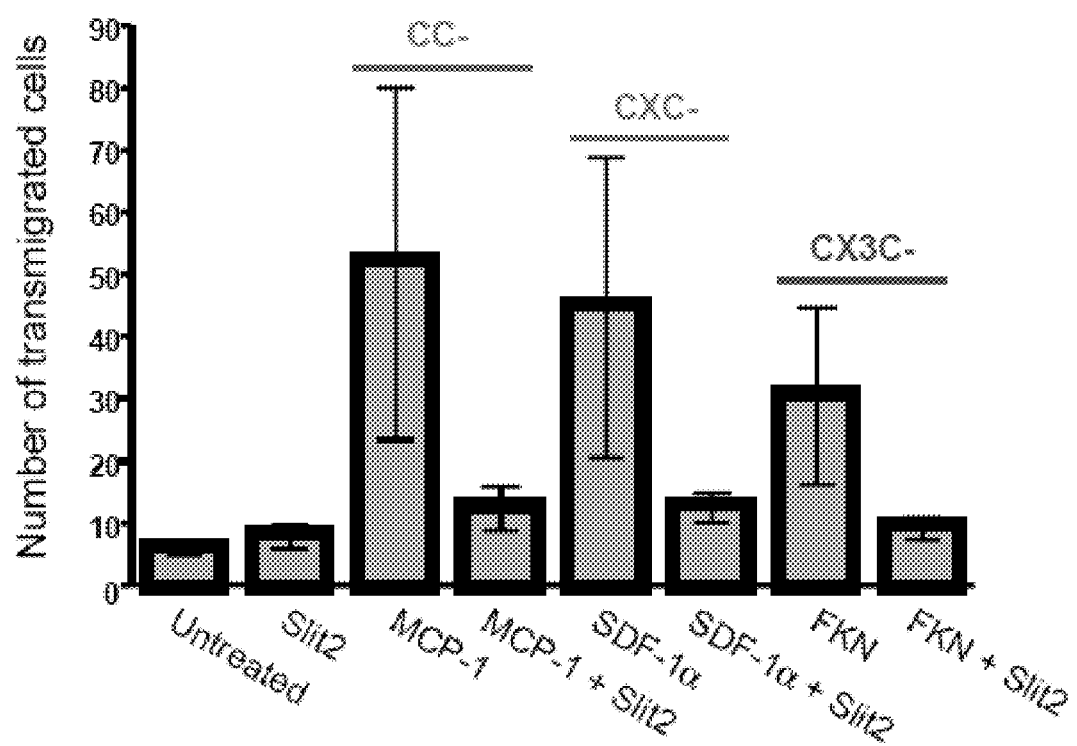

Using immunoblotting and immunofluorescence microscopy, it was found that monocytes and macrophages express both Robo-1 and srGAP1. Referring to FIG. 4: A) Cell lysates were harvested from mouse RAW264.7 macrophage cell line, human THP-1 monocytic cells, and primary human peripheral blood monocytes. Monocytes were isolated from human peripheral blood by gradient separation. Monocytes were isolated from the mononuclear cell layer by negative selection using magnetic beads conjugated to Ab directed against CD3, CD7, CD16, CD19, CD56, CD123, and CD235a to remove contaminating non-monocytic cells (Miltenyi Biotec). Cell purity was confirmed to be >90% using flow cytometry. Immunoblotting was performed using a specific anti-Robo-1 Ab. A band of the expected size was detected by gel electrophoresis. B) Immunofluorescence labeling of human peripheral blood monocytes and THP-1 monocytic cells using anti-Robo-1 primary Ab and Cy3-conjugated secondary Ab, together with Alexa488-conjugated plasma membrane marker. C) Human THP-1 monocytic cells were labeled with an Ab specifically recognizing human srGAP1, followed by Cy3-conjugated secondary Ab.

Transwell assays were performed to study the effects of Slit2 on chemotactic migration of cultured and primary human monocytes. Slit2 inhibited monocyte migration towards chemokines belonging to three different structural families, namely MCP-1 (a CC-chemokine), SDF-1α (a CXC-chemokine), and FKN (a $CX_3C$ chemokine). Referring to FIG. 5: A) THP-1 monocytic cells were labeled with calcein to visualize them and placed in the upper chamber of a Transwell chemotaxis chamber. In the bottom well was placed either SDF-1α alone or SDF-1α with Slit2. B) When cells were incubated with SDF-1α with Slit2, fewer cells transmigrated than when cells were incubated with SDF-1α (*$p<0.001$). n=3. C) Similar results were obtained when chemotaxis assays were performed using primary monocytes isolated from human peripheral blood and the chemokine monocyte chemotactic protein-1 (MCP-1). n=4. D) Transmigration assays were performed using THP-1 cells and 3 different classes of chemokines, namely, MCP-1 (a CC chemokine), SDF-1α (a CXC chemokine), and fractalkine (FKN; a $CX_3C$ chemokine). In preliminary studies, a trend towards less cell chemotaxis in the presence of Slit2 was observed with all 3 chemokines tested. n=3.

Figure 6:
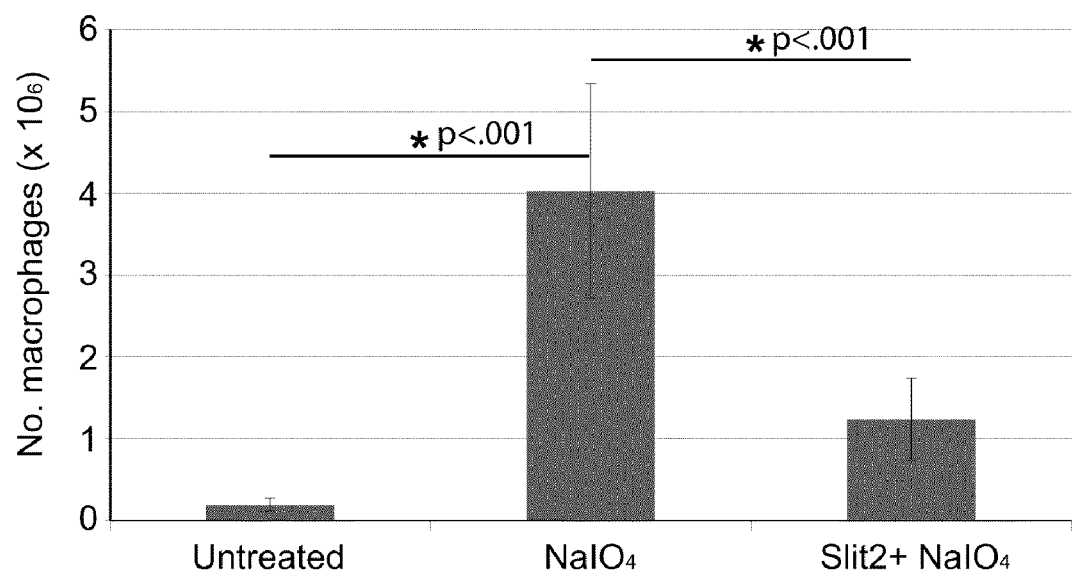
FIG. 6 shows Slit2 inhibits monocyte/macrophage recruitment in vivo. Bar graph analysis of macrophage numbers in peritoneal exudate in a mouse model of experimental peritonitis induced by injection of 1 mL of 5 mM sodium periodate ($NaIO_4$) in PBS. Values represent mean values±SEM for 5 mice in each treatment group.

Using a mouse model of chemical irritant peritonitis, the effects of Slit2 on monocyte/macrophage recruitment in vivo were also tested. Slit2 effectively inhibited recruitment of monocytes/macrophages to the inflamed peritoneal cavity. Referring to FIG. 6: Slit2 (1.8 μg/mouse) was administered intravenously by tail vein injection into adult CD1 mice. One day later, experimental peritonitis was induced by intraperitoneal injection of 1 ml of 5 mM sodium periodate ($NaIO_4$) in PBS. Mice were sacrificed 24 h later and the peritoneal exudate collected by lavage with chilled PBS (5 ml/mouse). The number of macrophages present was quantified by flow cytometry using Ab specifically detecting F4/80 cell surface antigen. Values represent mean values±SEM for 5 mice in each treatment group.

These results show that Slit2 prevents monocyte migration towards different inflammatory cues, and is useful to prevent inflammation associated with atherogenesis and in-stent restenosis.

Slit2 Inhibits Monocyte Adhesion to Activated Vascular Endothelial Cells.

Figure 7A:
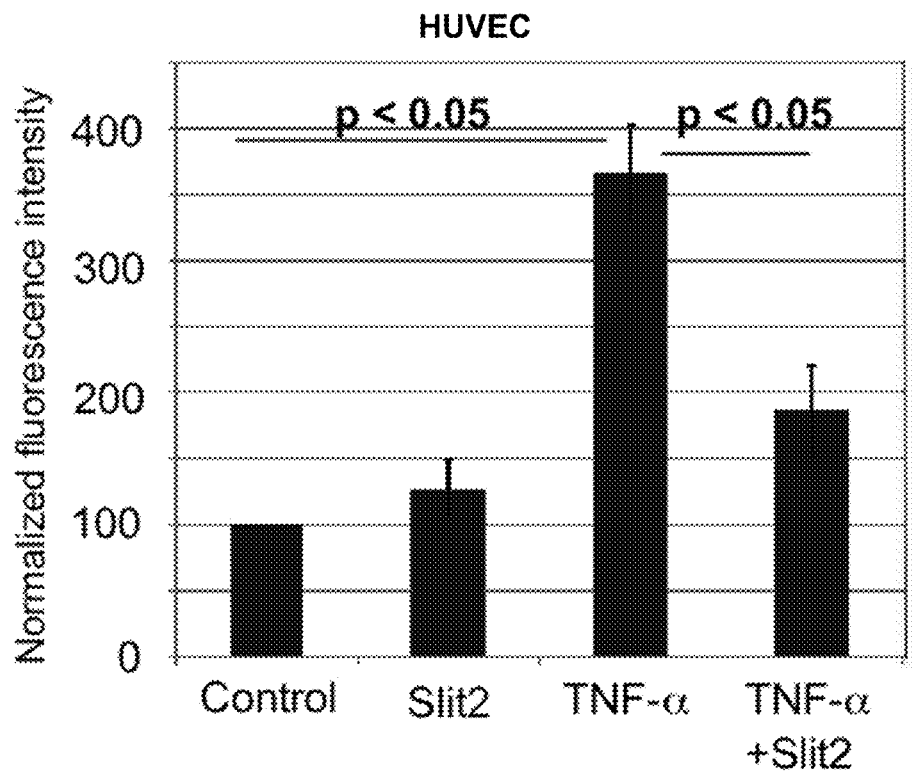
FIG. 7 shows Slit2 inhibits monocyte adhesion to primary vascular endothelial cells. A) Bar graph analysis of adhesion assay using human umbilical vein endothelial cells (HUVEC) stimulated with TNF-α (100 U/mL) to upregulate expression of adhesion molecules on the cell surface. Human THP-1 monocytic cells were labeled with calcein and incubated with activated HUVEC for 30 mins. at 37° C. Some samples were pre-incubated with Slit2 (1.5 µg/mL) prior to performing adhesion assays. B) Adhesion assays were performed as in A) using human aortic endothelial cells (HAEC). Values represent mean values±SEM for 3 separate experiments.
Figure 7B:
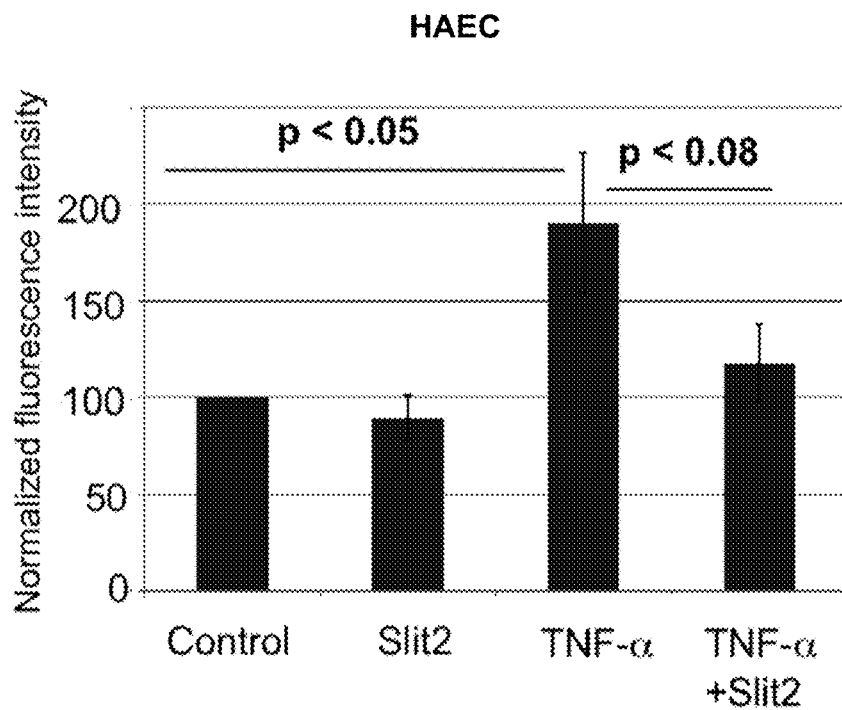

Once circulating monocytes are recruited to injured blood vessels, they firmly adhere to the inflamed endothelium before diapedesing across the endothelial wall. It was found that Slit2 inhibits monocyte adhesion to activated primary human vascular endothelial cells. Referring to FIG. 7: A) Human umbilical vein endothelial cells (HUVEC) were grown to confluence and stimulated with TNF-α (100 U/ml) for 4 h to upregulate expression of adhesion molecules on the cell surface. Human THP-1 monocytic cells were labeled with calcein and incubated with activated HUVEC for 30 min at 37° C. In some wells, THP-1 cells were pre-incubated with Slit2 (1.5 μg/ml) prior to performing adhesion assays. Non-adherent THP-1 cells were washed away and the number of adherent cells quantified using a fluorescence plate reader. Values represent mean values±SEM for 3 separate experiments. B) Adhesion assays were performed as in (A), using primary human aortic endothelial cells (HAEC) instead of HUVEC. Values represent mean values±SEM for 3 separate experiments.

This demonstrates that Slit2 inhibits not just cell migration, but also cell adhesion.

Slit2 does not Directly Suppress Other Immune Functions of Leukocytes.

Figure 8A:
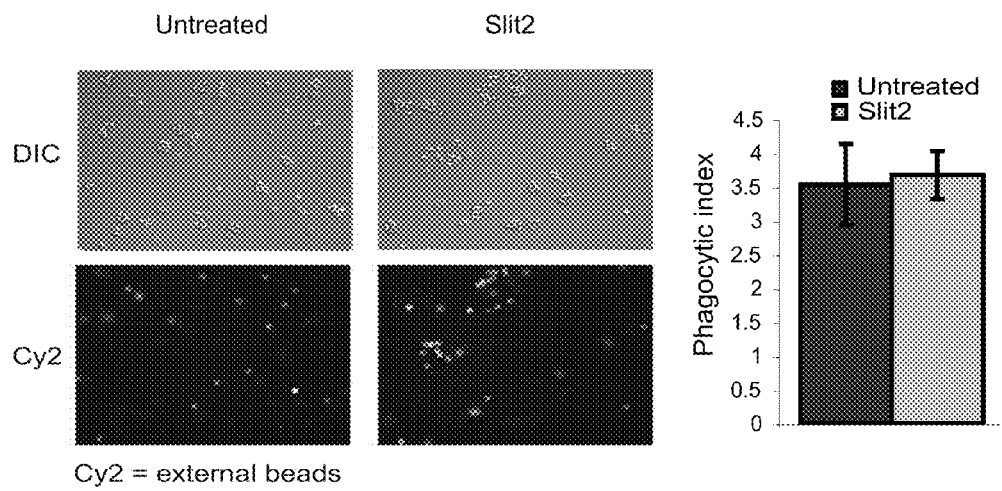
FIG. 8 shows Slit2 does not dampen other functions of leukocytes. A) Microscope images of human neutrophils rapidly centrifuged with IgG-opsonized latex beads to initiate phagocytosis and pipetted onto fibronectin-coated coverslips. Phagocytosis was allowed to continue for 10 mins. at 37° C., then beads were labeled with anti-human-Cy2 secondary Ab. Left panel, representative images of neutrophils performing IgG-mediated phagocytosis in the presence or absence of Slit2. Right panel shows Slit2 had no effect on the phagocytic index (# ingested particles/# cells). Values represent mean values±SEM for 3 separate experiments. B) Phagocytosis experiments were performed as in A) using murine RAW264.7 macrophages. C) Analysis of superoxide-inhibitable reduction of cytochrome c to assess superoxide production in human neutrophils. Cells were stimulated with fMLP or PMA (positive control) and cytochrome c reduction was measured for 20 mins. Left panel, curves depicting superoxide production in neutrophils incubated with fMLP and control medium or Slit2. Right panel, graph depicting the rate of superoxide production over 20 mins. Data represent mean values±SEM for 3 separate experiments (*p<0.02).
Figure 8B:
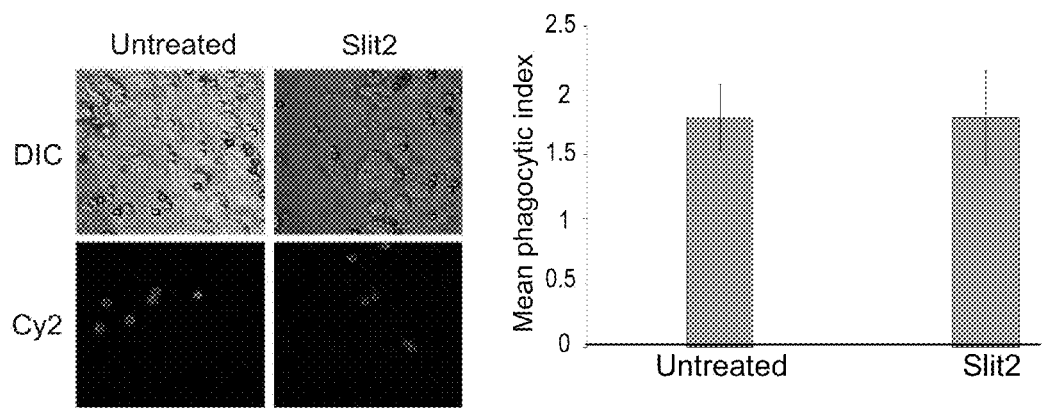
Figure 8C:
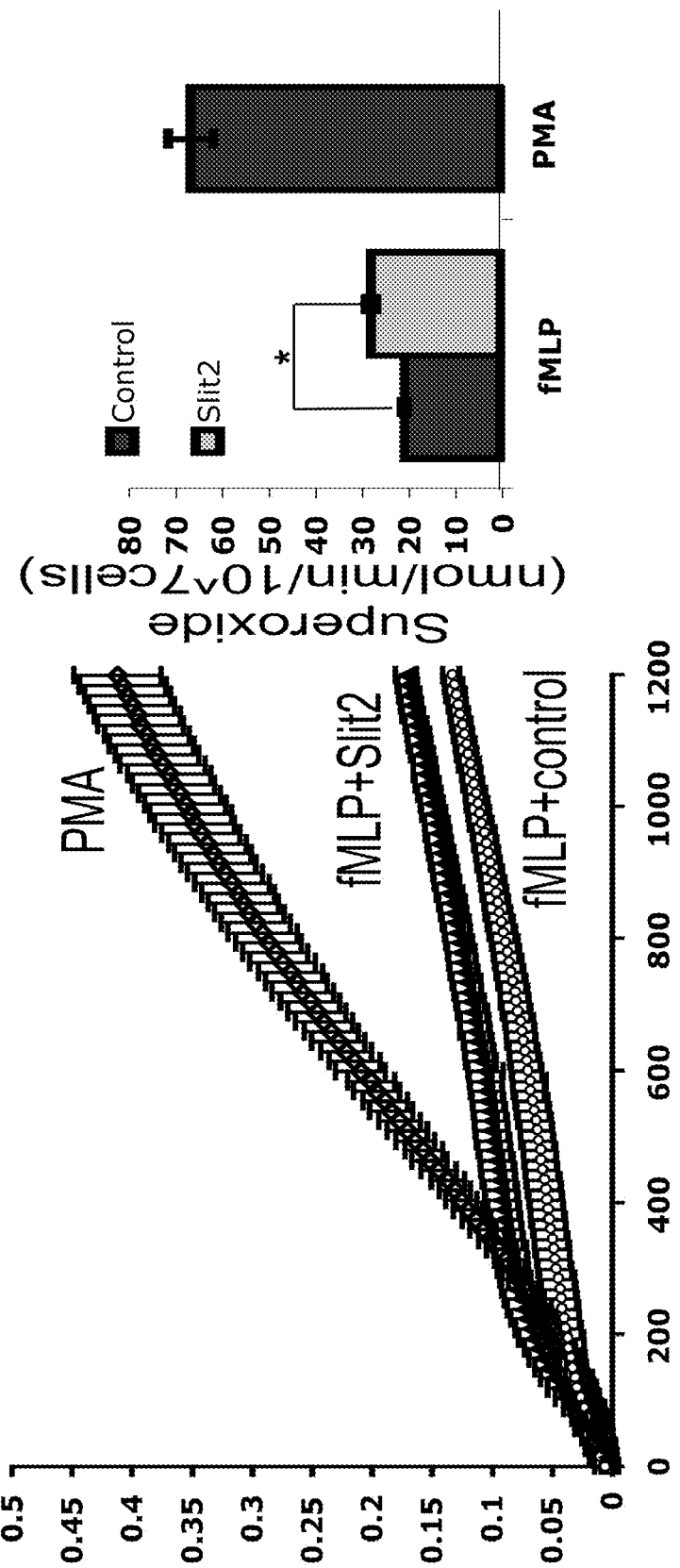

Since Rac and Cdc42 are involved in phagocytosis and superoxide production, it was tested whether Slit2 also affects these leukocyte immune functions. Slit2 did not inhibit phagocytosis by human neutrophils or mouse macrophages of opsonized particles and Slit2 did not inhibit superoxide production by neutrophils. Referring to FIG. 8: A) Human neutrophils were rapidly centrifuged with IgG-opsonized latex beads to initiate phagocytosis and pipetted onto fibronectin-coated cover slips. Phagocytosis was allowed to take place for 10 min at 37° C., after which external beads were labeled with anti-human-Cy2 secondary Ab. Cells were washed, fixed, and a Leica deconvolution microscope used to image at least 10 random fields. Left panel, representative images of neutrophils performing IgG-mediated phagocytosis in the presence or absence of Slit2. Right panel, Slit2 had no effect on the phagocytic index (# ingested particles/# cells). Values represent mean values±SEM for 3 separate experiments. B) Phagocytosis experiments were performed as in A) using murine RAW264.7 macrophages. Again, Slit2 had no effect on IgG-mediated phagocytosis. C) In human neutrophils, superoxide production was assessed by analyzing the superoxide-inhibitable reduction of cytochrome c. In the presence of control medium or Slit2, neutrophils were placed into wells containing cytochrome c±SOD and warmed to 37° C. for 3 min. A spectrometer was used to measure absorbance at 550 nm for 3 min to confirm cells were unstimulated. Cells were then stimulated with fMLP or PMA (as a positive control) and cytochrome c reduction was measured for 20 min. Left panel, curves depicting superoxide production in neutrophils incubated with fMLP and control medium or Slit2. Right panel, graph depicting the rate of superoxide production over 20 min. Data represent mean values±SEM for 3 separate experiments. *$p<0.02$.

These data demonstrate that Slit2 does not have direct immunomodulatory effects on immune cells and is useful as a therapeutic to prevent localized inflammation.

Slit2 Inhibits VSMC Migration.

In atherogenesis and in-stent restenosis, recruitment of VSMC from the medial layer worsens disease progression by enhancing neointimal proliferation. It was questioned whether Slit2 might also prevent this pathologic VSMC migration. It was first examined whether VSMC express Robo-1 and its downstream effector, srGAP1, using primary human aortic SMC and cultured MOVAS cells, an immortalized murine aortic SMC line (Afroze et al. 2003, You et al. 2003). Both cell types expressed Robo-1 and srGAP1. Referring to FIG. 9: A) Cell lysates were harvested from primary human aortic vascular smooth muscle cells (HAVSMC) and cultured mouse MOVAS aortic VSMC. Immunoblotting was performed using a specific anti-Robo-1 Ab that recognizes both human and murine species. B) Immunoblotting was performed as in (A) using a specific anti-srGAP1 Ab. C) Immunofluorescent labeling of murine MOVAS cells with anti-srGAP1 primary Ab and Cy3-conjugated secondary Ab. Image represents merged immunofluorescence and DIC microscopic images. D) Immunofluorescent labeling of primary human VSMC with anti-srGAP1 primary Ab and Cy3-conjugated secondary Ab. Image represents merged immunofluorescence and DIC microscopic images.

Figure 10A:
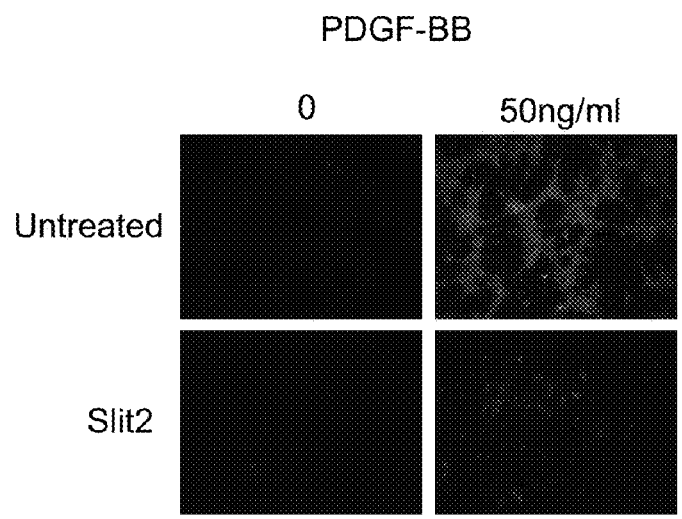
FIG. 10 shows Slit2 inhibits migration of VSMC. A) Transwell chemotaxis assays were performed using mouse MOVAS VSMCs. Cells were pre-labeled with calcein and placed in the upper chamber of a Transwell chamber. PDGF-BB (50 ng/mL) was placed in the lower chamber and plates incubated at 37 C. for 16 h. In parallel assays, cells were also exposed to purified Slit2 (4.5 mg/mL). Cells that migrated from upper to lower chamber were visualized by microscopy. B) A fluorescent plate reader was used to quantify the number of cells which migrated to the lower chamber. Values represent mean values±SEM from 3 independent experiments.
Figure 10B:
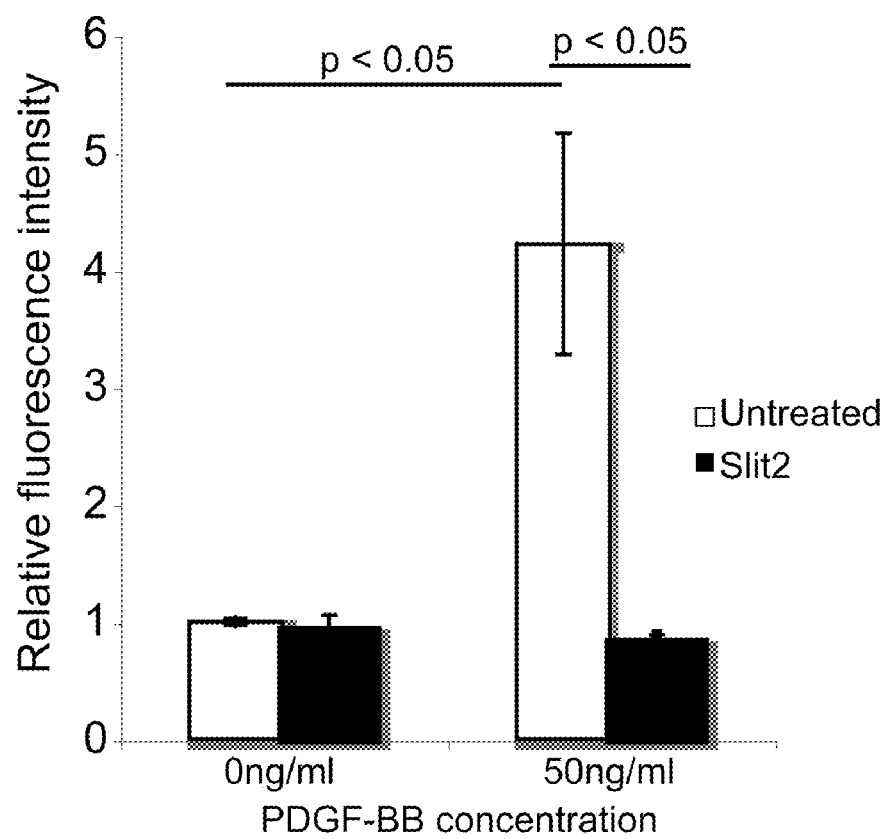

Transwell assays were performed to test the effects of Slit2 on migration of MOVAS VSMC. Slit2 effectively inhibited VSMC chemotaxis towards the chemoattractant, PDGF-BB. Referring to FIG. 10: A) Transwell chemotaxis assays were performed using mouse MOVAS VSMC. MOVAS cells were pre-labeled with calcein and placed in the upper chamber of a Transwell chamber. PDGF-BB (50 ng/ml) was placed in the lower chamber, and plates were incubated at 37° C. for 16 h. In parallel assays, cells were also exposed to purified Slit2 (4.5 μg/ml). Cells which migrated from the upper to the lower chamber were visualized by microscopy. B) A fluorescent plate reader was used to quantify the number of cells which migrated to the lower chamber. Values represent mean values±SEM from 3 independent experiments.

These results show that Slit2 is useful to prevent neointimal proliferation in diseased native vessels and in vascular stents.
Slit2 can be Used In Vivo to Prevent Localized Inflammation.

Figure 11A:
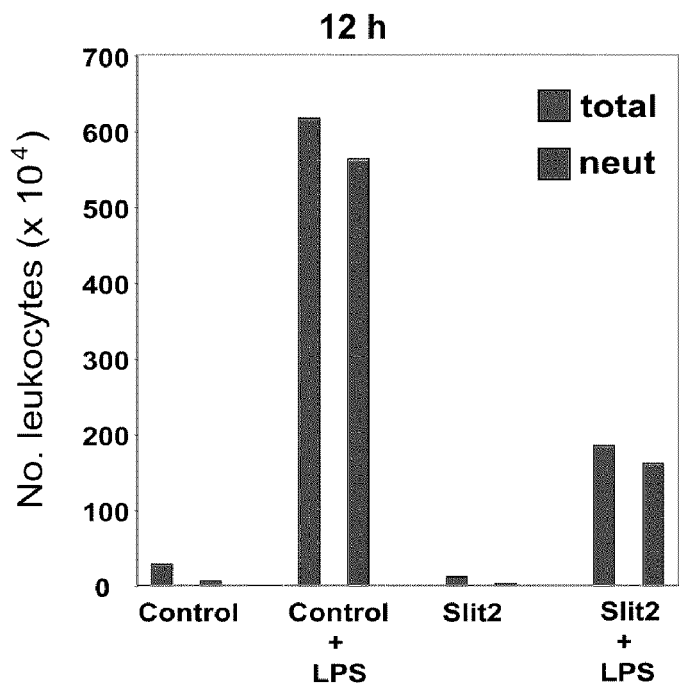
FIG. 11 shows Slit2 inhibits leukocyte migration in vivo. Slit2 (100 ng) was instilled intracheally into the lungs of adult mice and one hour later, lipopolysaccharide (LPS; 30 µg/kg in 200 µL saline) was delivered to the lungs. After 12 h (A) or 24 h (B), bronchoalveolar lavage was performed using 2 mL of sterile saline. Cytospin was performed, cells were fixed on glass slids, and the total number of inflammatory cells as well as the number of neutrophils present were determined. Mean values for two mice per treatment group.
Figure 11B:
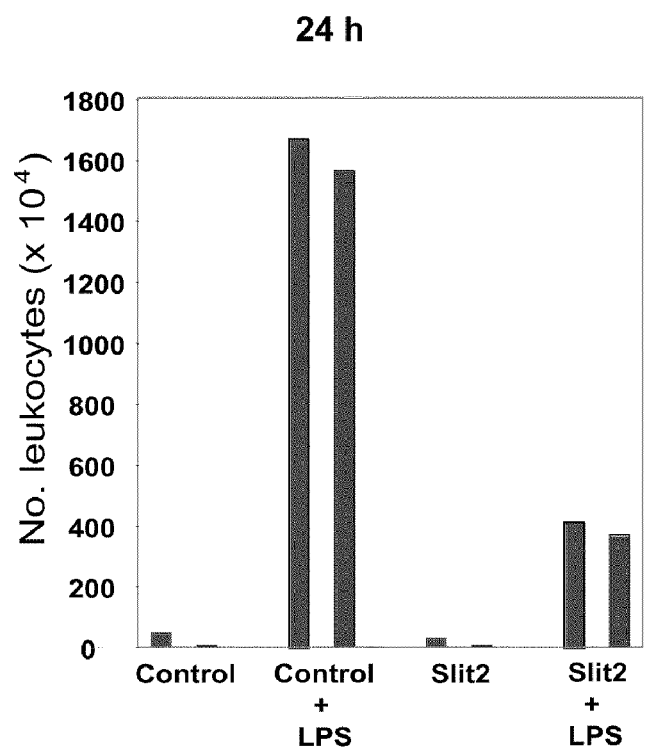

Slit2 was previously tested in mouse models of peritoneal inflammation and it was found to be effective (refer to FIG. 6). In a mouse model of acute lung injury, it was found that Slit2 decreased infiltration of inflammatory cells into the lung by over 70%. Referring to FIG. 11: A and B) Slit2 (100 ng) was instilled intratracheally into the lungs of adult mice. One hour later, lipopolysaccharide (LPS; 30 µg/kg in 200 µl saline) was delivered intratracheally to the lungs. After 12 h (A) or 24 h (B), bronchoalveolar lavage was performed using 2 ml of sterile saline. Cytospin was performed, cells were fixed on glass slides, and the total number of inflammatory cells as well as the number of neutrophils present was determined. At both 12 h and 24 h timepoints, Slit2 significantly inhibited recruitment of inflammatory cells, particularly neutrophils, to the lungs. Mean values for 2 mice per treatment group.

Figure 12A:
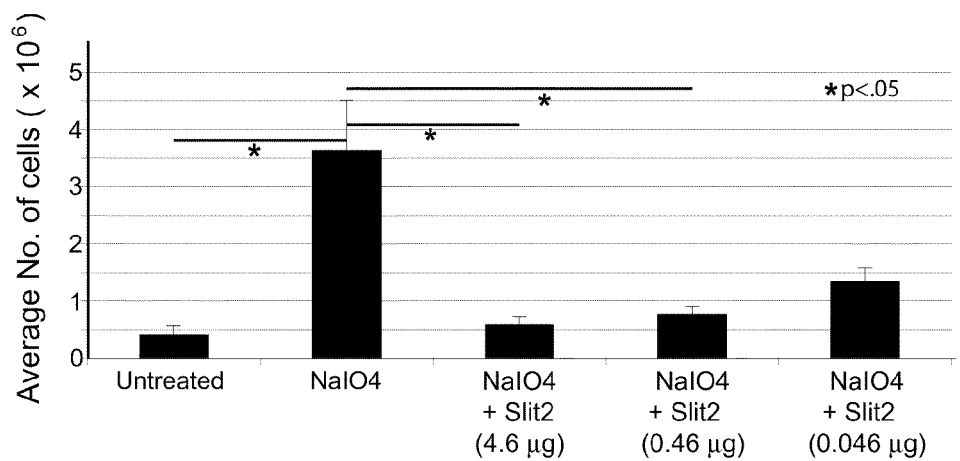
FIG. 12 shows optimizing the dosing of Slit2 administered in vivo. A) In CD1 mice, sodium periodate ($NaIO_4$)-induced peritonitis was induced as described above. Slit2 was administered intravenously by tail vein injection at the indicated doses, 1 day prior to induction of peritonitis. Twenty-four hours after induction of peritonitis, peritoneal lavage was performed and the number of macrophages infiltrating the peritoneal cavity was determined by counting and flow cytometry using Ab detecting the macrophage surface marker, F4/80. Mean values±SEM for 3 mice per group *p<0.05 vs. $NaIO_4$. B) Experiments were performed as in A) using a dose of Slit2 (1.8 µg) administered at the indicated times prior to induction of peritonitis. The number of macrophages infiltrating the peritoneal cavity was determined as in A). Mean values±SEM for 3 mice per group. *p<0.001; x p<0.01.
Figure 12B:
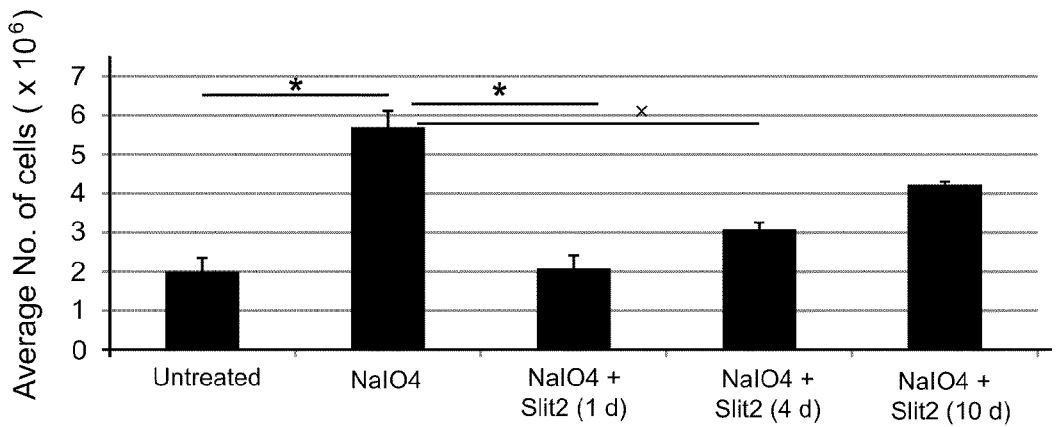
Figure 13A:
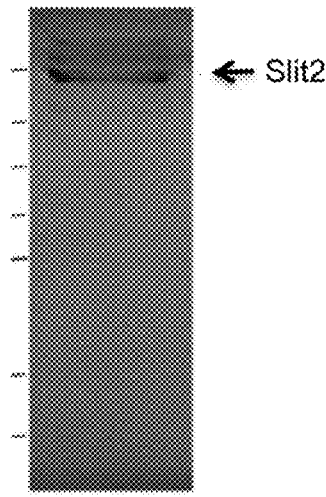
FIG. 13 shows recombinant hSlit2 purified by size-exclusion chromatography and cobalt affinity chromatography. Conditioned medium was harvested from HEK293-hSlit2-myc cells and control HEK293 cells. Using size-exclusion chromatography, fractionated samples were collected and were run in 8% SDS-PAGE. A) Representative gel for a sample from pooled fractions subjected to silver staining. B) Representative gel transferred to a PVDF membrane and subjected to immunoblot analysis using monoclonal anti-myc Ab. For larger scale preparation of Slit2, conditioned medium was harvested from HEK293-EBNA1 cells transfected with pTT28-Slit2 expression plasmid. Slit2 secreted into the medium was purified by immobilized metal-affinity chromatography using Fractogel®-cobalt columns. Samples were desalted and immunoblotting performed. Proteins were resolved on reducing NuPAGE 4-12% Bis-Tris gradient gels and transferred to nitrocellulose membranes. C) Representative membrane stained with Ponceau red solution. D) Representative membrane probed with anti-polyHis-HRP Ab (1-harvested medium, 5 days post-transfection; 2-IMAC flow-through; 3-wash 1; 4-wash 2; 5-pooled eluted fractions from Fractogel®-cobalt column).
Figure 13B:
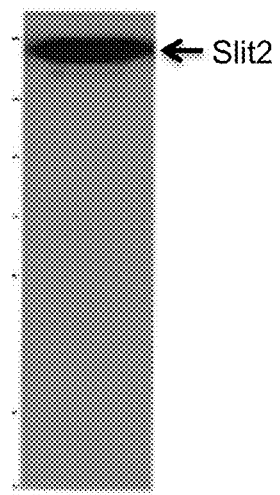
Figure 13C:
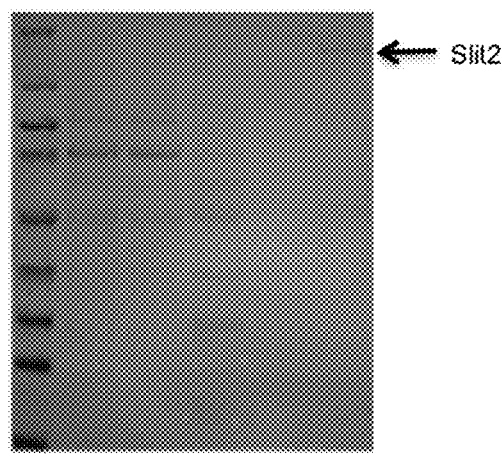
Figure 13D:
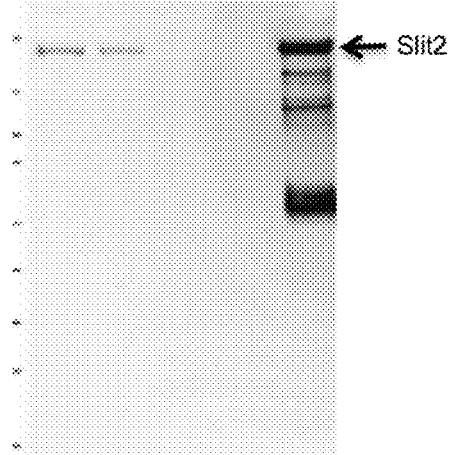

The dose and dosing interval of Slit2 administered in vivo was also optimized. Doses as low as 0.46 µg were effective. In time-course experiments, Slit2 administered even 4 days prior to induction of peritonitis proved efficacious. Referring to FIG. 12: A) In CD1 mice, sodium periodate ($NaIO_4$)-induced peritonitis was induced as described in FIG. 6. Slit2 was administered intravenously by tail vein injection at the indicated doses, 1 day prior to induction of peritonitis. 24 h after induction of peritonitis, peritoneal lavage was peformed and the number of macrophages infiltrating the peritoneal cavity was determined by counting and flow cytometry, using Ab detecting the macrophage surface marker, F4/80. Mean values±SEM for 3 mice per group. *$p<0.05$ vs $NaIO_4$. B) Experiments were performed as in (A), using a dose of Slit2 (1.8 µg) administered at the indicated times prior to induction of peritonitis. The number of macrophages infiltrating the peritoneal cavity was determined as in (A). Mean values±SEM for 3 mice per group. *$p<0.001$; x $p<0.01$.
Truncated N-Terminal Slit2 Effectively Prevents Leukocyte Chemotaxis.

Recombinant hSlit2 was purified by size-exclusion chromatography and cobalt-affinity chromatography to use in tests to compare the efficacy of full-length Slit2 protein to the N-terminal truncated Slit2 protein. Referring to FIG. 13: A-B, Conditioned medium was harvested from HEK293-hSlit2-myc cells and control HEK-293 cells as outlined in detail in (Tole et al., 2009). Using size-exclusion chromatography, fractionated samples were collected and were run in 8% SDS-PAGE. A. Representative gel for a sample from pooled fractions was silver stained. B. Representative gel, transferred to a PVDF membrane and immunoblotting performed using monoclonal anti-myc Ab. C-D. For larger-scale preparation of Slit2, conditioned medium was harvested from HEK293-EBNA1 cells transfected with pTT28-Slit2 expression plasmid, as described in (Tole et al., 2009). Slit2 secreted into the medium was purified by immobilized metal-affinity chromatography using Fractogel®-cobalt columns. Samples were desalted and immunoblotting performed. Proteins were resolved on reducing NuPAGE 4-12% Bis-Tris gradient gels, and transferred to nitrocellulose membranes. C. Representative membrane, stained with Ponceau red solution. D. Representative membrane, probed with anti-polyHis-HRP Ab. For C and D, lanes are marked as follows: 1) harvested medium 5 days post-transfection; 2) IMAC flow-through; 3) Wash 1; 4) Wash 2; 5) pooled eluted fractions from Fractogel-cobalt column. Reproduced from *J Leukoc Biol* (2009) 86: 1403-1415.

Figure 14A:
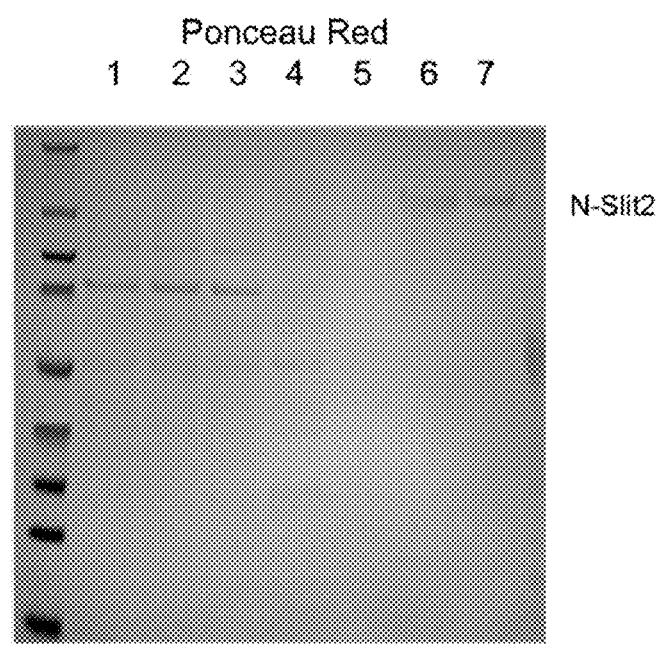
FIG. 14 shows purification of truncated N-terminal Slit2 (N-Slit2). A DNA expression plasmid encoding N-Slit2 was expressed in HEK293-EBNA cells and purified as described above. A) Representative membrane stained with Ponceau red solution. B) Membrane probed with anti-polyHis-HRP antibody (1-supernatant harvested on day 5; 2-feed after 1 night at 4° C. and 0.45 µm filtration; 3-flow-through; 4-wash 1; 5-wash 2; 6-elution from Fractogel®-cobalt column (pooled fractions); 7-desalted (pooled fractions).
Figure 14B:
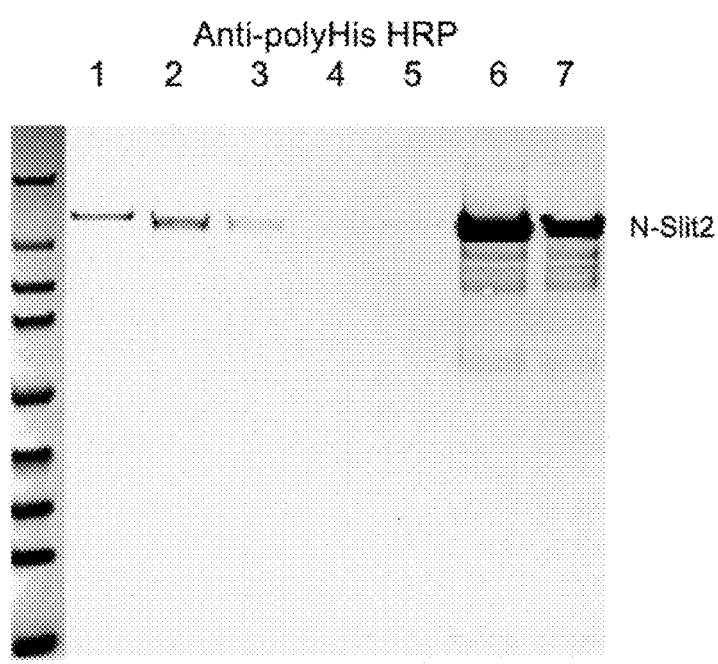

An expression plasmid encoding a smaller N-terminal truncated Slit2 protein (N-Slit2) was generated which contains the leucine rich region necessary for binding to the Robo-1 receptor and for downstream signal transduction. Referring to FIG. 14: Purification of truncated N-terminal Slit2 (N-Slit2): A DNA expression plasmid encoding N-Slit2 was expressed in HEK293-EBNA cells and purified as described in FIG. 13. A) Representative membrane stained with Ponceau red solution. B) Membrane probed with anti-polyHis-HRP antibody. For A) and B) lanes are marked as follows: 1) Supernatant harvested on Day 5, 2) feed (after 1 night at 4° C. and 0.45 µm filtration, 3) flow-through, 4) wash 1, 5) wash 2, 6) elution from Fractogel®-Cobalt column (pooled fractions), 7) desalted (pooled fractions).

Figure 15:
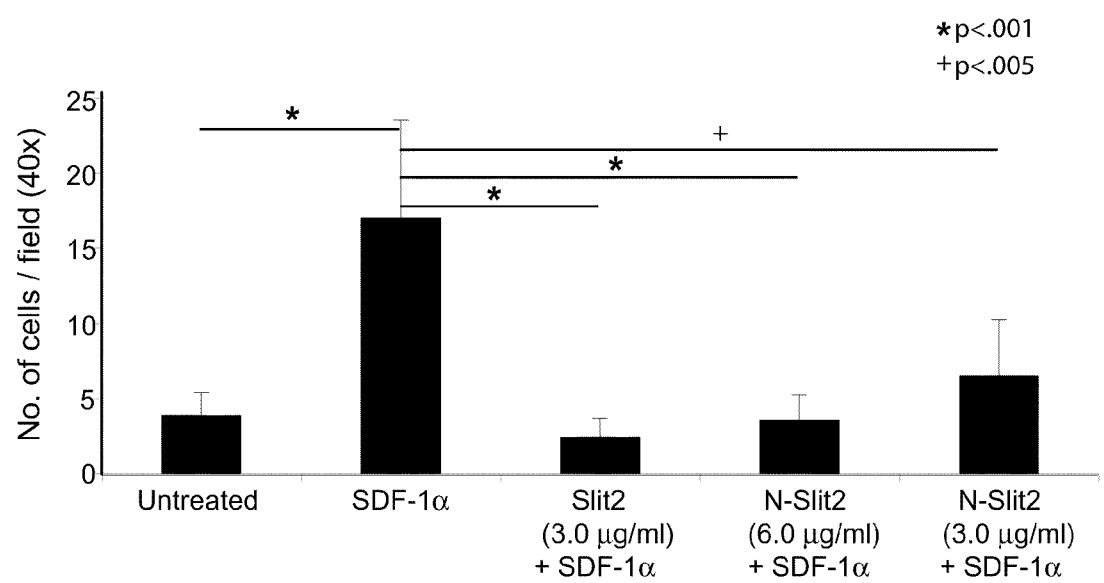
FIG. 15 shows truncated N-terminal Slit2 effectively prevents leukocyte chemotaxis. N-Slit2 was synthesized and purified and efficacy tested using Transwell chemotaxis assays as described above. N-Slit2 inhibited chemotaxis of THP-1 monocyte cells at a concentration of the same order of magnitude as effective concentrations of the full-length protein. Mean values±SEM for 3 separate experiments.
Figure 17A:
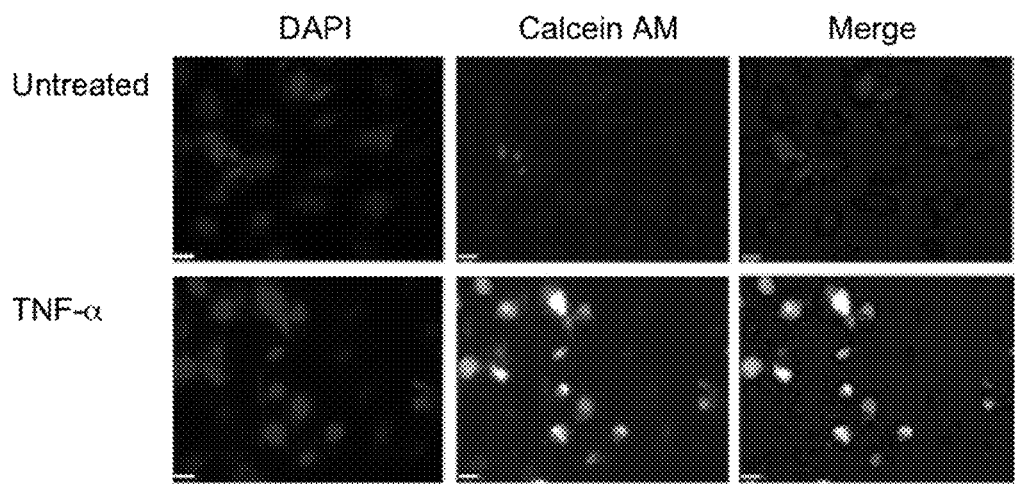
FIG. 17 shows Slit2 inhibits monocyte adhesion to activated vascular endothelial cells on coronary artery stents. A) Coronary artery stent stainless steel (316L) disks were coated with fibronectin, then seeded with HAECs. Cells were grown to confluence on the disks and stimulated with TNF-α (20 ng/mL) for 4 h. THP-1 cells were pre-labeled with calcein-AM for visualization. Adhesion assays were performed by incubating THP-1 cells with HAEC-coated metal disks at 37° C. for 3 h. Non-adherent THP-1 cells were removed by washing and the number of adherent cells assessed using a fluorescent plate reader. To confirm the metal disks were covered with a confluent layer of HAECs, at the end of each experiment, cells on each disk were labeled with DAPI for visualization of nuclei. B) Graph depicts mean values from two separate experiments. C) Adhesion experiments were performed as in A), after pre-incubation of THP-1 cells with Slit2 (4.5 µg/mL) for 10 mins. At the end of the assays, cells were lysed and fluorescence intensity measured using a plate reader. A standard curve was generated by measuring fluorescence intensity of known number of THP-1 cells labeled with calcein. Triplicate results from a single experiment are shown.
Figure 17B:
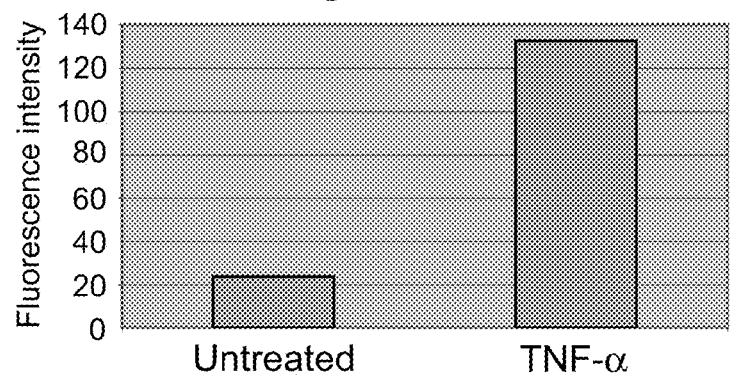
Figure 17C:
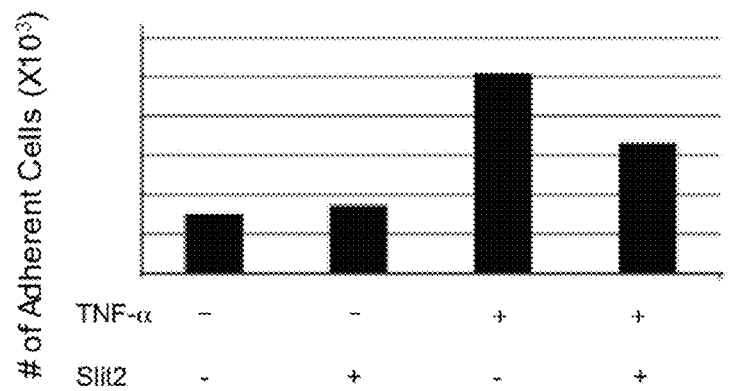

Truncated N-terminal Slit2 effectively prevents leukocyte chemotaxis. Referring to FIG. 15: N-Slit2 was synthesized and purified, and its efficacy tested using Transwell chemotaxis assays described in FIG. 5. N-Slit2 inhibited chemotaxis of THP-1 monocytic cells at a concentration of the same order of magnitude as effective concentrations of the full-length protein. Mean values±SEM for 3 separate experiments.
Slit2 Inhibits Monocyte Adhesion to Activated Vascular Endothelial Cells on Coronary Artery Stents Slit2 inhibits monocyte adhesion to activated vascular endothelial cells on coronary artery stents. Referring to FIG. 17: A) Coronary artery stent stainless steel (316L) disks were coated with fibronectin, then seeded with human aortic endothelial cells (HAEC). HAEC were grown to confluence on the stainless steel disks and stimulated with TNF-α (20 ng/ml) for 4 h. THP-1 human monocytic cells were pre-labeled with calcein-AM in order to visualize them. Adhesion assays were performed by incubating THP-1 cells with HAEC-coated metal disks at 37° C. for 3 h. Non-adherent THP-1 cells were removed by washing and the number of adherent cells assessed using a fluorescent plate reader. To confirm that metal disks were covered with a confluent later of HAEC, at the end of each experiment, cells on each disk were labeled with DAPI to visualize nuclei. B) Graph depicts mean values from 2 separate experiments. C) Adhesion experiments were performed as in (A), after pre-incubation of THP-1 cells with Slit2 (4.5 µg/ml) for 10 min. At the end of the assays, cells were lysed and fluorescence intensity measured using a plate reader. A standard curve was generated by measuring fluorescence intensity of known numbers of THP-1 cells labeled with calcein. Triplicate results from a single experiment are shown.

This demonstrates that Slit2 is useful for inhibiting inflammation causing re-stenosis of vascular stents.

Example 2

The Cell Motility Modulator Slit2 is a Potent Inhibitor of Platelet Function

Results:
Platelets Express Robo-1 on their Surface

Figure 18A:
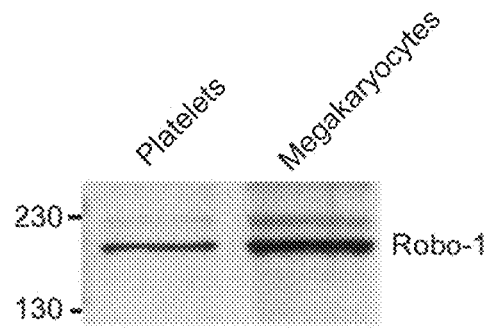
FIG. 18 shows human and murine platelets express Robo-1 on the cell surface. (a) Cell lysates from normal human platelets and megakaryocytes were subjected to immunoblotting and probed with anti-Robo-1 primary antibody and HRP-conjugated anti-rabbit IgG. (b) Washed human platelets were fixed, permeabilized and labeled with anti-Robo-1 antibody followed by Alexa Fluor 488-conjugated anti-rabbit antibody. Image acquisition was performed using a Leica DMIRE2 spinning disc confocal microscope at 100× magnification. Scale bar represents 4 µm. (c) Platelets were isolated from mouse peripheral blood, fixed, permeabilized and incubated with anti-Robo-1 antibody followed by Alexa Fluor 568-conjugated rabbit antibody. Image acquisition was performed using a Leica DMIRE2 spinning disc confocal microscope at 63× magnification. Scale bar represents 4 µm. (d) Murine platelets were incubated with anti-CD62P detected by Alexa Fluor 488-conjugated goat antibody and anti-Robo-1 detected using Alexa Fluor 568-conjugated rabbit antibody. Scale bar represents 2 µm. Right panel, image in the YZ plane (scale bar 1.2 µm).
Figure 18B:
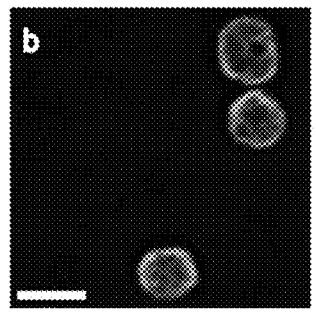
Figure 18C:
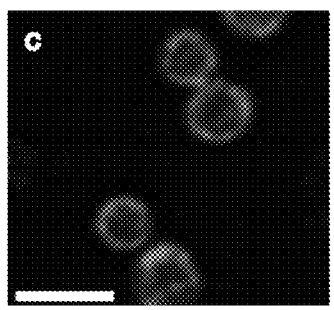
Figure 18D:
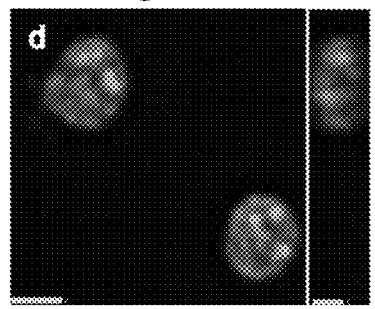

Immunoblot analysis of cell lysates detected expression of the Slit2 receptor, Robo-1, in human platelets and their precursor megakaryocytes (FIG. 18*a*). Laser immunofluorescence confocal microscopy showed that in human and murine platelets, Robo-1 receptors localized at the cell surface (FIG. 18*b,c,d*). Localization of CD62P (P-selectin) within the interior of platelets confirmed the resting state of platelets visualized by immunofluorescence microscopy (FIG. 18*d*).

Slit2 Inhibits Spreading of Human Platelets

Figure 19A:
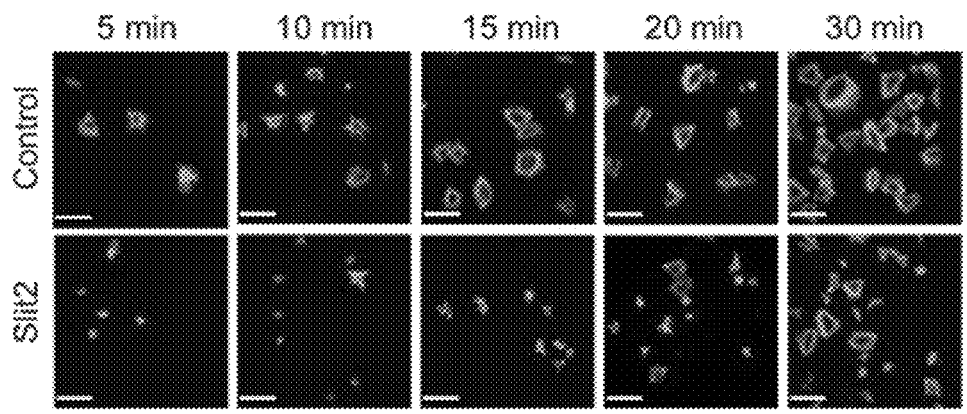
FIG. 19 shows Slit2 inhibits human platelet spreading on diverse substrates. Isolated human platelets ($10^7$/ml) were pre-incubated with Slit2 (4.5 µg/ml) or equal volume of PBS (control) for 10 min at 37° C., and dispensed onto coverslips pre-coated with fibrinogen (100 µg/ml; a and b), fibronectin (50 µg/ml; c and d), collagen (100 µg/ml; e and f), or glass (g and h) for the indicated times. (a) Platelets adherent to fibrinogen were fixed, permeabilized, incubated with Alexa Fluor 488-conjugated phalloidin, and visualized using a Leica DMIRE2 spinning disc confocal microscope. Scale bars represents 11 µm. (b) Experiments were performed as in (a). Images were acquired from 15 random fields and the surface area of platelets was quantified using Volocity™ software. Data are expressed as mean±SEM from 3-5 independent experiments. (c) Experiments were performed as in (a) using cover-slips coated with fibronectin. (d) Experiments were performed as in (c) and quantification done as described in (b). Data are expressed as mean±SEM from 3-5 independent experiments. (e) Experiments were performed as in (a) using cover-slips coated with collagen. (f) Experiments were performed as in (e) and quantification done as described in (b). (g) Experiments were performed as in (a) using uncoated glass cover-slips. (h) Experiments were performed as in (g) and quantification done as described in (b). Data are expressed as mean±SEM from 3-5 independent experiments. *, $p<0.05$; **, $p<0.01$.
Figure 19B:
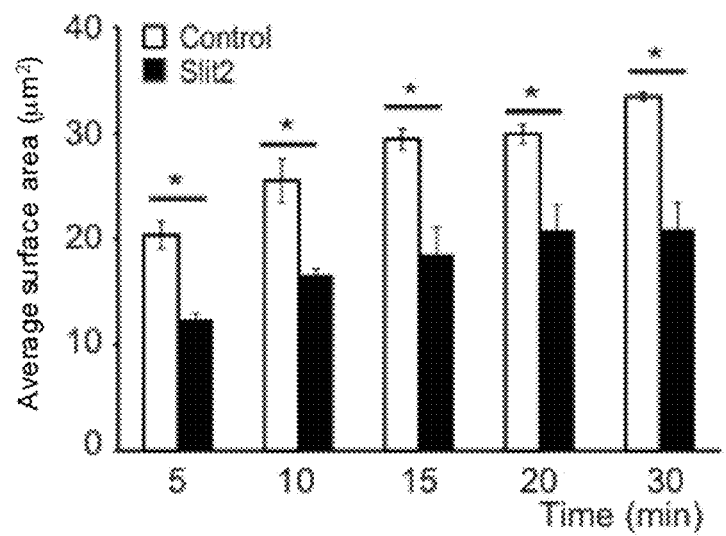

The potential effects of Slit2/Robo-1 interactions on platelet function were first examined by assessing the effects of Slit2 on adhesion and spreading of human platelets on a fibrinogen-coated surface. Untreated cells progressively spread on fibrinogen-coated cover slips during a 30 min observation period (FIG. 19a,b). In the presence of Slit2, platelet spreading was markedly decreased, with cells exhibiting short, warped filopodia and decreased formation of lamellar sheets (FIG. 19a). After 30 min, the mean platelet surface area was $20.9 \pm 2.5$ $\mu m^2$ in the presence of Slit2, significantly less than the $33.4 \pm 0.6$ $\mu m^2$ mean surface area observed for untreated cells (FIG. 19b; $p<0.05$). In real-time visualization, Slit2-treated platelets exhibited rounding of the cell body and development of dynamic and motile filopodial structures but limited formation of lamellar sheets between the filopodia. This was in sharp contrast to the smooth, fluid formation of filopodia and lamellipodia seen when Slit2 was not present.

Figure 19C:
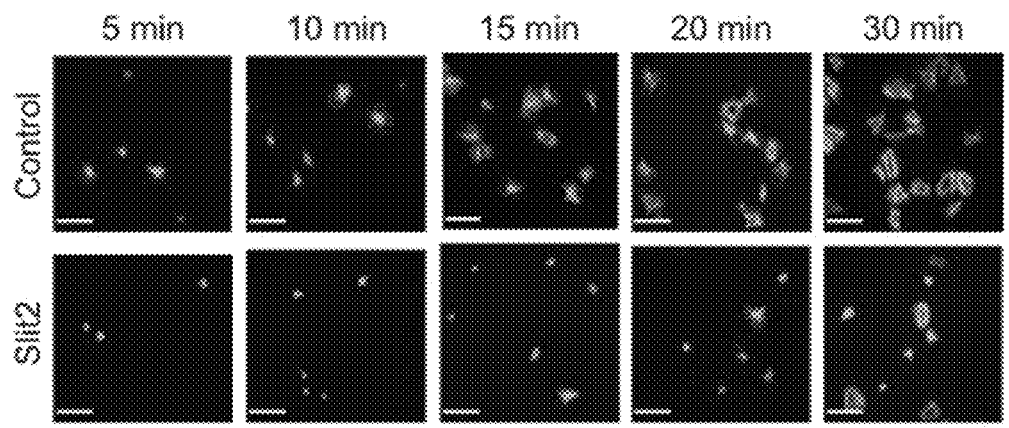
Figure 19D:
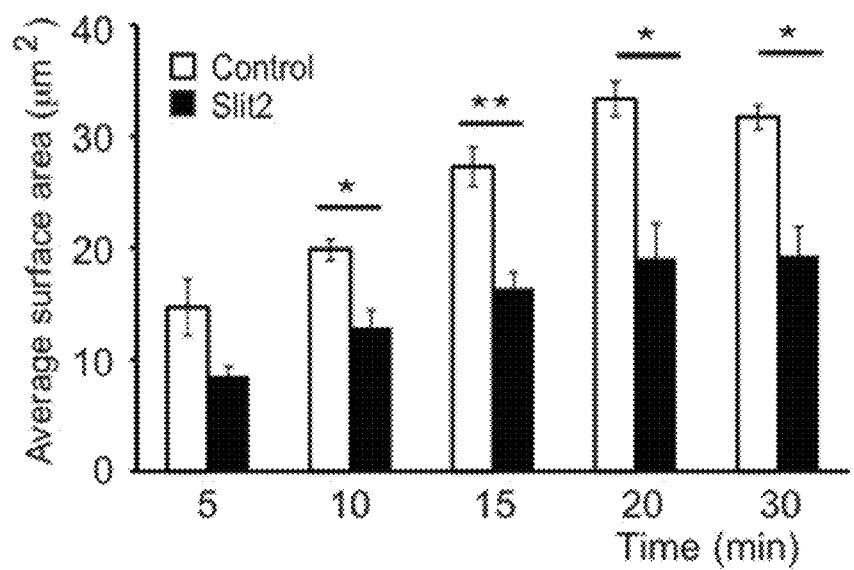
Figure 19E:
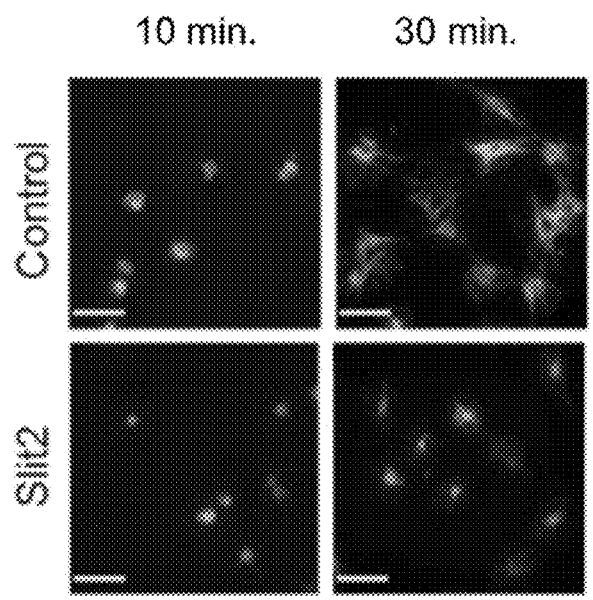
Figure 19F:
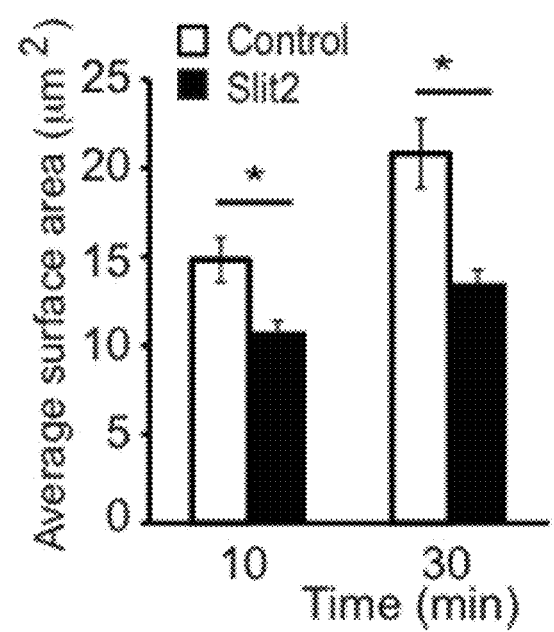
Figure 19G:
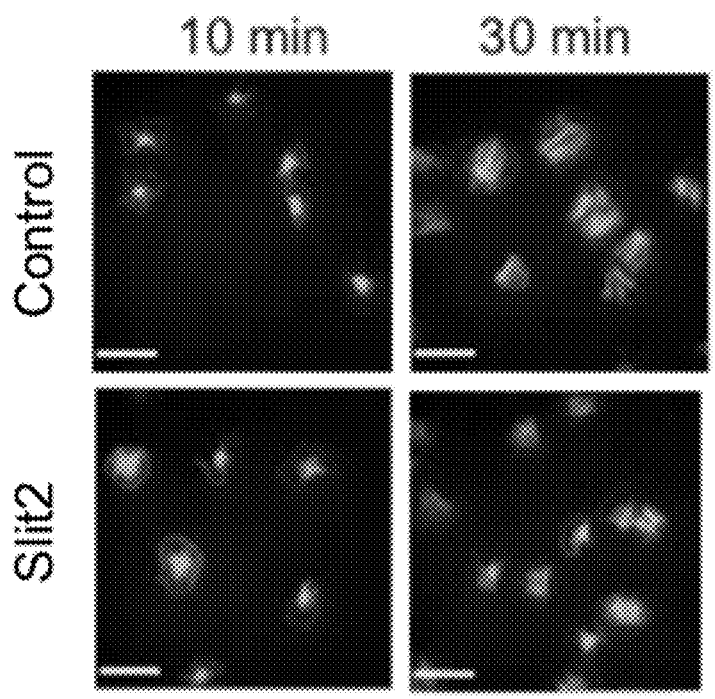
Figure 19H:
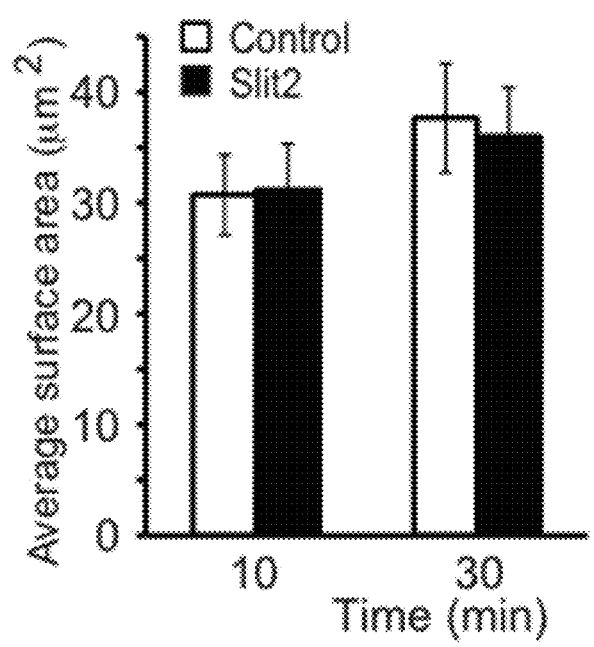

Platelet spreading on fibrinogen is mediated by cell surface GPIIb/IIIa (integrin $\alpha_{IIb}\beta_3$) receptors, while interaction with fibronectin also involves GPIc/IIa (integrin $\alpha_5\beta_1$) receptors (Ruggeri 2002; Kuijpers, Schulte et al. 2003; McCarty, Zhao et al. 2004). Platelet spreading on collagen involves GPVI and GPIa/IIa (integrin $\alpha_2\beta_1$) receptors (Moroi, Jung et al. 1996; Ruggeri 2002; Kuijpers, Schulte et al. 2003). The effects of Slit2 on platelet spreading on fibronectin and collagen were examined as described above. After 30 min, the mean surface area of platelets on fibronectin-treated cover slips was $19.3 \pm 2.6$ $\mu m^2$ in the presence of Slit2, significantly less than untreated cells ($31.7 \pm 1.8$ $\mu m^2$; FIG. 19c,d; $p<0.05$). On collagen-treated cover slips the mean surface area was $13.5 \pm 0.7$ $\mu m^2$ in the presence of Slit2, significantly less than untreated cells ($20.8 \pm 1.9$ $\mu m^2$; FIG. 19e,f; $p<0.05$). Slit2 did not affect the spreading of platelets on uncoated glass surfaces (FIG. 19g,h), indicating a specific inhibition of cell surface receptor-mediated platelet response to matrix molecules.

Slit2 Inhibits Platelet Adhesion Under Physiologic Flow Conditions

Figure 20A:
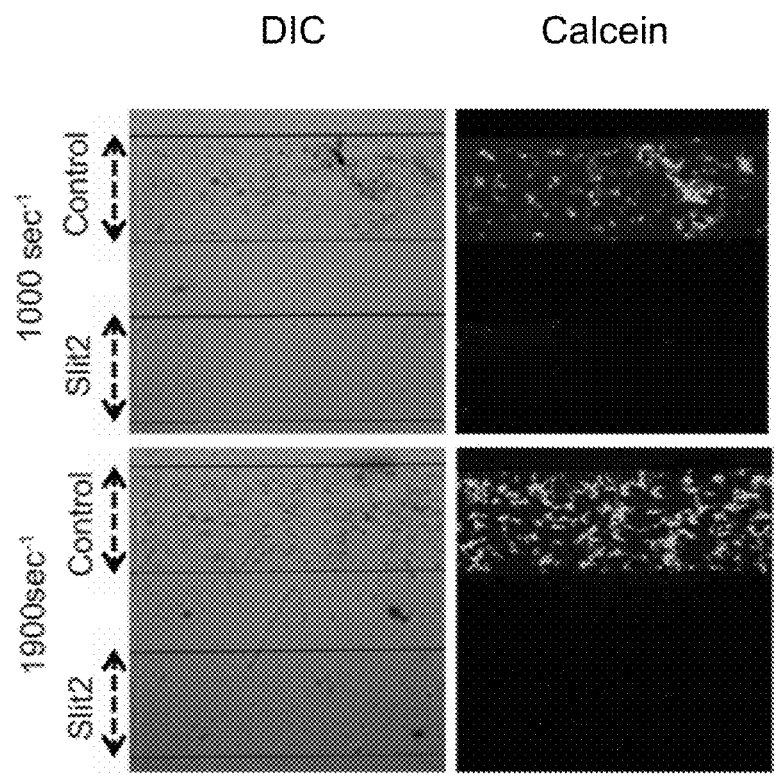
FIG. 20 shows Slit2 inhibits platelet adhesion to collagen under physiological shear flow conditions. (a) Washed human platelets ($10^7$/ml) were incubated with calcein-AM (4 µM) for 20 min and pre-incubated with Slit2 (4.5 µg/ml) or an equal volume of PBS (control) for 10 min at 37° C. Platelets were perfused over collagen-coated Bioflux™ micro-fluidic channels at constant shear rates of 1000 $sec^{-1}$ or 1900 $sec^{-1}$ for 4 min. Channels were washed with HEPES-Tyrode's buffer for 4 min at the same shear rates and images acquired by differential interface contrast (DIC) and fluorescence microscopy at 10× on a Leica DMIRE2 deconvolution microscope. The width of the channel indicated by the dashed arrows is 350 µm. Images are representative of 3-5 independent experiments. (b) Platelet adhesion to collagen-coated micro-fluidic channels was quantified using Bioflux™ 200 analysis software. Data are expressed as mean±SEM from 3-5 independent experiments. *, $p<0.05$; **, $p<0.01$.
Figure 20B:
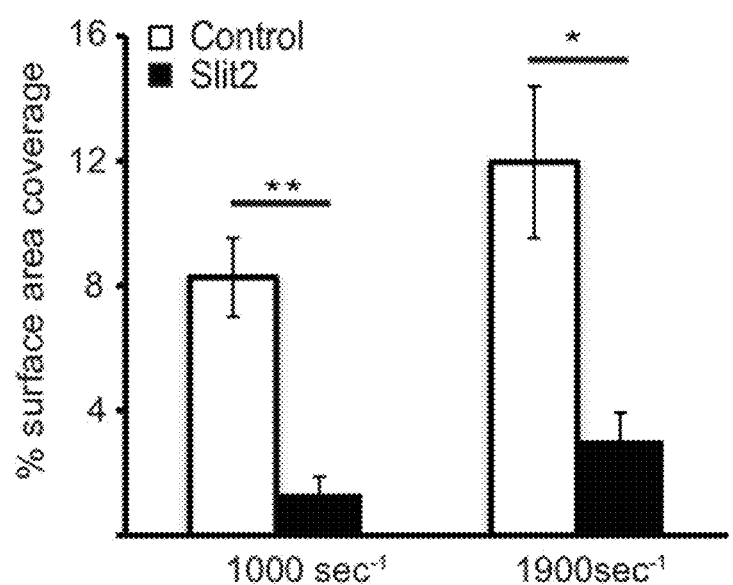
Figure 24A:
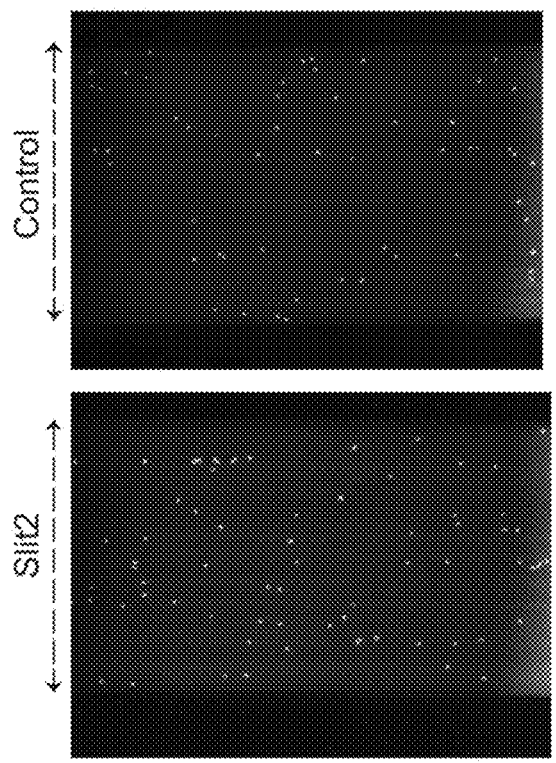
FIG. 24 shows Slit2 does not inhibit platelet adhesion to vWF under physiological shear flow conditions. (a) Washed human platelets ($3\times10^7$/ml) were incubated with calcein-AM (4 µM) for 20 min and pre-incubated with Slit2 (4.5 µg/ml) or an equal volume of PBS (control) for 10 min at 37° C. Platelets were perfused over vWF-coated Bioflux™ micro-fluidic channels at constant shear rates of 1000 $sec^{-1}$ for 4 min. Images were acquired at 20× on a Nikon TE2000 inverted microscope. The width of the channel indicated by the dashed arrows is 350 µm. Images are representative of 3 independent experiments. (b) Mean number of cells counted per 20× field±SEM; n=3.
Figure 24B:
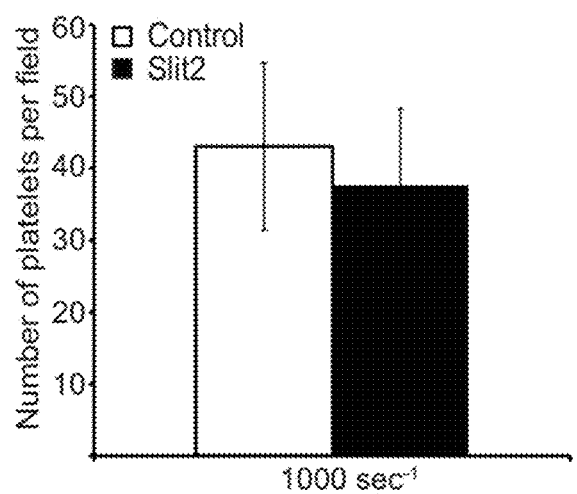

Collagen is the first potentially activating substrate that platelets typically encounter within an injured blood vessel, and their response is sensitive to shear flow conditions. Bioflux microfluidic channels coated with collagen were used to mimic hydrodynamic flow conditions that would be encountered by platelets within the arterial circulation (Kroll 2001). For untreated cells, the average surface area covered by platelets after 4 min was $8.3 \pm 1.3\%$ at shear flow rates of $1000$ $sec^{-1}$ (FIG. 20a,b); for cells treated with Slit2, this area markedly decreased to $1.3 \pm 0.5\%$ (FIG. 20a,b; $p<0.01$). At shear flow rates of $1900$ $sec^{-1}$, comparable to hydrodynamic conditions encountered within large arteries, the average platelet surface area coverage decreased four-fold from $12.0 \pm 2.4\%$ to $3.1 \pm 0.9\%$ with Slit2 treatment (FIG. 20a,b; $p<0.05$). Because Slit2 is a large glycoprotein, the possibility that it may directly bind to GP1b$\alpha$ on the surface of platelets was considered, thereby blocking steric interactions between GP1 b$\alpha$ and von Willebrand factor (vWF) or collagen. To examine this possibility, the effects of Slit2 on platelet adhesion to vWF was tested. Slit2 did not inhibit platelet adhesion to vWF, suggesting that the observed effects of Slit2 on platelet adhesion to collagen did not occur by direct binding of Slit2 to the GP1 b$\alpha$ receptor (FIG. 24).

Slit2 does not Affect Rac1 and Cdc42 Activation During Platelet Spreading

Figure 21A:
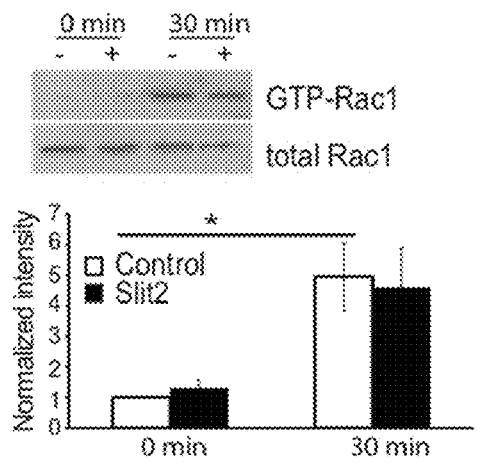
FIG. 21 shows Slit2 inhibits activation of Akt but not Rac1, Cdc42, Erk, or p38 MAPK. (a-e) Washed human platelets were pre-incubated with Slit2 (4.5 µg/ml) or an equal volume of PBS (control) for 10 min at 37° C., and allowed to spread on fibrinogen-coated wells for 30 min. Wells were washed with PBS to remove non-adherent platelets, and cell lysates harvested from adherent platelets. (a) Cell lysates were incubated with GST-PBD glutathione beads to immunoprecipitate activated Rac1, and immunoblotting performed using anti-Rac1 antibody. Lower panel, band intensities of GTP-Rac1 normalized to total Rac1 expressed as mean±SEM from 5 independent experiments. (b) Cell lysates were incubated with GST-PBD glutathione beads to immunoprecipitate activated Cdc42, and immunoblotting performed using anti-Cdc42 antibody. Lower panel, band intensities of GTP-Cdc42 normalized to total Cdc42 expressed as mean±SEM from 6 independent experiments. (c) Immunoblotting was performed using anti-phospho-p38 MAPK antibody. Blots were stripped and re-probed with antibody detecting total p38 MAPK. Lower panel, band intensities of p-p38 MAPK normalized to total p38 MAPK expressed as mean±SEM from 7 independent experiments. (d) Experiments were performed as in (c) using anti-phospho-Erk and anti-total Erk antibodies. Mean±SEM from 8 independent experiments. (e) Experiments were performed as in (c) using anti-phospho-Akt and anti-total Akt antibodies. Mean±SEM from 4 independent experiments. *, $p<0.05$; , $p<0.01$; $p<0.005$; **, $p<0.0001$.
Figure 21B:
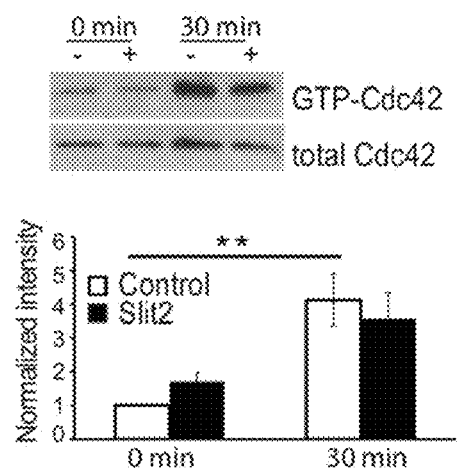

Slit2 has been shown to prevent chemotactic migration of various cell types by preventing activation of the Rho-family GTPases, Cdc42 and Rac (Kanellis, Garcia et al. 2004; Liu, Hou et al. 2006; Prasad, Qamri et al. 2007; Tole, Mukovozov et al. 2009). To determine whether Slit2 inhibits platelet adhesion and spreading in a similar manner, GST beads conjugated to the p21-binding domain (PBD) of PAK1 were used to detect the activated GTP-bound species of Cdc42 and Rac (Tole, Mukovozov et al. 2009). Since the predominant isoform of Rac in human platelets is Rac1, the effects of Slit2 on Rac1 activation was specifically studied (McCarty, Larson et al. 2005). Unstimulated platelets exhibited low basal levels of activated Rac1 and Cdc42 (FIG. 21a,b), and as expected, platelet spreading on fibrinogen increased levels of activated Rac1 five-fold and Cdc42 four-fold (FIG. 21a,b; Rac1, basal 1.0 vs fibrinogen $4.9 \pm 1.1$ $p<0.05$; Cdc42, basal 1.0 vs fibrinogen $4.1 \pm 0.8$; $p<0.01$). Slit2 did not affect basal levels of activated Rac1 and Cdc42, nor did it prevent activation of these Rho-family GTPases during platelet spreading (FIG. 21a,b; Rac1, basal 1.0 vs fibrinogen $1.3 \pm 0.3$; Cdc42, basal 1.0 vs fibrinogen $1.7 \pm 0.3$; Rac1, control $4.9 \pm 1.1$ vs Slit2 $4.6 \pm 1.3$; Cdc42, control $4.1 \pm 0.8$ vs Slit2 $3.6 \pm 0.8$). These data suggest that Slit2 does not inhibit platelet spreading by preventing activation of Rac1 or Cdc42.

Figure 21C:
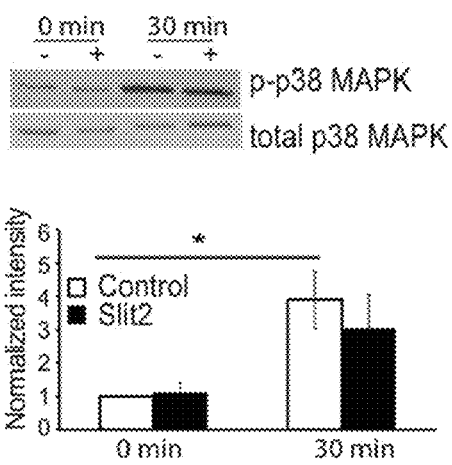
Figure 21D:
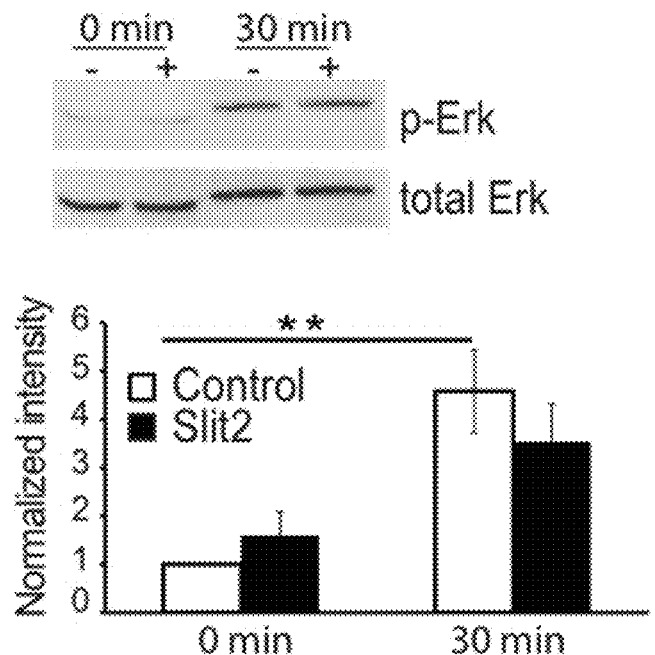
Figure 21E:
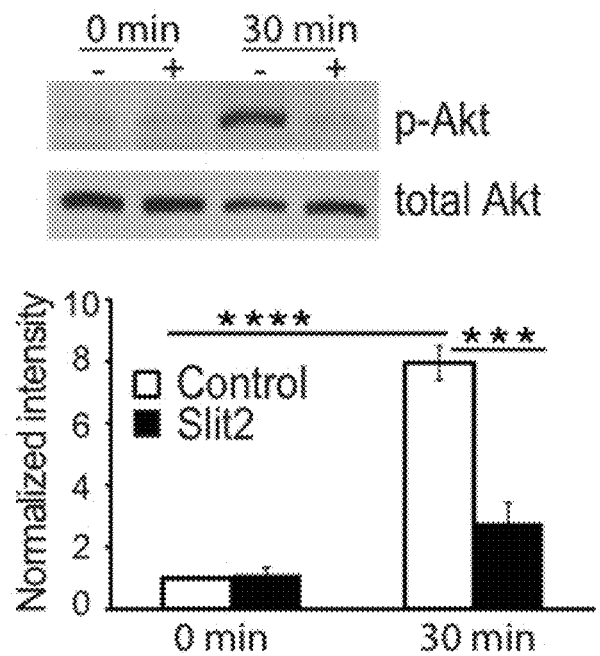

Slit2 Suppresses Activation of Akt, but not Erk or p38 MAPK During Platelet Spreading Adhesion of platelets also involves activation of several major kinase pathways, namely p38 MAPK, Erk and Akt (Lai, Chaudhary et al. 2001; Chen, De et al. 2004; Woulfe, Jiang et al. 2004; Li, Zhang et al. 2006; Mazharian, Roger et al. 2007). As expected, platelet spreading on fibrinogen resulted in a significant increase in phosphorylation of p38 MAPK, Erk, and Akt (FIG. 21c-e; p38 MAPK, $4.0 \pm 0.9$ vs basal 1.0, $p<0.05$; Erk, $4.6 \pm 0.9$ vs. basal 1.0, $p<0.01$; Akt, $8.0 \pm 0.6$ vs basal 1.0, $p<0.0001$). Slit2 treatment had no effect on the basal level of kinase activation (FIG. 21c-e; p38 MAPK, $1.1 \pm 0.3$ vs. basal 1.0; Erk $1.6 \pm 0.5$ vs basal 1.0; Akt $1.1 \pm 0.2$ vs basal 1.0). Slit2 treatment had no effect on phosphorylation of p38 MAPK or Erk (FIG. 21c,d; p38 MAPK, control $4.0 \pm 0.9$ vs Slit2 $3.0 \pm 1.0$; Erk, control $4.6 \pm 0.9$ vs Slit2 $3.5 \pm 0.8$). In contrast, Slit2 significantly inhibited activation of Akt (FIG. 21e, control $8.0 \pm 0.6$ vs Slit2 $2.8 \pm 0.7$; $p<0.005$). Collectively, these data suggest that Slit2 inhibits platelet spreading by suppressing activation of Akt.

Slit2 Inhibits ADP-Mediated Platelet Activation

Figure 22A:
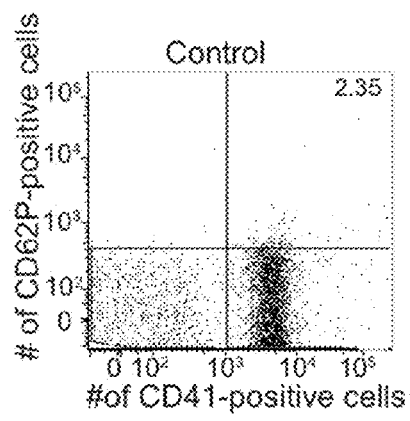
FIG. 22 shows Slit2 suppresses ADP-mediated platelet activation response. Platelet-rich plasma (PRP) was diluted with HEPES-Tyrode's buffer to a cell density of $10^7$/ml, and incubated with Slit2 (4.5 µg/ml) or an equal volume of PBS (control) for 10 min at 37° C. Platelets were stimulated with ADP (10 µM) for 1 min, fixed and incubated with phycoerythrin-conjugated anti-CD62P antibody and fluorescein isothiocyanate-conjugated anti-CD41 antibody. Flow cytometric analysis was performed using a Becton-Dickinson LSR II and FlowJo software. (a) Resting platelets (control). (b) Resting platelets incubated with Slit2. (c) Platelets stimulated with ADP. (d) Platelets pre-incubated with Slit2 prior to ADP stimulation. Representative images of one from three similar independent experiments are shown. Numerical values indicate percentage of platelets positive for both surface CD62P and CD41. (e) Graph depicting the percentage of CD62P-positive resting platelets (control), resting platelets incubated with Slit2, platelets activated with ADP, and platelets pre-treated with Slit2 prior to activation with ADP. Data are expressed as mean±SEM from 3-5 independent experiments. *, $p<0.01$, $p<0.0001$.
Figure 22B:
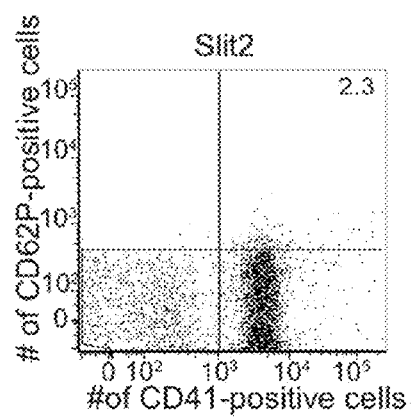
Figure 22C:
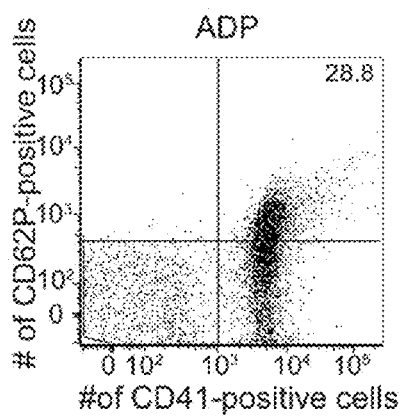
Figure 22D:
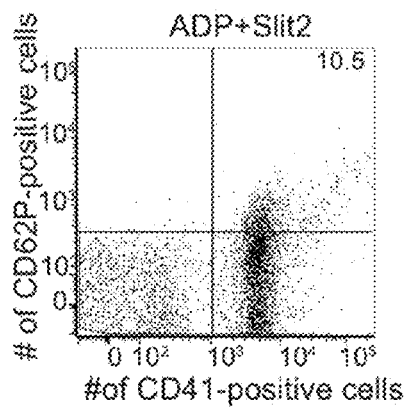
Figure 22E:
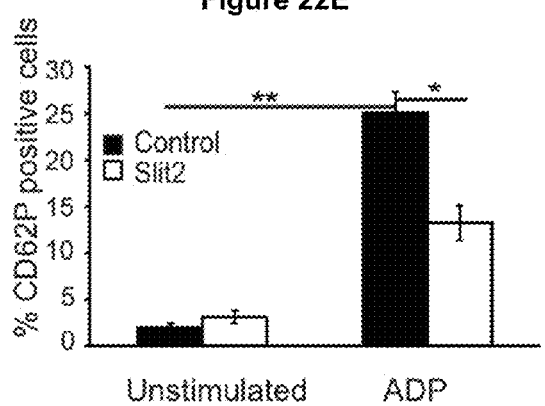

When platelets adhere to injured blood vessels and become activated they release several molecules, including ADP, that trigger vascular inflammation and platelet activation and aggregation. The ability of Slit2 to influence platelet activation was examined by using flow cytometry to monitor cell surface expression of CD62P, which translocates to the surface in activated platelets. In untreated cells, ADP stimulation significantly increased the percentage of platelets expressing cell-surface CD62P (FIG. 22a,c,e; control $2.0 \pm 0.5$ vs ADP $25.0 \pm 2.2$; $p<0.0001$), and this response was significantly less for cells treated with Slit2 (FIG. 22c-e; $13.2 \pm 1.9$; $p<0.01$). These results indicate that in addition to inhibiting platelet adhesion to and spreading on immobilized substrates, Slit2 also modulates platelet responses to soluble agonists such as ADP.

Slit2 Prolongs Bleeding Time in Mice In Vivo

Figure 23A:
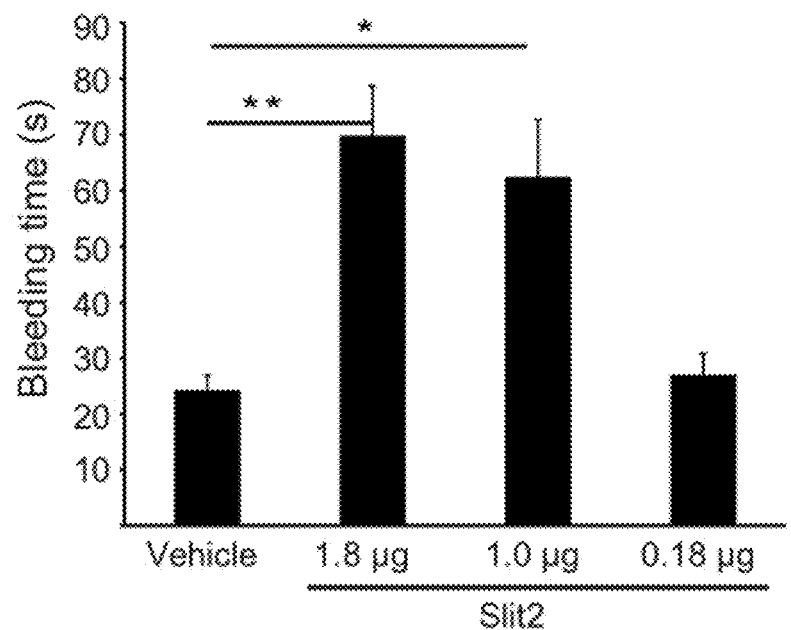
FIG. 23 shows Slit2 increases bleeding time in vivo. CD1 mice were intravenously injected with the indicated dose of Slit2 or vehicle (0.9% NaCl). Two h later, 5 mm of the distal tail was transected and immediately immersed in pre-warmed saline. (a) Bleeding times for mice from vehicle control and Slit2 treatment groups. Data are expressed as mean±SEM for 6-15 mice from each group. *, $p<0.05$; , $p<0.01$. (b) The blood loss from each mouse was quantified by measuring hemoglobin content of the saline in which the tails were immersed. Hemoglobin content was determined by measuring absorbance at 575 nm. Data are expressed as mean±SEM. , $p<0.01$. (c) Experiments were conducted as in (a) using recombinant mouse truncated N-terminal Slit2 (Slit2-N) administered at the indicated doses. Data are expressed as mean±SEM for 6-15 mice from each group. *, $p<0.05$; **, $p<0.01$. (d) Experiments were conducted as in (b) following administration of Slit2-N at the indicated doses. Data are expressed as mean±SEM for 6-12 mice from each group. *, $p<0.05$.
Figure 23B:
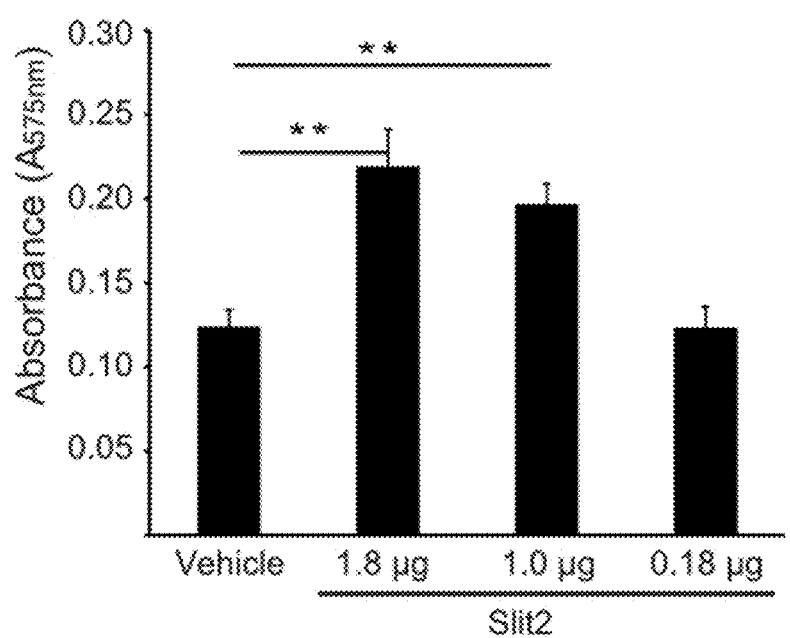
Figure 23C:
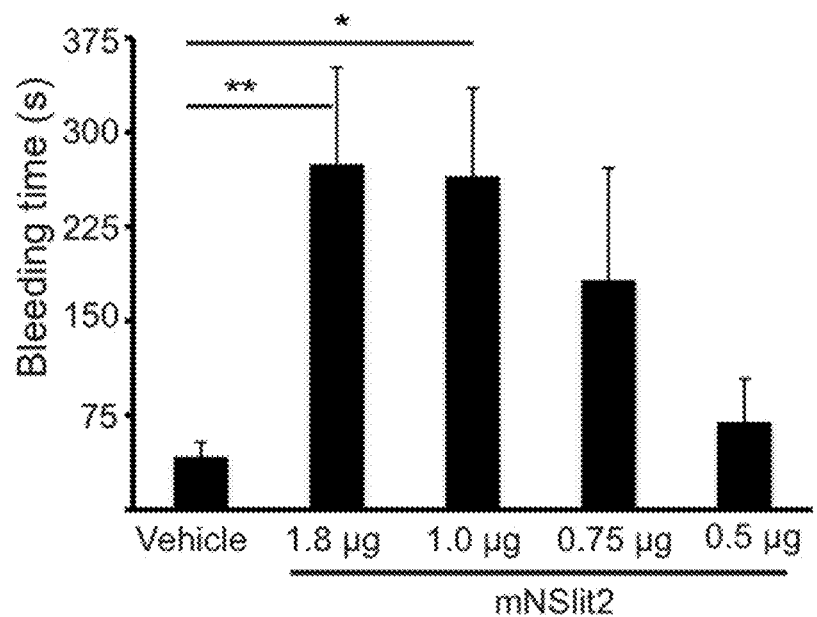
Figure 23D:
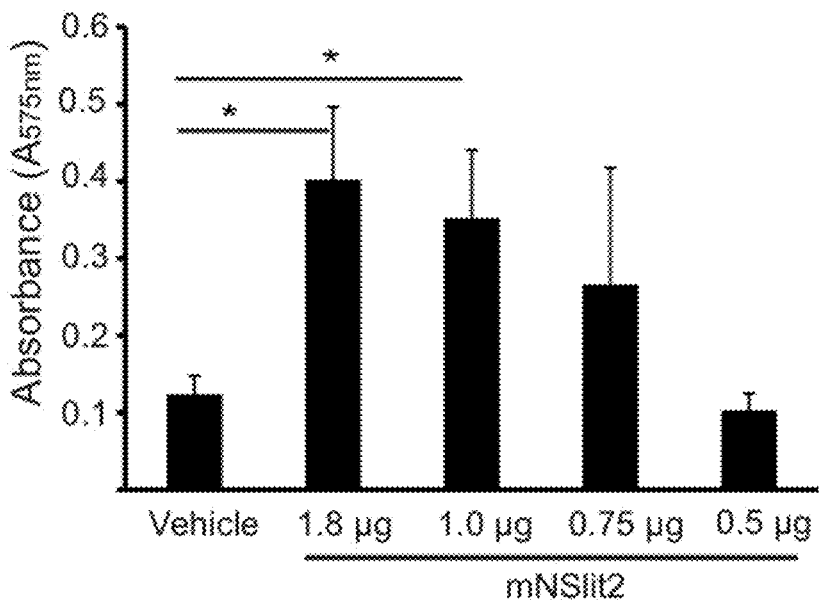

Slit2 inhibits platelet adhesion, spreading and activation in vitro. To determine Slit2's possible effects on platelet function in vivo, the well-described murine tail bleeding model was used. Following administration of control vehicle, bleeding time was $24.3 \pm 2.7$ s (FIG. 23a). Following intravenous administration of Slit2 at doses of 1 μg/mouse and 1.8 μg/mouse the bleeding time was significantly prolonged to $61.5 \pm 9.5$ s and $69.8 \pm 8.9$ s respectively (FIG. 23a; Slit2 1 μg, $p<0.05$ vs. vehicle; Slit2 1.8 μg, $p<0.01$ vs. vehicle). To supplement these observations the hemoglobin content of the saline into which the amputated tails were immersed was quantified by measuring absorbance at 575 nm. Following administration of vehicle, the absorbance was 0.12±0.01 (FIG. 23b), which rose to 0.20±0.01 (FIG. 23b, p<0.01 vs. vehicle) for Slit2 1.0 µg dose and 0.22±0.02 (FIG. 23b, p<0.01 vs. vehicle) for Slit2 1.8 µg. Since the repulsive effects of Slit2 are thought to be mediated by the leucine-rich regions present at the N-terminus, it was next tested whether a truncated N-terminal preparation of Slit2 (Slit2-N) similarly mediates the observed effects on hemostasis (Liu D et al. 2006). Administration of Slit2-N prolonged bleeding time in a dose-dependent manner, with prolongation of bleeding time by ten-fold at the highest dose of Slit2-N administered (vehicle 27.6±6.5 vs 1.8 µg Slit2 274.5±76.9; p<0.01). Together, these results indicate that Slit2 potently inhibits platelet-mediated hemostasis in vivo.

Discussion

The soluble protein, Slit2, interacting with its transmembrane receptor, Robo1, was first described in *Drosophila* as a neuronal and axonal repellent during development of the central nervous system (Kidd, Brose et al. 1998; Brose, Bland et al. 1999; Kidd, Bland et al. 1999). Since then, Slit2 has been shown to inhibit chemotaxis of leukocytes and VSMC towards a number of attractant cues associated with critical events in the progression of vascular lesions (Wu, Feng et al. 2001; Kanellis, Garcia et al. 2004; Liu, Hou et al. 2006; Prasad, Qamri et al. 2007; Tole, Mukovozov et al. 2009). However, the effect of Slit2 on platelet functions has been previously unexplored. In this study the unexpected ability of Slit2/Robo-1 interactions to inhibit several aspects of platelet adhesion, activation, and thrombus formation in vitro and in vivo was demonstrated. The anti-thrombotic properties of Slit2 point to its use as a potent agent capable of simultaneously preventing the vascular inflammation, neointimal proliferation and thrombus formation that collectively result in occlusion of diseased vessels.

Although neuronal guidance cues belonging to the semaphorin and ephrin families have been implicated in leukocyte migration and platelet function, their precise role is unclear. Indeed, ephrins and semaphorins have been reported to both enhance and inhibit inflammation and platelet function (Hall, Boumsell et al. 1996; Aasheim, Delabie et al. 2005; Kashiwagi, Shiraga et al. 2005; Kumanogoh, Shikina et al. 2005; Prevost, Woulfe et al. 2005; Hjorthaug and Aasheim 2007; Zhu, Bergmeier et al. 2007; Zhu, Stalker et al. 2009). Slit2 inhibits inflammatory cell and VSMC recruitment both in vitro and in vivo. (Wu, Feng et al. 2001; Kanellis, Garcia et al. 2004; Liu, Hou et al. 2006; Prasad, Qamri et al. 2007; Tole, Mukovozov et al. 2009). Although Slit2 inhibits chemotactic migration of leukocytes and VSMC, the underlying mechanisms are not well understood. Slit2 has recently been shown to inhibit polarization of migrating cells by preventing activation-induced generation of actin filament free barbed ends, necessary for rapid actin polymerization at the leading edge of the cell (Sun, Magalhaes et al. 2007; Tole, Mukovozov et al. 2009). These data are in keeping with observations from neuronal cells connecting Robo-1 to cytoskeletal proteins, including Slit-Robo GTPase-activating protein-1 (srGAP1) and Ena (Bashaw, Kidd et al. 2000; Wong, Ren et al. 2001).

Platelet adhesion and spreading also involve cytoskeletal stabilization and destabilization. It was presently found that Slit2 inhibited platelet spreading on diverse substrates, including fibrinogen, fibronectin and collagen. Platelet spreading on fibrinogen engages the most abundant receptor on the platelet surface, GPIIb/IIIa, whereas spreading on collagen is supported by GPVI and GPIa/IIa and spreading on fibronectin involves GPIIb/IIIa as well as GPIc/IIa (Moroi, Jung et al. 1996; Ruggeri 2002; Kuijpers, Schulte et al. 2003; McCarty, Zhao et al. 2004). Platelet adhesion and spreading depend on rapid phospholipid metabolism and activation of major kinase pathways, especially Akt, Erk and p38 MAPK. It was presently found that Slit2 did not inhibit activation of Erk or p38 MAPK during platelet spreading. The present results are supported by observations of human neutrophils, human granulocytic cells and Jurkat T lymphocytes, where Slit2 did not affect chemoattractant-induced activation of Erk or p38 MAPK (Wu, Feng et al. 2001; Tole, Mukovozov et al. 2009). In yet another study, Slit2 suppressed Erk activation in chemokine-stimulated breast cancer cells (Prasad, Fernandis et al. 2004).

Akt is a well-recognized downstream effector of phosphatidylinositol 3-kinase (PI3K) and has been shown to phosphorylate and activate GPIIb/IIIa, thereby regulating actin assembly and promoting platelet shape change and stable aggregation (Kovacsovics, Bachelot et al. 1995; Hartwig, Kung et al. 1996; Kandel and Hay 1999; Trumel, Payrastre et al. 1999; Kirk, Sanderson et al. 2000; Chen, De et al. 2004; Jackson, Yap et al. 2004; Woulfe, Jiang et al. 2004; Stojanovic, Marjanovic et al. 2006; Yin, Stojanovic et al. 2008). It was presently found that Slit2 inhibited Akt activation during platelet adhesion and spreading. These results are in concordance with those of others, demonstrating that Slit2 suppressed activation of Akt in Jurkat T lymphocytes following chemokine stimulation (Prasad, Qamri et al. 2007). Interestingly, Akt-deficient platelets have a defect in secretion that results in reduced fibrinogen binding and consequently impaired aggregation (Woulfe, Jiang et al. 2004). The differential effects of Slit2 on inducible kinase activity can be attributed to the different cell types used. Previous reports have involved stimulating cells using chemoattractants in solution, whereas the present study focused on deciphering how Slit2 modulates signaling pathways during platelet adhesion and spreading on immobilized ligands. The present studies indicate that Slit2 may suppress platelet spreading, in part, by down-regulating Akt activation by limiting integrin function.

The present studies further demonstrated that during platelet adhesion and spreading, activation of the small Rho-family GTPase, Cdc42, was not affected by Slit2. These data differ from studies in human neutrophils and brain tumor cells, in which Slit2 inhibited cell migration by preventing activation of Cdc42 (Wong, Ren et al. 2001; Werbowetski-Ogilvie, Seyed Sadr et al. 2006; Tole, Mukovozov et al. 2009; Yiin, Hu et al. 2009). In another report involving VSMC, Slit2 inhibited cell chemotaxis but did not prevent Cdc42 activation (Liu, Hou et al. 2006; Prasad, Qamri et al. 2007). It was found that the formation of dynamic, motile platelet filopodia was unaffected by Slit2. These results are entirely in keeping with observations in platelets derived from Cdc42-deficient mice. In platelets lacking Cdc42, spreading on fibrinogen and filopodial formation are completely intact (Pleines, Eckly et al. 2010).

Using time-lapse videomicroscopy, it was observed that Slit2 inhibited formation of lamellipodia during platelet adhesion and spreading. These effects are reminiscent of Rac1 deficiency. Indeed, platelets from Rac1-deficient mice display impaired lamellipodia formation and spreading on collagen, but retain the ability to form filopodia (McCarty, Larson et al. 2005). Surprisingly, Slit2 did not inhibit activation of Rac1 during platelet spreading. This could be due to activation of the Rac pathway via secondary platelet agonist receptors, such as the P2Y12 and $TXA_2$ receptors, or may reflect the fact that in platelet adhesion and spreading activation of Rac1 is acute, transient and limited to early stages.

It was found that during ADP-mediated activation, Slit2 inhibited CD62P translocation to the platelet surface. These results are in keeping with work from other groups identifying a central role for Akt in platelet granular secretion (Chen, De et al. 2004; Woulfe, Jiang et al. 2004; Yin, Stojanovic et al. 2008). The present findings are also in agreement with a recent study showing that Cdc42 is not required for α-granule secretion (Pleines, Eckly et al. 2010).

Local and systemic inflammation play critical roles in vascular injury and atherosclerosis via pathological processes involving leukocytes, VSMC and platelets. The latter are the primary effectors of the formation of thrombi that ultimately occlude vessels to cause myocardial or cerebral ischemia and infarction (Libby 2002; Meadows and Bhatt 2007; Gawaz 2008). Given the variety of cells, responses and molecular cues involved in atherothrombosis it is unlikely that targeting a single pathologic pathway—such as leukocyte infiltration or platelet activation—will provide comprehensive clinical benefit. Up until now, the search for a single therapy that simultaneously blocks the different pathologic processes that cause vascular injury has proven elusive. The present study shows that Slit2 inhibits platelet adhesion, spreading and activation, and previous reports as well as the present study have demonstrated that the same protein inhibits leukocyte recruitment and chemotactic VSMC migration (Wu, Feng et al. 2001; Kanellis, Garcia et al. 2004; Liu, Hou et al. 2006; Prasad, Qamri et al. 2007; Tole, Mukovozov et al. 2009).

Materials and Methods

Reagents and Antibodies

Horm collagen (Equine Type 1) was from Nycomed (Melville, N.Y.), hirudin from Bayer Inc. (Toronto, ON), recombinant mouse truncated Slit2 (Slit2-N) from R&D Systems (Minneapolis, Minn.), human von Willebrand factor (vWF) from Haematologic Technologies Inc. (Vermont, USA) and all other chemicals from Sigma-Aldrich (St. Louis, Mo.). The following antibodies were used: anti-Robo-1 (Abcam, Cambridge, Mass.), goat anti-CD62P (Santa Cruz Biotechnology Inc, CA), PE-conjugated anti-CD62P (BD Biosciences, Mississauga, ON, Canada), and FITC-conjugated anti-CD41 (BD BioSciences). Anti-Cdc42, anti-Rac1, anti-Erk, anti-phospho-Erk, anti-p38 MAPK, anti-phospho-p38 MAPK, anti-Akt, and anti-phospho-Akt antibodies were from Cell Signaling (Danvers, Mass.). AlexaFluor-conjugated antibodies were from Invitrogen (Burlington, ON) and HRP-conjugated antibodies from Jackson Immunoresearch Laboratories (Bar Harbor, Me.). Large-scale expression and purification of full length human Slit2 was performed as described (Tole, Mukovozov et al. 2009).

Isolation of Human and Murine Platelets

Whole blood (6 vol) was collected from healthy donors into acid citrate dextrose (ACD; 1 vol) and centrifuged at 160 g for 10 min to obtain platelet-rich plasma (PRP). PRP was washed with PBS adjusted to pH 6.3 with ACD, and centrifuged at 800 g for 10 min. Platelets were resuspended in HEPES (10 mM) modified Tyrode's buffer (136 mM NaCl, 2.7 mM KCl, 0.42 mM $NaH_2PO_4$, 19 mM $NaHCO_3$, 0.35 mM $Na_2HPO_4$, 5.5 mM glucose, 1 mM $CaCl_2$, 1 mM $MgCl_2$ pH 7.2). Human megakaryocytes were isolated as previously described (Lo, Li et al. 2005).

Murine blood collected by cardiac puncture in hirudin (20 µg/ml) was centrifuged at 100 g for 10 min. PRP was fixed using 4% paraformaldehyde, washed, and resuspended in HEPES-Tyrode's buffer.

Immunoblotting and Immunofluorescence Labeling

Immunofluorescent labeling of washed platelets, and immunoblotting of cell lysates harvested from human megakaryocytes and mature platelets were performed using anti-Robo-1 antibody (Lo, Li et al. 2005; Licht, Pluthero et al. 2009).

In other experiments, platelets ($2 \times 10^8$/ml) were incubated with Slit2 for 10 min at 37° C., and dispensed onto fibrinogen-coated surfaces for 30 min. Lysates were harvested from adherent platelets using lysis buffer (50 mM Tris pH7.5, 10% glycerol, 1% NP-40, 100 mM NaCl, 5 mM $MgCl_2$, 1 mM PMSF, 1× protease inhibitor cocktail, 0.2 mM $NaVO_3$, 1 mM DTT). Proteins were separated by SDS-PAGE and immunoblotting performed using anti-phospho-Akt, phospho-Erk, or phospho-p38 MAPK antibodies. To control for protein loading, blots were stripped and re-probed with antibodies detecting the total species. Densitometry analysis was performed using ImageJ software.

Platelet Spreading Assays

Spreading assays were performed as previously described, with minor modifications (Mazharian, Roger et al. 2007). Washed platelets ($10^7$/ml) were pre-incubated with Slit2 or PBS for 10 min, and dispensed onto fibrinogen-, fibronectin-, or collagen-coated glass coverslips (Tole, Mukovozov et al. 2009). Non-adherent cells were removed by washing. Adherent platelets were labeled with Alexa Fluor 488-conjugated phalloidin (Mazharian, Roger et al. 2007). Cells were visualized using a spinning disc DMIRE2 confocal microscope (Leica Microsystems, Toronto, Canada). Fifteen images from random fields were acquired using a 100× objective lens (1.4 numerical aperture) equipped with a Hamamatsu back-thinned EM-CCD camera and a 1.5× magnification lens (Spectral Applied Research). Platelet surface area was calculated using Volocity™ software.

Microfluidic Adhesion Assays

Channels of the Bioflux microfluidic system (Fluxion Biosciences, CA) were coated with collagen or vWF (50 µg/ml). Washed platelets ($10^7$/ml) were labeled with calcein-AM, pre-incubated with Slit2 or PBS, and flowed through the channels at constant shear rates of 1000 $s^{-1}$ or 1900 $s^{-1}$ for 4 min. Channels were washed at the same shear rates for 4 min, and images acquired on a Leica DMIRE2 deconvolution microscope (10×) (Siljander, Munnix et al. 2004). The surface area covered by adherent platelets was quantified using the Bioflux™ 200 software.

Rac1 and Cdc42 Activation Assays

Following incubation with Slit2, washed platelets ($1.2 \times 10^9$/ml) were allowed to spread on fibrinogen-coated wells for 30 min. Activation of Rac1 and Cdc42 was tested using GST-PBD glutathione beads as previously described (Tole, Mukovozov et al. 2009).

Platelet Activation Response

Cell surface CD62P mobilization, a marker of platelet activation, was measured by flow cytometry (Hagberg and Lyberg 2000). PRP was pre-incubated with Slit2, then with ADP (10 µM) for 1 min (Hagberg and Lyberg 2000). Platelets were fixed, washed, and labeled with anti-CD62P-PE and anti-CD41-FITC antibodies for 30 min. Flow cytometry was performed using a Becton-Dickinson LSR II and BD FACS-Diva software. Analysis was performed using FlowJo software (Tree Star, Inc., Ashland, Oreg.).

Murine Tail Bleeding Assays

Animals were cared for in accordance with the Guide for the Humane Use and Care of Laboratory Animals. All protocols were approved by The Hospital for Sick Children Research Institute Animal Care Committee. Briefly, Slit2 (0-1.8 µg/mouse) was intravenously injected via tail vein in adult CD1 mice (Charles River Laboratories, Wilmington, Mass.). Two h later, mice were anesthetized using 2.5-5% isoflourane, and placed on a heating pad. Five mm of the distal tail was amputated, and the remaining tail immersed in pre-warmed 0.9% NaCl (Cho, Furie et al. 2008). The time required for spontaneous bleeding to cease was recorded. The amount of bleeding was quantified by measuring the hemoglobin content in the pre-warmed saline (Cho, Furie et al. 2008).

Statistical Analysis

Analysis of Variance followed by Bonferonni's or Dunnett's post-hoc testing, was performed to compare group means in multiple comparisons. In all other cases, the Student's two-tailed t-test was used. $p<0.05$ was considered significant.

Example 3

Slit2 Prevents Acute Kidney Injury

Results
Slit2 Inhibits Neutrophil Adhesion to Activated Endothelial Cells

Figure 32:
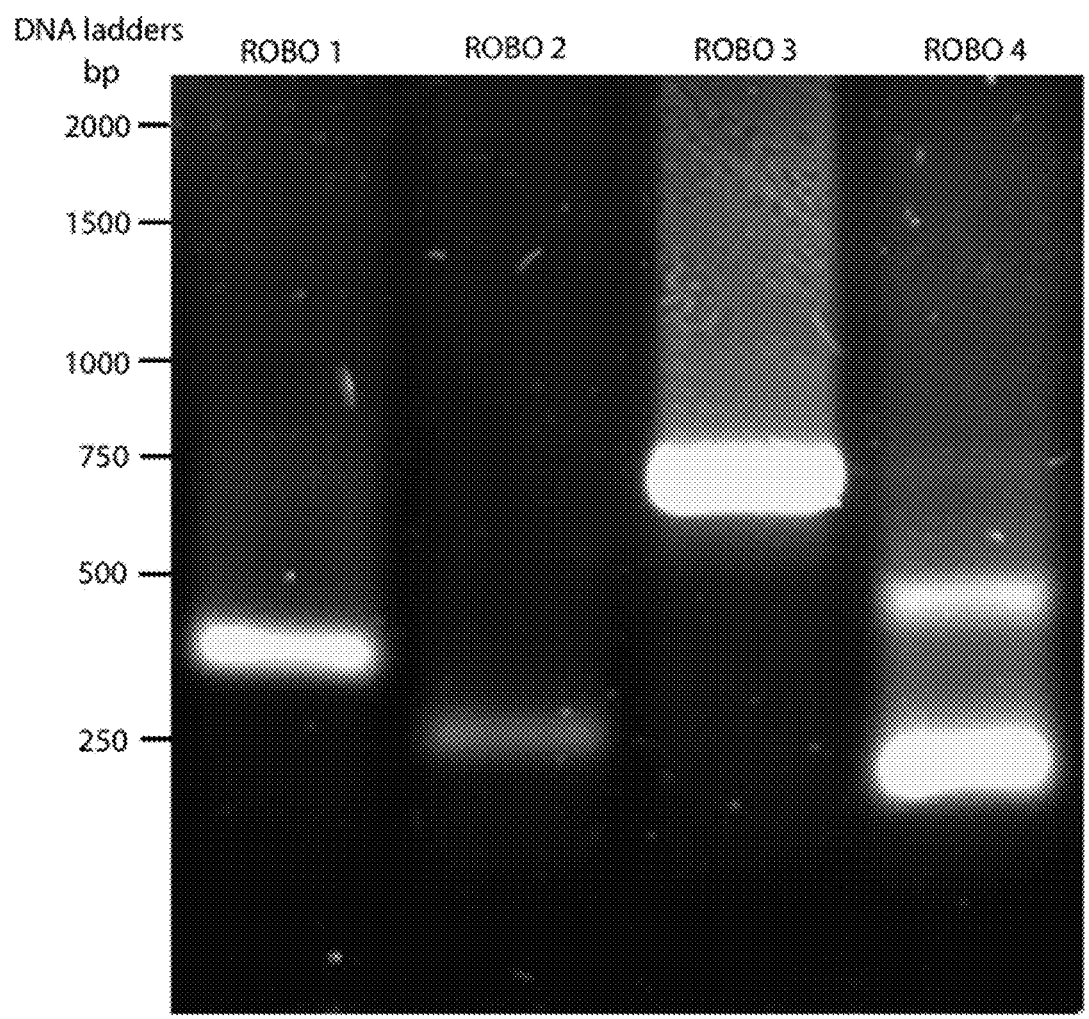
FIG. 32 shows HUVECs express Robo-1, 2 and 4.

Slit2 receptor Robo-1 has been previously shown to be expressed on neutrophils. Additionally Slit2 inhibits the first step of the neutrophil recruitment cascade, namely the chemotaxis of neutrophils towards diverse chemoattractants by preventing the activation of small Rho family of GTPases (Tole, Mukovozov et al. 2009). The subsequent step in leukocyte adhesion cascade, namely neutrophil adhesion to the injured endothelium, also involves activation of Rho family of GTPases (Osborn, Hession et al. 1989; Bochner, Luscinskas et al. 1991; Jones, McIntire et al. 1994). The effects of Slit2 on adhesion of fluorescently labelled human neutrophils to primary human umbilical vascular endothelial cells (HUVECS) were next tested. Since exposure of endothelial cells to IRI is associated with enhanced local production of inflammatory cytokine tumour necrosis factor-α (TNF-α), Slit2's effect on neutrophil adhesion to HUVEC's incubated with TNF-α was first tested. There was minimal neutrophil adhesion under resting conditions (mean fluorescence intensity 46.5±10.6 units). Activation of HUVECS by TNF-α enhanced neutrophil adhesion by 3 fold (142.9±28.5, $p<0.05$, TNF-α vs control, FIG. 25A). In presence of Slit2, neutrophil adhesion significantly decreased to 67.2±12.8 fluorescent units, ($p<0.05$). The expression of Robo on HUVEC cells was next tested using RT-PCR (FIG. 32). In keeping with the results reported previously, it was found that HUVECs express Robo 1, 2 and 4 (Klagsbrun and Eichmann 2005; Zhang, Dietrich et al. 2009). Since the observed effects of Slit2 could potentially result from actions on neutrophil and/or on endothelial cells, the neutrophils were washed after treating them with Slit2 in the adhesion assays. Washed neutrophils were then incubated with endothelial cells and adhesion measured as described previously. Washing the neutrophils did not affect neutrophil adhesion (washed vs. unwashed neutrophil-endothelial adhesion, p=NS, FIG. 25B). Collectively, these data demonstrate that Slit2 acts directly on neutrophils to impair neutrophil adhesion to injured endothelium.

Figure 25A:
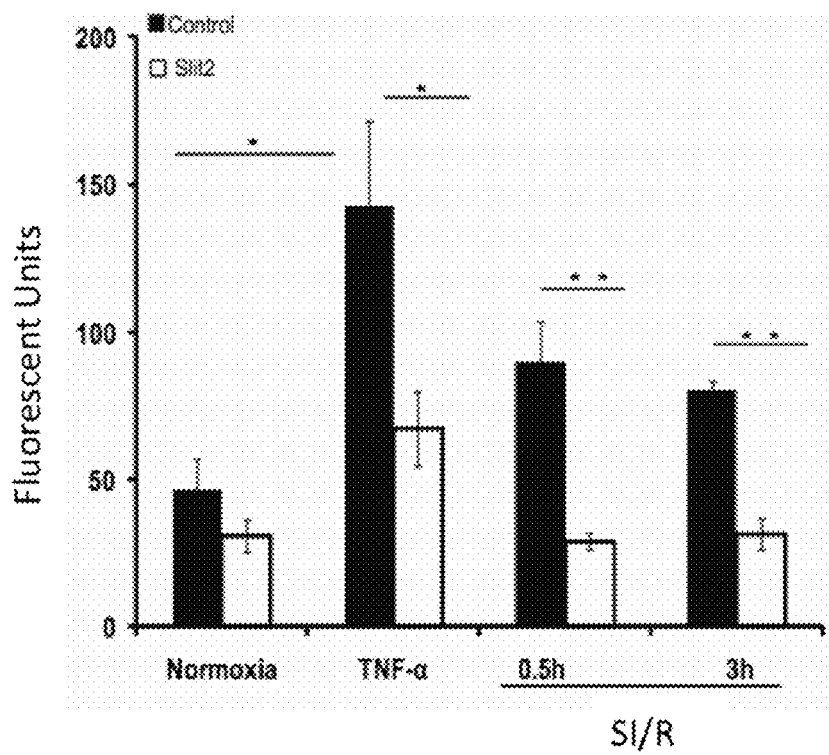
FIG. 25A shows Slit2 inhibits neutrophil adhesion to inflamed endothelium and in simulated ischaemia-reperfusion injury (Si/R). The effect of Slit2 on neutrophil adhesion to inflamed endothelium was tested using TNF-α stimulated endothelium and fluorescently labeled human neutrophils. There was minimal neutrophil adhesion under resting conditions (mean fluorescence intensity 46.5±10.6 units). Activation of HUVECS by TNF-α enhanced neutrophil adhesion by 3-fold (142.9±28.5, p<0.05, TNF-α vs control). In presence of Slit2, neutrophil adhesion significantly decreased to 67.2±12.8 fluorescent units, (p<0.05). To further test the effect of Slit2 in IRI, neutrophil adhesion was measured in HUVECS exposed to SI/R. In HUVECS exposed to 2 hours hypoxia followed by 30 minutes and 3 hours of reoxygenation, the mean fluorescent intensity increased to 89.9±13.4 units and 80±3.2 respectively. Slit2 significantly reduced neutrophil adhesion in cells exposed to SI/R injury with mean fluorescent intensity being 29.1±2.9 for 30 min re-oxygenation and 31.5±5.3 for 3 hour reoxygenation (p<0.001).
Figure 25B:
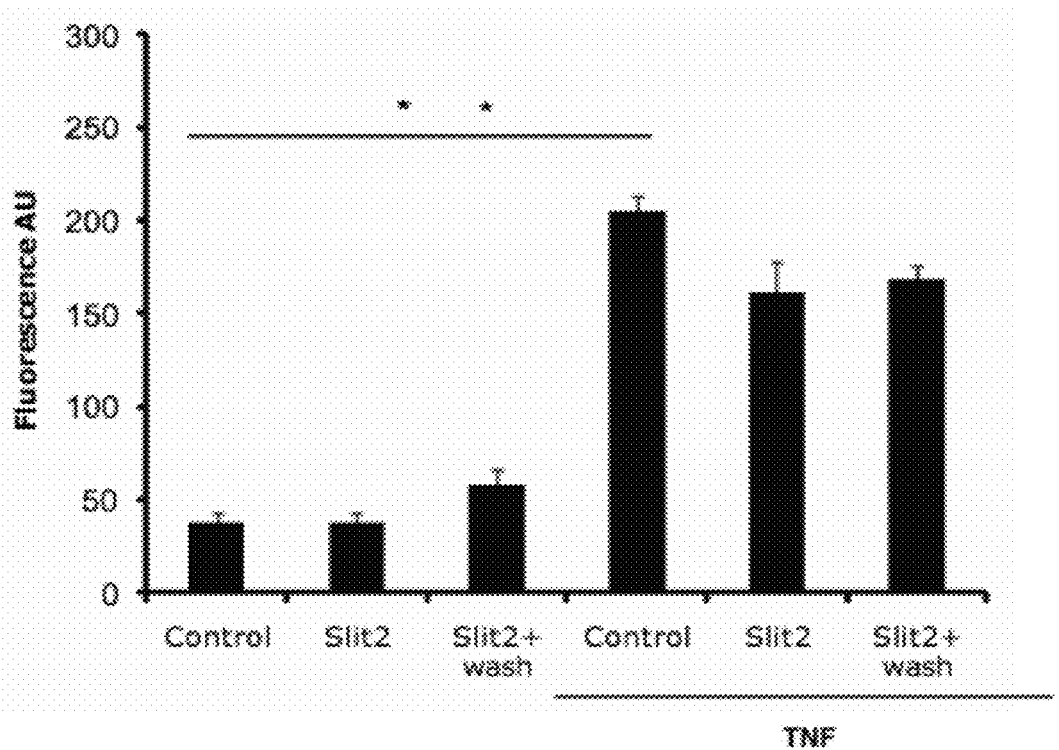
FIG. 25B shows Slit2 inhibits neutrophil-endothelial adhesion by its action on neutrophils. Neutrophils were washed after treatment with Slit2 to get rid of unbound Slit2. Washed neutrophils were then incubated with endothelial cells and adhesion measured as described above. Washing the neutrophils did not affect neutrophil adhesion (washed vs. unwashed neutrophil-endothelial adhesion, p=NS). Collectively, these data demonstrate that Slit2 acts directly on neutrophils to impair neutrophil adhesion to injured endothelium.
Figure 25C:
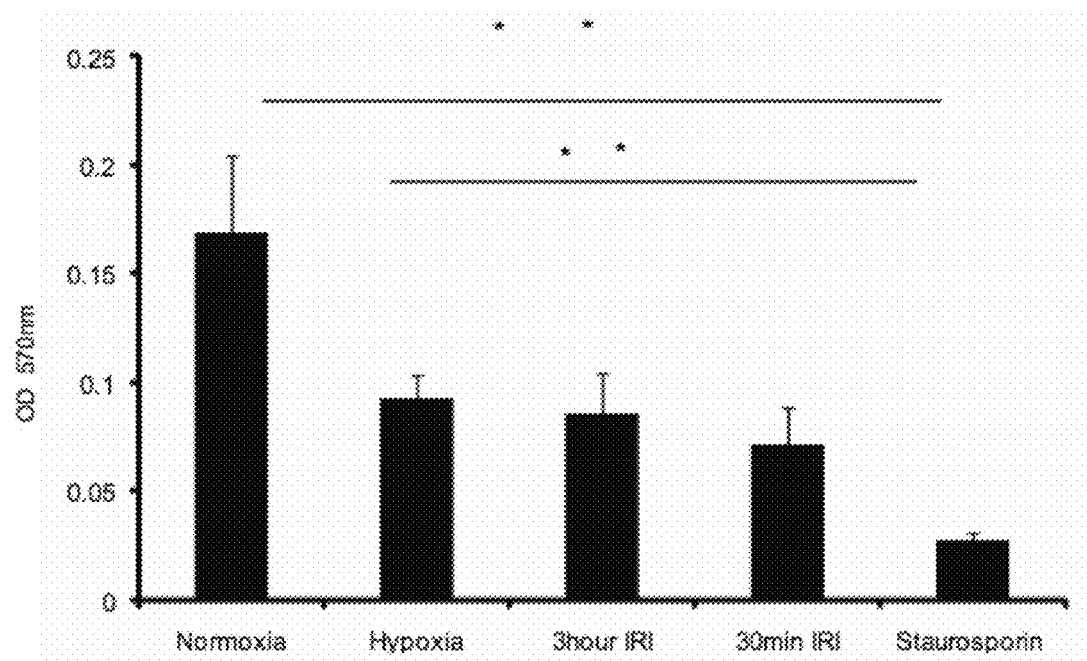
FIG. 25C shows SI/R reduces cell viability of HUVECs. Reduction in cell viability was confirmed using MTT assay. Normoxic cells and cells exposed to Staurosporin were used as positive and negative controls, respectively. HUVESc exposed to hypoxia-reoxygenation injury had reduced cell viability compared to cells grown in normoxic conditions. The mean $OD_{570}$ of cells grown in normoxic conditions was 0.17±0.035 whereas the mean $OD_{570}$ in cells exposed to 2 hours of hypoxia followed by 30 minutes and 3 hours of reoxygenation was 0.072±0.016 and 0.085±0.018, respectively (*p<0.001). The mean $OD_{570}$ of cells exposed to Staurosporin was 0.027±0.003.

Slit2 Inhibits Neutrophil Adhesion to Endothelial Cells Subjected to Hypoxic Injury The effect of Slit2 on adhesion of neutrophils to primary endothelial cells exposed to simulated ischaemia reperfusion injury (SI/R) was next examined. As a first step, viability of HUVECS exposed to SI/R was measured using MTT (3-[4,5-dimethylthiazol-2-yl]-2,5-diphenyl tetrazolium bromide) assay (Pieters, Huismans et al. 1988). The mean $OD_{570}$ of cells grown in normoxic conditions was 0.17±0.035 whereas the mean $OD_{570}$ in cells exposed to 2 hours of hypoxia followed by 30 minutes or 180 min of reoxygenation was reduced to 0.072±0.016 and 0.085±0.018 respectively, (normoxia vs SI/R, $p<0.001$). The mean $OD_{570}$ of cells exposed to apoptosis inducing agent Staurosporin was as expected markedly reduced 0.027±0.003. These data demonstrate that hypoxia-reoxygenation resulted in reduced viability of HUVECs (FIG. 25C).

The effects of Slit2 on neutrophil adhesion to HUVECS exposed to SI/R were next tested. Under normoxic conditions, minimal neutrophil adhesion was seen (mean fluorescence intensity 46.5±10.6 units). When HUVECS were exposed to 2 hours hypoxia followed by 30 minutes or 180 minutes of re-oxygenation, the mean fluorescent intensity increased from 46.5±10.6 units to 89.9±13.4 units and 80±3.2 respectively (SI/R vs normoxia, $p<0.05$). Neutrophils pre-incubated with Slit2 demonstrated significantly less adhesion to HUVEC exposed to SI/R following re-oxygenation periods of both 30 min (29.1±2.9, $p<0.01$) and 3 hours (31.5±5.3, $p<0.01$). These data demonstrate that Slit2 reduces adhesion of neutrophils to endothelium following hypoxia/re-oxygenation injury (FIG. 25A).

Slit2 Reduces Neutrophil Adhesion to Injured Endothelium Under Flow Conditions

Figure 26:
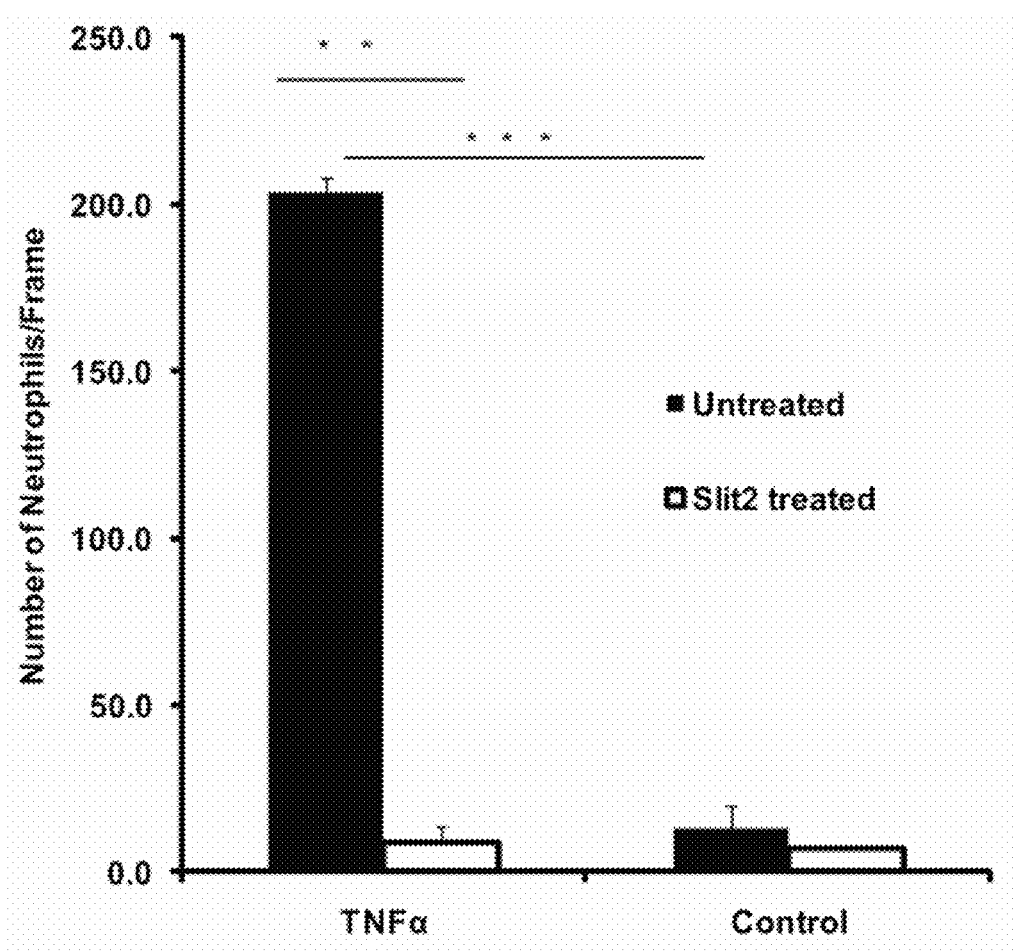
FIG. 26 shows Slit2 inhibits neutrophil adhesion to stimulated endothelium under flow conditions. Neutrophil adhesion under flow conditions was tested using microfluidics. There was minimal neutrophil adhesion to untreated HUVEC monolayer and this was further reduced by pre-treatment of neutrophils with Slit2 (13.3±10.9 cells vs 7±0 cells, p=NS). There was robust increase in neutrophil adhesion to TNF-α stimulated HUVEC with the mean number of adherent neutrophils being 203.3±7.23 and this was significantly reduced by pre-incubating the neutrophils with Slit2 (9±8.2 cells, p<0.001).

Since hydrodynamic shear flow is a critical determinant of neutrophil endothelial interactions within a given vascular bed, the effects of Slit2 on neutrophil adhesion to activated endothelium was next tested using a microfluidic system (Zarbock and Ley 2009). Under basal conditions, there was minimal neutrophil adhesion to endothelial monolayer and this was further reduced by pre-treatment of neutrophils with Slit2 (13.3±10.9 cells vs. 7±0 cells per frame). Activation of endothelial cells with TNF-α resulted in a robust stimulated HUVEC with the mean number of adherent neutrophils being 203.3±7.23 and this was significantly reduced by pre-incubating the neutrophils with Slit2 (9±8.2 cells, $p<0.001$), FIG. 26. This shows that Slit2 effectively inhibits neutrophil adhesion to stimulated endothelium under shear flow conditions.

Slit2 Reduces Neutrophil Transmigration in Inflammation

Figure 27:
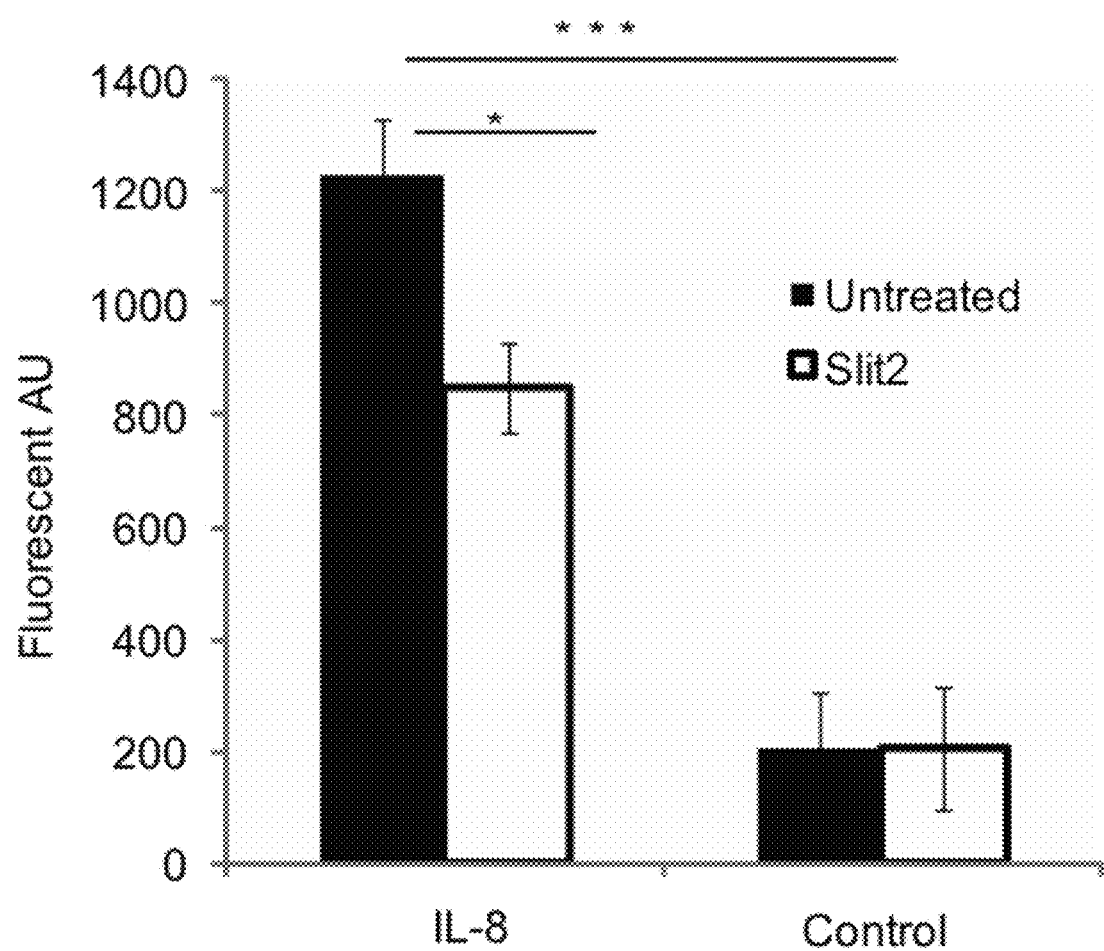
FIG. 27 shows Slit2 reduced neutrophil transmigration. Neutrophil transmigration across the endothelium was tested using transwell assay. HUVECS were grown on the transwell inserts. IL-8 was added in lower wells as an inflammatory chemoattractant and fluorescently labelled neutrophils were added in the upper well. The transendothelial migration increased 6 fold in wells in which IL-8 (50 ng/ml) was added as compared to basal conditions (mean fluorescent intensity 1228±174.4 vs 207.8±169.7, p<0.01) and Slit2 significantly reduced IL-8 induced transmigration (mean fluorescent intensity 849.9±141.9, p<0.05).

In AKI, after the neutrophils firmly adhere to the injured endothelium, they undergo transmigration across the endothelium to infiltrate the injured kidney in response to release of inflammatory chemoattractants. Rho family of GTPases has been implicated in leukocyte transmigration (Boyd, Wawryk et al. 1988; Lyck, Reiss et al. 2003). Therefore, the effect of Slit2 on transendothelial migration of neutrophils towards IL8 was next tested using transwell assays (Bayat, Werth et al. 2010). The transendothelial migration increased 6 fold in wells in which IL8 (50 ng/ml) was added as compared to basal conditions (mean fluorescent intensity 1228±174.4 vs 207.8±169.7, $p<0.01$) and Slit2 significantly reduced IL8 induced transmigration (mean fluorescent intensity 849.9±141.9, $p<0.05$) (FIG. 27). These data demonstrate that Slit2 inhibits inflammatory chemoattractant induced neutrophil transmigration.

Slit2 Improves Renal Function in Renal IRI Model

Figure 28A:
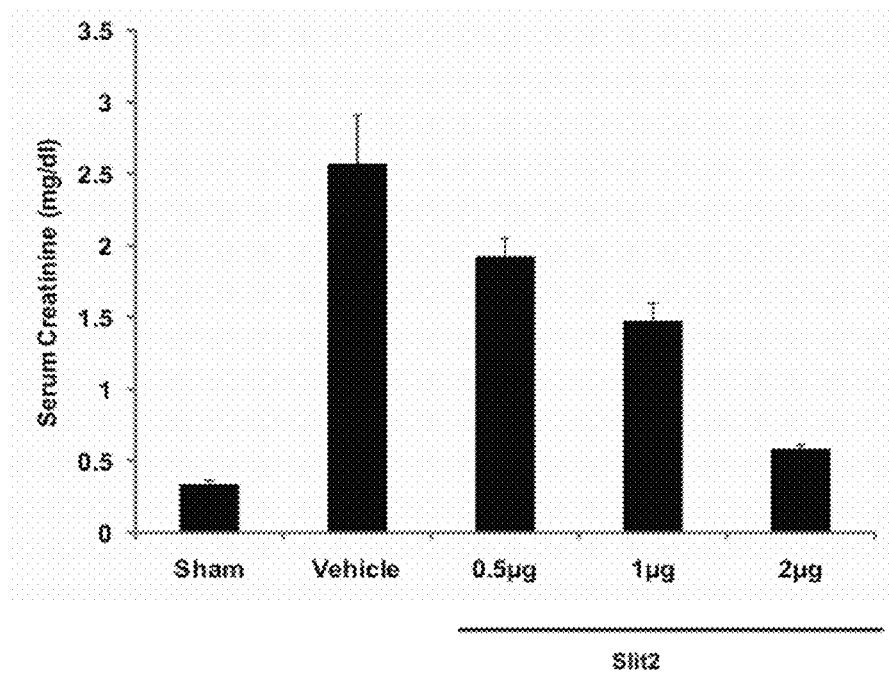
FIG. 28A shows full length Slit2 reduces serum creatinine in a dose dependent manner in renal IRI. Mouse renal ischaemia reperfusion injury was induced by bilateral cross-clamping of renal arteries for 26 minutes. Surgical wounds were closed, and mice returned to cages for up to 24 h. Full length Slit2 (FL-Slit2) at 3 different concentrations (0.5, 1, 2 µg/ml) or vehicle were administered intravenously prior to ischemia-reperfusion injury. FL-Slit2 significantly reduced plasma creatinine in a dose dependent manner. Plasma creatinine in mouse treated with 0.5, 1 and 2 µg/ml of Slit2 was reduced to 1.92±0.13, 1.47±0.13 and 0.58±0.03 mg/dl respectively as compared to mice treated with vehicle only (2.57±0.30 mg/dl, p<0.01).
Figure 29A:
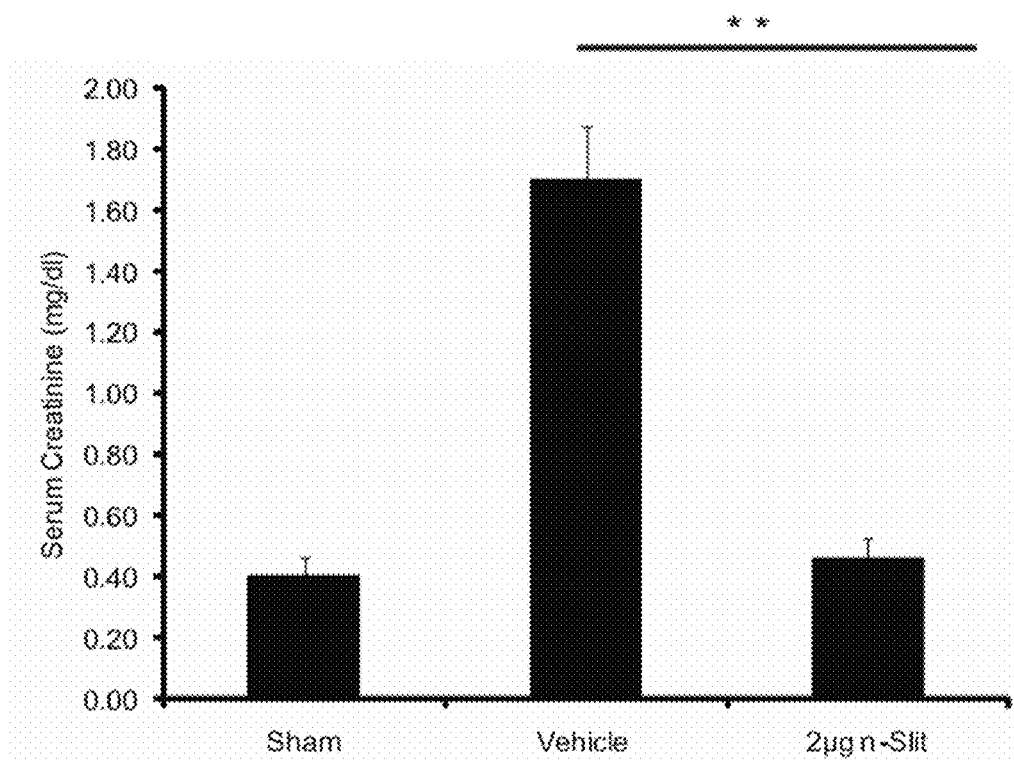
FIG. 29A shows N-terminal of Slit2 is effective in preventing renal IRI. N-terminal Slit2 (2 µg/ml) was given prior to induction of renal ischaemia reperfusion injury in a protocol similar to what is described above. N-terminal Slit2 reduced plasma creatinine to 0.46±0.03 mg/dl as compared to mice treated with vehicle (plasma creatinine 1.70±0.06 mg, p<0.0001).

The present results showed that Slit2 inhibits neutrophil adhesion to injured endothelium as well as transendothelial migration, events which mediate the inflammatory injury associated with AKI. To directly determine the effect of Slit2 on AKI, a well-established mouse model of IRI was used and plasma creatinine was measured 24 hours after induction of injury (Awad, Rouse et al. 2009). Plasma creatinine was significantly higher in vehicle treated mice that underwent bilateral clamping of renal pedicles compared to sham treated mice (vehicle vs. sham 2.58±0.03 vs. 0.34±0.02; p=0). Pretreatment with Slit2 prevented the rise in plasma creatinine in a dose dependent manner (vehicle 2.58±0.03; Slit2 0.5 µg 1.93±0.13; Slit2 1 µg 1.47±0.13; Slit2 2 µg 0.58±0.03; p<0.001, FIG. 28a). Administration of 2 µg dose of truncated N-Slit2, which contains the Leucine rich region (LRR) that binds the Robo receptor, reduced plasma creatinine by four fold (vehicle 1.7±0.06 vs. N-Slit2 (2 µg) 0.46±0.03; p<0.0001, FIG. 29a).

Slit2 Prevents Neutrophil and Macrophage Infiltration to Kidney Following IRI

Figure 28B:
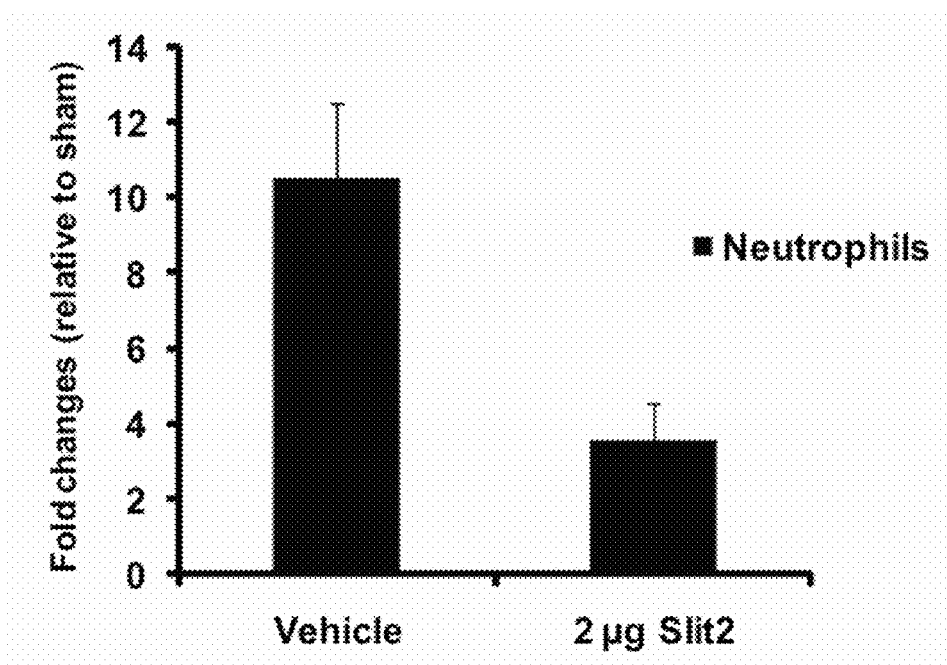
FIG. 28B shows full length Slit2 prevents influx of neutrophils following IRI. Flow cytometry was used to measure renal tissue leukocyte infiltration in mouse renal IRI model. In mice treated with vehicle control prior to induction of IRI, there was a 10.5 fold increase in neutrophil infiltration and 2.5 fold increase in macrophage infiltration as compared to sham mice. Pre-administration of Slit2 (2 µg/mouse) reduced neutrophil infiltration from 10.5 fold to 3.5 fold relative to sham (p<0.01). Similarly pre-administration of N-Slit2 reduced neutrophil infiltration from 14.7 fold to 3.0 fold relative to sham (p<0.001).
Figure 29B:
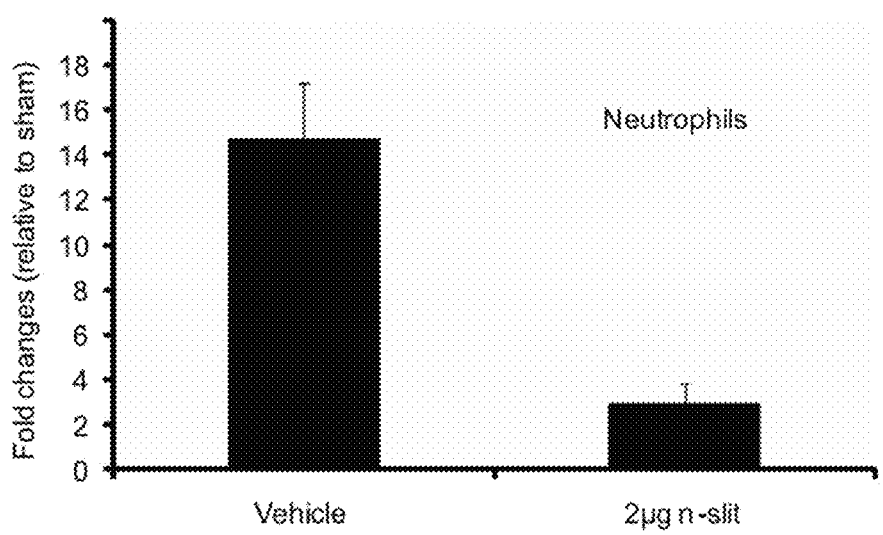
FIG. 29B shows N-terminal of Slit2 is effective in preventing neutrophil infiltration in renal IRI. Pre-administration of N-Slit2 reduced neutrophil infiltration from 14.7 fold to 3.0 fold relative to sham (p<0.001).

Flow cytometry was used to measure renal tissue leukocyte infiltration. In mice treated with vehicle control prior to induction of IRI, there was a 10.5 fold increase in neutrophil infiltration as compared to sham mice. Pre-administration of Slit2 (2 µg/mouse) reduced neutrophil infiltration from 10.5 fold to 3.5 fold relative to sham (p<0.01, FIG. 28b). Similarly pre-administration of N-Slit2 (2 µg/mouse) reduced neutrophil infiltration from 14.7 fold to 3.0 fold relative to sham (p<0.001, FIG. 29b). These data demonstrate that administration of exogenous Slit2 inhibits recruitment of neutrophils to the post-ischemic kidney.

Slit2 Did not Alter Neutrophil Phagocytosis

Figure 30A:
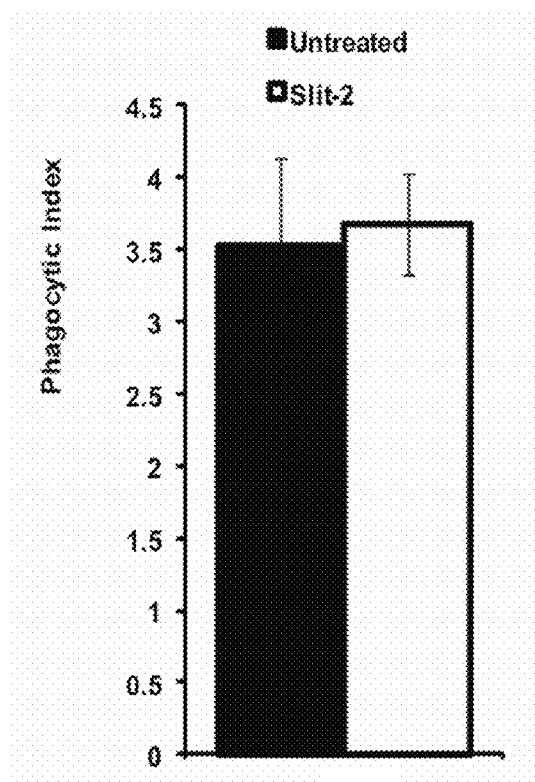
FIGS. 30A-C show Slit2 does not inhibit neutrophil phagocytosis and superoxide production. 8 µm latex beads were coated with human IgG (1 mg/ml) for 2 hours at room temperature. Neutrophils pre-incubated with myc-affinity purified Slit2 (600 ng/ml) or control medium (equal volume) for 10 minutes were exposed to opsonised latex beads. In the absence of Slit2, neutrophils demonstrated a robust phagocytic response, with 77.8±7.1% of neutrophils ingesting at least one bead. A) The mean phagocytic index (#ingested beads/#neutrophils) was 3.53±0.60. B) In the presence of Slit2, 80.6±7.0% of neutrophils ingested at least one bead and had a mean phagocytic index of 3.67±0.35 9. C) Next the superoxide dismutase (SOD) inhibitable reduction of cytochrome c was assayed as a measure of superoxide production. Unstimulated neutrophils did not produce superoxide. Incubation of neutrophils with fMLP or PMA enhanced superoxide production to 66.4±4.75 nmol of superoxide and 20.6±0.060 nmol of superoxide per $10^7$ cells per minute respectively. Pre-treatment with Slit2 did not impair superoxide production, but rather promoted a modest increase in rate of superoxide production (27.8±1.20 nmol of superoxide per $10^7$ cells per minute, p<0.05).
Figure 30B:
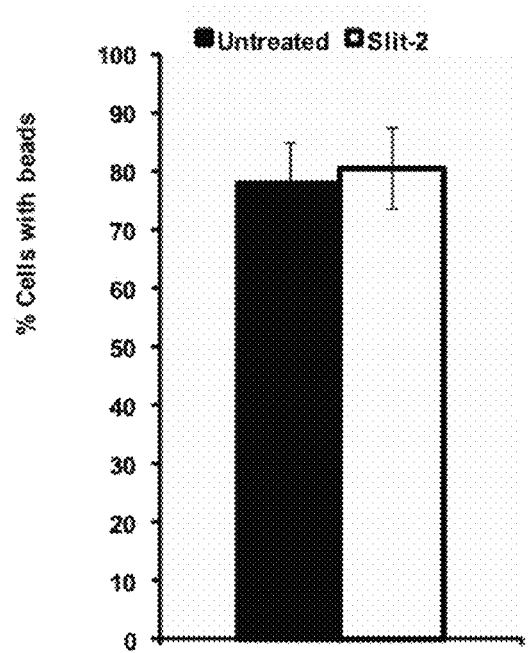

Slit2 was previously demonstrated to inhibit chemotaxis of neutrophils towards diverse chemoattractants by preventing activation of small Rho family of GTPases, Rac and Cdc42 (Tole, Mukovozov et al. 2009). Since these Rho family of GTPases also mediate phagocytosis of opsonised particles, it was hypothesised that Slit2 may interfere with this important neutrophil function (Caron and Hall 1998). In the absence of Slit2, neutrophils demonstrated a robust phagocytic response, with 77.8±7.1% of neutrophils ingesting at least one bead. The mean phagocytic index (#ingested beads/#neutrophils) was 3.53±0.60. In the presence of Slit2, 80.6±7.0% of neutrophils ingested at least one bead and had a mean phagocytic index of 3.67±0.35% (FIGS. 30a and 30b). Thus, treatment with Slit-2 did not impair the ability of neutrophils to undertake Fc-mediated phagocytosis.

Slit2 Treatment does not Inhibit Neutrophil Superoxide Production

In neutrophils, the production of reactive oxygen species by the Rac2-dependent NADPH oxidase activation plays a critical role in the pathogen destruction (Ambruso, Knall et al. 2000; Kim and Dinauer 2001). Since it was previously demonstrated that Slit2 suppresses Rac2 activation in neutrophils, it was next postulated that Slit2 would inhibit the respiratory burst of human neutrophils (Tole, Mukovozov et al. 2009).

Figure 30C:
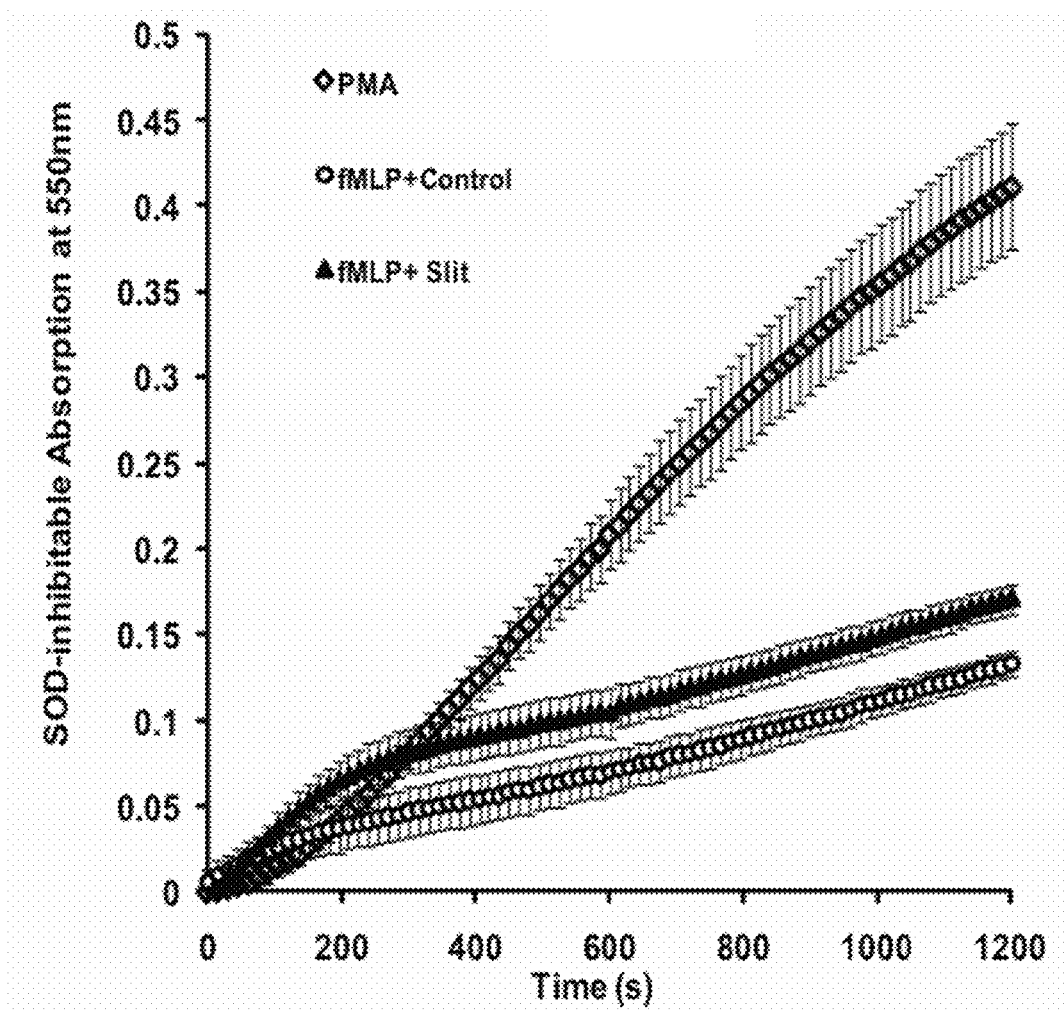

To test this hypothesis, the superoxide dismutase (SOD) inhibitable reduction of cytochrome c was assayed as a measure of superoxide production. Unstimulated neutrophils did not produce superoxide. Incubation of neutrophils with fMLP or PMA enhanced superoxide production to 66.4±4.75 nmol of superoxide and 20.6±0.060 nmol of superoxide per $10^7$ cells per minute respectively. Pre-treatment with Slit2 did not impair superoxide production, but rather promoted a modest increase in rate of superoxide production (27.8±1.20 nmol of superoxide per $10^7$ cells per minute, p<0.05; FIG. 30c).

Slit2 does not Impair Immunity in Mouse *Listeria* Infection Model

Figure 31:
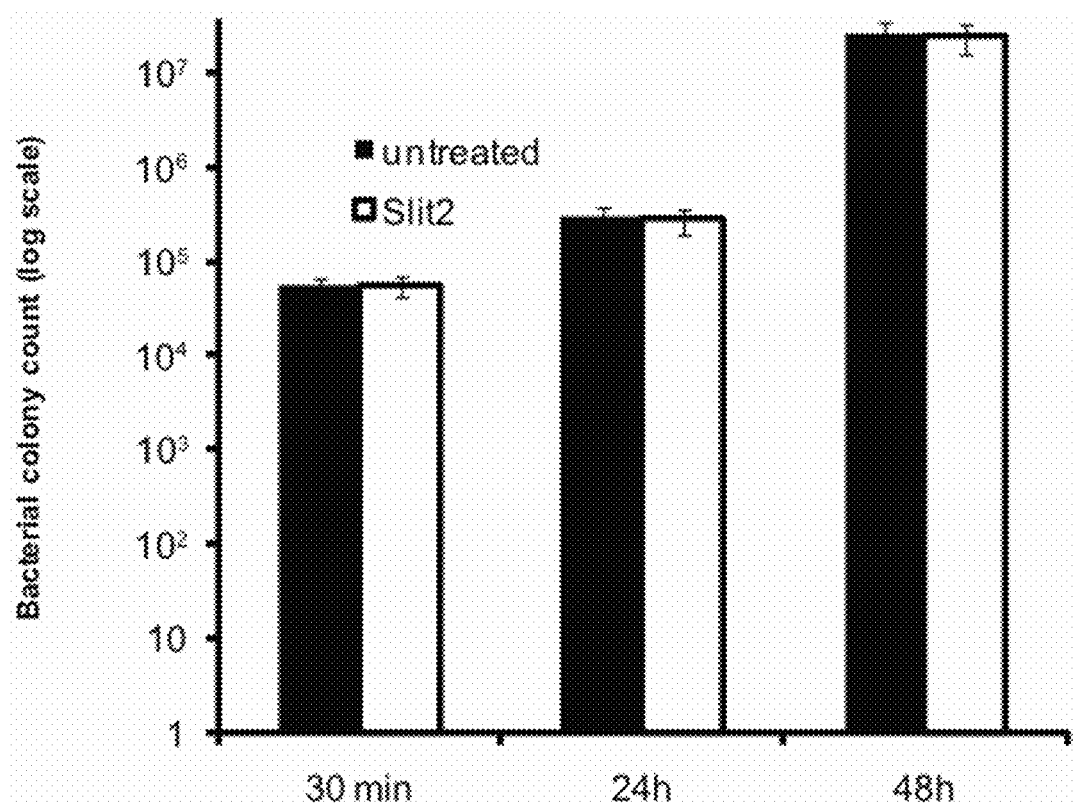
FIG. 31 shows Slit2 does not impair infection response. 6-8 week old C57BL/6 mice were used. Slit or control vehicle was given intravenously (via tail vein) into each mouse. *Listeria monocytogenes* $5 \times 10^4$ CFU in 200 µl of PBS was injected intravenously one hour later. Mice were sacrificed by cervical dislocation at 30 min, 24 hour and 48 hour post injection. The bacterial colony counts were similar in untreated and Slit2 treated mice (30 min, vehicle vs. Slit2: $5.6 \times 10^4$ vs $5.6 \times 10^4$; 24 h, vehicle vs. Slit2-$29.6 \times 10^4$ vs. $27.7 \times 10^4$; 48 h vehicle vs. Slit2 $2596.7 \times 10^4$ vs. $2436 \times 10^4$). These results demonstrate that pre-treatment with Slit2 does not impair immunity.

The present results showed that Slit2 does not impair important neutrophil immune functions, namely phagocytosis and superoxide production. To further explore the effect of Slit2 on immune function in vivo, the mouse model of *Listeria* infection was used and bacterial colony counts were measured 30 minute, 24 hour and 48 hour post *Listeria* injection in mice pre-treated with Slit2. The bacterial colony counts were similar in Untreated and Slit2 treated mice (30 min, vehicle vs. Slit2: $5.6×10^4$ vs $5.6×10^4$; 24 h, vehicle vs. Slit2-$29.6×10^4$ vs. $27.7×10^4$; 48 h vehicle vs. Slit2 $2596.7×10^4$ vs. $2436×10^4$ FIG. 31). These results demonstrate that pre-treatment with Slit2 does not impair immunity.

Discussion

Acute kidney injury is a complex, life threatening illness defined by the presence of reduced glomerular filtration rate and azotemia (Star 1998). AKI leads to high morbidity and mortality in hospitalized patients (Xue, Daniels et al. 2006). Moreover, evidence from large databases of US hospitalizations indicates that there has been a marked increase in rates of AKI over past 10-15 years perhaps due to the increasing age and co-morbidities in patients who develop AKI (Hou, Bushinsky et al. 1983; Nash, Hafeez et al. 2002; Xue, Daniels et al. 2006).

There have been tremendous advances in the understanding of pathophysiology of AKI (Bonventre and Zuk 2004). Ischaemia reperfusion injury is the leading cause of AKI in both native and allograft kidney (Star 1998; Devarajan 2006). Reduced blood flow and oxygen delivery leads to ATP depletion which in turn leads to epithelial and endothelial dysfunction, cell swelling and cell death (Okusa 2002; Legrand, Mik et al. 2008). This induces renal synthesis or activation of pro-inflammatory cytokines and chemokines and leads to recruitment of leukocytes to the kidneys (Friedewald and Rabb 2004). The recruited leukocytes particularly neutrophils then aggravate the inflammatory damage leading not only to acute tissue injury but also to long term fibrosis and dysfunction (Gueler, Gwinner et al. 2004).

Neutrophils are important mediators of renal injury in IRI and studies have clearly shown increased neutrophil accumulation in renal IRI (Paller 1989; Caramelo and Alvarez Arroyo 1998; Awad, Rouse et al. 2009). Furthermore therapies targeting neutrophil adhesion molecules and neutrophil depletion are protective in mouse AKI models (Kelly, Williams et al. 1994; Singbartl, Green et al. 2000; Nemoto, Burne et al. 2001; Kato, Yuzawa et al. 2009). However, given the diversity in molecular migration cues and the cells recruited these therapies have not been entirely successful and treatment of AKI remains mainly supportive (Salmela, Wramner et al. 1999). Therefore a global chemorepellant is a better therapeutic strategy.

The secreted glycoprotein, Slit2, was originally described in *Drosophila* as a neuronal and axonal repellent during central nervous system development (Kidd, Brose et al. 1998; Brose, Bland et al. 1999; Kidd, Bland et al. 1999). Since its initial discovery it has been shown that Slit2 is expressed on multiple leukocyte subsets (T cells, monocytes, neutrophils, dendritic cells) and it inhibits chemotaxis of these leukocytes via its action on small Rho GTPases Rac and Cdc 42 (Guan, Zu et al. 2003; Prasad, Qamri et al. 2007; Tole, Mukovozov et al. 2009). However its effect on neutrophil adhesion and transendothelial migration remain unknown. In the present study, it was demonstrated that Slit2 was effective in inhibiting neutrophil adhesion to endothelium stimulated with TNF-α. Furthermore neutrophil adhesion was significantly reduced in endothelium exposed to SI/R injury by pre-treatment with Slit2. This is in keeping with results by Prasad et al who demonstrated that Slit2 reduced Tcell and monocyte adhesion (Prasad, Qamri et al. 2007). Early after reperfusion, platelets also adhere within capillaries of the vasa recta. After adhering, platelets become activated, spread, and release acute inflammatory mediators and pro-fibrotic growth factors that intensify kidney injury and scarring (Li, L and Okusa, M D 2006.). Therapies that inhibit platelet function also partially, but not completely, ameliorate AKI (Singbartl 2000; Chintala M S et al 1994).

Materials and Methods

Chemicals and Reagents

Unless otherwise stated, reagents were purchased from Sigma-Aldrich (St. Louis, Mo., USA). Polymorphprep neutrophil separation medium was purchased from Axis-Shield (Norway). Transwell inserts were bought from Corning Costar:

Slit2 Expression and Purification

Production of full length human Slit2 was carried as previously described (Soumu). The purity of Slit2 preparation was determined and levels of endotoxin were measured as previously described (Tole, Mukovozov et al. 2009). Truncated N-terminal fragment of mouse Slit2 (N-Slit2) was purchased from R&D systems, Minneapolis, USA. In some experiments, full length was purified by affinity purification.

Isolation of Primary Human Neutrophils

Human whole blood was obtained from healthy volunteers, and neutrophils were isolated using the Polymorphprep gradient separation as previously described (Tole, Mukovozov et al. 2009). Prior to use, the neutrophils were resuspended in HBSS containing 1 mM $CaCl_2$ and 1 mM $MgCl_2$. Experiments were performed within 1-2 h of isolation of neutrophils (Tole, Mukovozov et al. 2009).

Neutrophil Endothelial Adhesion Assays

Freshly isolated human neutrophils were labelled with calcein and were incubated with medium alone or full length Slit2 (4.5 µg/ml) for 10 minutes (Tole, Mukovozov et al. 2009). Neutrophils ($10^5$ cells/well) were incubated with confluent endothelial monolayer and allowed to adhere for 30 minutes (Foreman, Vaporciyan et al. 1994). Non-adherent cells were then removed by centrifuging the 96 well plates upside down at 100 g for 1 minute. Neutrophil adhesion was quantified using the fluorescent plate reader at excitation and emission wavelengths of 494 and 517 nm. All experiments were carried out in triplicate.

RNA Isolation and Analysis of Human Robo Isoforms by Reverse Transcriptase-Polymerase Chain Reaction (RT-PCR)

Total RNA was isolated from HUVEC cells by using one-step RNA reagent (BIO BASIC INC) following manufacturer's instruction. RT-PCR analysis was processed using QIAGEN one-step RT-PCR kit (QIAGEN) with 1 mg of total RNA and using gene specific primers for the first-strand DNA synthesis and following PCR amplification. The primers for human Robo 1-4 and corresponding RT-PCR product sizes are summarized in table 1. The primers span 2-3 axons to insure the right sizes for transcripts. Reaction mixtures were subjected to the following amplification protocols: reverse transcription for 30 min at 55° C., initiate PCR activation for 15 min at 95° C., and 40 cycles at 94° C. for 30 sec, at 60° C. for 1 min (58 C. for Robo 2) and at 72° C. for 1 min. PCR products were separated by 1.5% agarose gel electrophoresis.

Simulated Ischaemia/Reperfusion Injury of Endothelial Cells (SI/R)

For inducing SI/R, human umbilical venous endothelial cells (HUVEC, passage 3-8) were grown in EBM-2 and maintained at 37° C. in a standard incubator at room air oxygen tension (21% oxygen; designated normoxia). Hypoxic conditions were induced by exposing cells to 1% oxygen, balance nitrogen at 37° C. Medium was replaced with HBSS at the start of the hypoxic exposure (Arnould, Michiels et al. 1994). Chamber $PO_2$ was calibrated and monitored during the entire experiment using Proox 110 (Biospherix, USA) oxygen controller system. After a 60-minute period of hypoxia, re-oxygenation was initiated replacing medium with EBM-2 under normoxic conditions for variable periods ranging from 30 to 180 minutes. In some wells, HUVEC were incubated TNF-α (20 ng/ml) for 4-6 hrs.

The MTT [3-(4,5-Dimethylthiazol-2-yl)-2,5-Diphenyltetrazolium Bromide] Cell Viability Assay MTT assay was performed as per manufacturer's instructions (Pieters, Huismans et al. 1988). Normoxic cells and cells exposed to staurosporin were used as negative and positive controls respectively. Mitochondrial dehydrogenases of viable cells cleave the tetrazolium ring, yielding purple formazan crystals which are insoluble in aqueous solutions. The crystals were dissolved in acidified isopropanol and spectrophometrically measured at $OD_{570}$. All experiments were carried out in triplicate.

Neutrophil Adhesion Under Hydrodynamic Shear Flow Conditions

HUVEC were grown to confluence in fibronectin coated channels of the Bioflux microfluidic system (Fluxion Biosciences, CA). HUVEC were incubated with TNF-α (20 ng/ml for 4 hrs). Calcein labelled human neutrophils ($3 \times 10^5$/well) were pre-incubated with Slit2 (4.5 µg/ml) for 10 minutes, then perfused through the channels at shear rate of 1.0 dynes/$cm^2$ (Yang, Kowalski et al. 2006). Temperature was maintained at 37° C. A Nikon TE2000 inverted microscope and Hamamatsu video camera was used to video record neutrophil-HUVEC interaction. Sequential images were taken every 6 seconds for 15 minutes in a representative field, and at the end of 15 minutes, 4 additional fields were recorded (each field/30 seconds). Neutrophil adhesion was quantified with Bioflux Montage software.

Neutrophil Transmigration Assay

HUVECS were grown to confluence on fibronectin (50 µg/ml) coated polyester transwell inserts (diameter, 6.5 mm; pore size, 3 µm, Corning Costar) at a concentration of $2.5 \times 10^4$ cells/insert in 200 µl of EBM 2 media. The inserts were then placed in a 24-well plate, in which each well contained 700 µl medium. Freshly isolated, human neutrophils ($5 \times 10^6$ cells/ml) were labelled with calcein, then incubated with Slit2 (4.5 µg/ml) for 10 minutes. Thereafter the 100 µl neutrophils were placed in the upper well of the transwell chamber and chemokine interleukin 8 (IL-8, 50 ng/ml) added to the lower well (Bayat, Werth et al. 2010). Neutrophils were allowed to migrate for 3 h at 37° C. and 5% $CO_2$. At the end of 3 hours the neutrophil which had migrated in lower well were permealised with 1% Triton and transferred in triplicate in 96 well plate (100 µl/well). The fluorescence emitted was read with fluorescent plate reader at excitation and emission wavelengths of 494 nm and 517 nm respectively.

Mouse Model of Renal Ischemia-Reperfusion Injury

Experiments were performed as previously described (Li, Huang et al. 2007; Li, Huang et al. 2008; Awad, Rouse et al. 2009; Li, Huang et al. 2010). All animals were handled and procedures were performed in adherence to the National Institutes of Health *Guide for the Care and Use of Laboratory Animals*, and all protocols were approved by the University of Virginia Institutional Animal Care and Use Committee.

Male C57BL/6 mice (8-12 weeks of age, Charles River Laboratories, Wilmington, Mass., USA) were subjected to bilateral IRI (26 mins ischemia then 24 hrs reperfusion) as previously described (Li, Huang et al.; Li, Huang et al. 2007; Li, Huang et al. 2008). Control, sham-operated mice underwent a similar procedure, however the renal pedicles were not clamped. Mice were injected with full length Slit2 or truncated N-terminal Slit2 (2 µg) or vehicle (i.p.) one hour prior to IRI.

Assessment of Kidney Function

Plasma creatinine was determined using a colorimetric assay according to the manufacturer's protocol (Sigma Aldrich).

Flow Cytometry Analysis

Flow cytometry was used to analyze kidney leukocyte content. In brief, kidneys were extracted, minced, digested, and then passed through a filter and a cotton column as previously described (Li, Huang et al. 2007). After blocking nonspecific Fc binding with anti-mouse CD16/32 (2.4G2), fresh kidney suspensions were incubated with fluorophore-tagged anti-mouse CD45 (30-F11) to determine total leukocyte cell numbers. CD45-labeled samples were further used for labelling with different combinations of anti-mouse F4/80-APC (BM8), GR-1-FITC (Ly6G), CD11b-PE, CD11c-APC and IA-PE (MHCII). 7-AAD (BD Biosciences) was added 15 mins before analyzing the sample to separate live from dead cells (Li, Huang et al.; Li, Huang et al. 2007). Appropriate fluorochrome-conjugated, isotype-matched, irrelevant mAbs were used as negative controls. Subsequent flow cytometry data acquisition was performed on FACS Calibur (Becton Dickinson). Data was analyzed by FlowJo software 6.4 (Tree Star). All antibodies (except as noted) were purchased from eBioscience and were used at a concentration of 5 µg/ml.

Neutrophil Phagocytosis Assay

Neutrophil phagocytosis was performed as previously described with minor modifications (Yan, Di Clano-Oliveira et al. 2007). Briefly, 3.8 µm latex beads were coated with human IgG (1 mg/ml) for 2 hours at room temperature. Neutrophils pre-incubated myc-affinity purified Slit2 (600 ng/ml) or control medium (equal volume) for 10 minutes were exposed to opsonised latex beads, rapidly centrifuged (1000 rpm for 30 s) to initiate phagocytosis, and plated onto fibronectin-coated coverslips. Phagocytosis was terminated after 30 min and external beads were labelled on ice using antihuman Cy2 conjugated secondary Ab. Slit2 or control medium were present throughout the course of phagocytosis. Images were taken of at least 10 random fields using a Leica deconvolution microscope. The number of ingested particles was analyzed by counting total beads using DIC and subtracting the number of external, labelled beads. Two measures were used to assess phagocytosis: 1) Phagocytic index (# ingested beads/#cells). 2) % of neutrophils with at least 1 ingested bead.

Neutrophil Superoxide Production Assay

Superoxide production was assayed by measuring the superoxide dismutase inhibitable reduction of cytochrome c (Yan, Di Clano-Oliveira et al. 2007). Briefly, neutrophils ($2.5\times10^5$ cells) were incubated with Slit2 (600 ng/ml) or control media and suspended in PBS supplemented with divalent cations and glucose and incubated with cytochrome c (75 µM)±SOD (60 µg/ml). The cells were then stimulated with PMA (2 µM) or fMLP (1 µM) and cytochrome c reduction was assayed by measuring absorbance at 550 nm using a VersaMax microplate reader (Molecular Devices, Sunnyvale, Calif.) in kinetic mode for 20 minutes, acquiring every 15 seconds.

Mouse Listeria Infection Model

Six to eight week old C57BL/6J mice were purchased from Jackson Laboratory. Slit2 (2 µg/mice) or control vehicle was delivered via intravenous (i.v.) injections in the lateral tail vein. Wild type Listeria monocytogenes $5\times10^4$ CFU in 200 µl of PBS was injected intravenously one hour later. Mice were sacrificed at indicated time points and the livers were obtained. The left lobes were homogenized in sterile PBS for CFU quantification from serial dilutions on BHI-agar plates.

Statistical Analysis

SPSS statistical software (Version 19.0) was used to analyze the data. Data were analyzed using 2-tailed t test or 1- or 2-way ANOVA with post-hoc analysis as appropriate. $p<0.05$ was used to indicate significance.

Example 4

Slit2 Prevention of Vascular Inflammation, Neointimal Proliferation and Thrombosis In Vivo To directly test Slit2's effects in the context of vascular injury, 2 experimental models are used. The first model, a murine model of arterial denudation injury, produces acute vascular inflammation and long-term neointimal proliferation. The second model, namely ferric chloride-induced arterial injury, provokes acute thrombosis. For all of the in vivo experiments below, multiple doses of full-length Slit2 and truncated N-Slit2 are tested to determine which dose produces optimal effects.

For both of these studies, the same mouse model of carotid artery injury is used. The left common carotid artery is subjected to wire denudation injury, while the right carotid artery is left intact. After 48 h, vascular inflammation accompanied by monocyte and neutrophil infiltration is maximal (You et al. 2003, Zaidi et al. 2000). Within 10-14 days, neointimal proliferative lesions develop and arterial remodeling occurs due to uncontrolled migration and proliferation of medial and adventitial VSMC (You et al. 2003, Zaidi et al. 2000). Building on the preliminary results, full-length Slit2, truncated N-Slit2, or vehicle alone, is administered locally at the time of injury, or intravenously by tail vein injection 1 d prior to inducing arterial injury and every 3 d thereafter (FIGS. 12 & 15) (Tole et al. 2009). Carotid artery tissue sections harvested on Day 2 are histologically examined to assess the degree of inflammation present. Immunohistochemistry is performed using Ab detecting markers of monocytes/macrophages, neutrophils, T lymphocytes, B lymphocytes, and natural killer cells (Mannon et al. 1999). In the second set of experiments, carotid artery tissues are harvested on Day 14, histology is examined, and immunolabeling of sections is performed using anti-α-smooth muscle actin Ab to detect VSMC. Slit2's effects on neointimal proliferation are assessed by comparing the intima/media ratios from injured arteries of vehicle control-treated and Slit2-treated mice (You et al. 2003, Zaidi et al. 2000). The specificity of any observed Slit2-induced responses is verified using Robo-N.

Tail bleeding assay results show that Slit2 inhibits platelet function in vivo (FIG. 23) (Jones et al. 2008). To test Slit2 in a context that mimics the acute thrombosis that precedes stroke or myocardial infarction, a mouse model of ferric chloride-induced arterial injury is used (Fay et al. 1999, Kerlin et al. 2004). The right carotid artery is left intact and the left is exposed by blunt dissection and a Doppler flow probe is positioned around the distal end of the artery to measure blood flow. Ten minutes later, a strip of filter paper soaked in 20% ferric chloride is applied to the adventitial aspect of the artery for 1 minute. The experimental field is flushed with saline and Doppler blood flow is continuously monitored. The time to vessel occlusion, a direct reflection of the degree of vascular thrombosis, is the time at which Doppler flow falls to 25% of the initial flow. The ability of full-length or truncated Slit2 to inhibit thrombus formation is tested by comparing the time to occlusion in control vehicle-treated mice to that of mice treated with Slit2. Function-blocking Robo-N is used to verify the specificity of Slit2's observed actions.

Because Slit2 prevents recruitment of leukocytes and VSMC, and has anti-platelet functions, it is a useful agent for preventing in-stent restenosis. In the clinical setting, in-stent restenosis results not just from one of these pathologic processes, but from all three together. Coronary artery stents are coated with full-length Slit2 and truncated N-Slit2 using a plasma reactor (Kutryk et al. 2007). A porcine model of coronary artery in-stent restenosis is used, which most closely resembles the disease process in humans, to determine that Slit2 slows the rate at which stents restenose (Kutryk et al. 2007). Since homology of Slit2 is conserved across species ranging from Drosophila to mice to humans, the human Slit2 preparations are expected to be effective in pigs. Indeed, recombinant human Slit2 works well in rodent models of inflammation (Tole et al. 2009, Kanellis et al. 2004, Jones et al. 2008). For studies examining in-stent restenosis, Slit2 is administered: 1) by intravenous injection, or 2) by pre-coating stents with endothelial cells that continuously produce Slit2. A lentiviral expression system is optimized to allow sustained high-level production of Slit2 by pig arterial endothelial cells (Robinson et al. 1998). For all experiments, stents are examined at 7 d (when inflammatory cell infiltration peaks) and at 28 d (when neointimal proliferation occurs) (Kutryk et al. 2007).

It is expected that Slit2 prevents vascular inflammation, VSMC recruitment, (Tole et al. 2009, Kanellis et al. 2004) and thrombosis in vivo. The leucine rich and epidermal growth factor-like repeats of Slit2 allow local binding to the extracellular matrix and facilitate slow release of Slit2 (Ronca et al. 2001). The two Slit2 preparations, c-myc- and His-tagged, respectively, permit the distinction between endogenous and exogenous Slit2 by immunofluorescent labeling and immunoblotting, using anti-Slit2, anti-myc, and anti-His Ab.

To test the ability of Slit2 to prevent both injurious and reparative responses following vascular injury, the effects of Slit2 on vascular injury/repair following balloon injury in porcine models is tested, and the ability of Slit2 to promote or inhibit wound healing in vivo, is tested using a well-established porcine model (Sullivan et al. 2001).

In the clinical setting of vascular injury, Slit2 is instilled acutely at the site of balloon angioplasty and in a sustained manner by coating it on a vascular stent. In these scenarios, Slit2 is immobilized and, thus, does not adversely affect systemic immunity. Even if acute administration at the site of angioplasty resulted in some systemic release of Slit2, effects on immunity are transient. Nonetheless, it is important to optimize Slit2 dosing to produce maximal clinical benefit while avoiding potential adverse effects such as immunosuppression or bleeding.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| | base | PCR product size (bp) | exon spanning |
|---|---|---|---|
| h-Robo1-F SEQ ID NO: 1 CTATCGGCCATCTGGAGCCAAC | 22 | 410 | 15 to 17 |
| h-Robo1-R SEQ ID NO: 2 GGAACAAGAAAGGGAATGACCACG | 24 | | |
| h-Robo2-F SEQ ID NO: 3 CAACTGGAGACCTCACAATCACC | 23 | 310 span exon 8-9 | 8 to 9 |
| h-Robo2-R SEQ ID NO: 4 GTGCCTTGCTCTTGAATTGTTGC | 23 | | |
| h-Robo3-F SEQ ID NO: 5 ATCACGATCCGTGGAGGGAAGC | 22 | 316 if+ intron 4-5 is 709 bp | 4 to 6 |
| h-Robo3-R SEQ ID NO: 6 TCATCTTCGGCACTCACATGC | 21 | | |
| h-Robo4-F SEQ ID NO: 7 AGACCCACACCACCTCCTGCC | 21 | 231 if+ intron 2-3 is 492 bp | 2 to 3 |
| h-Robo4-R SEQ ID NO: 8 TAAACTGCTCACCCACCACAGC | 22 | | |

REFERENCES

Aasheim, H.-C., J. Delabie, et al. (2005). "Ephrin-A1 binding to CD4+ T lymphocytes stimulates migration and induces tyrosine phosphorylation of PYK2." *Blood* 105(7): 2869-2876.

Afroze, T., Yang, L., Wang, C., Gros, R., Kalair, W., Hoque, A., Mungrue, I., Zhu, Z., and Husain, M. 2003. Calcineurin-dependent regulation of plasma membrane Ca2+ ATPase-4 in the vascular smooth muscle cell cycle. *Am J Physiol Cell Physiol* 285:88-95.

Ambruso, D. R., C. Knall, et al. (2000). "Human neutrophil immunodeficiency syndrome is associated with an inhibitory Rac2 mutation." *Proc Natl Acad Sci USA* 97(9): 4654-9.

Arnould, T., C. Michiels, et al. (1994). "Hypoxic human umbilical vein endothelial cells induce activation of adherent polymorphonuclear leukocytes." *Blood* 83(12): 3705-16.

Awad, A. S., M. Rouse, et al. (2009). "Compartmentalization of neutrophils in the kidney and lung following acute ischemic kidney injury." *Kidney Int* 75(7): 689-98.

Bashaw, G. J., T. Kidd, et al. (2000). "Repulsive axon guidance: Abelson and Enabled play opposing roles downstream of the roundabout receptor." *Cell* 101(7): 703-15.

Bagshaw, S. M. (2006). "The long-term outcome after acute renal failure." *Curr Opin Crit Care* 12(6): 561-6.

Bayat, B., S. Werth, et al. (2010). "Neutrophil transmigration mediated by the neutrophil-specific antigen CD177 is influenced by the endothelial S536N dimorphism of platelet endothelial cell adhesion molecule-1." *J Immunol* 184 (7): 3889-96.

Bochner, B. S., F. W. Luscinskas, et al. (1991). "Adhesion of human basophils, eosinophils, and neutrophils to interleukin 1-activated human vascular endothelial cells: contributions of endothelial cell adhesion molecules." *J Exp Med* 173(6): 1553-7.

Bonventre, J. V. and A. Zuk (2004). "Ischemic acute renal failure: an inflammatory disease?" *Kidney Int* 66(2): 480-5.

Boring, L., J. Gosling, et al. (1998). "Decreased lesion formation in CCR2−/− mice reveals a role for chemokines in the initiation of atherosclerosis." *Nature* 394(6696): 894-7.

Boyd, A. W., S. O. Wawryk, et al. (1988). "Intercellular adhesion molecule 1 (ICAM-1) has a central role in cell-cell contact-mediated immune mechanisms." *Proc Natl Acad Sci USA* 85(9): 3095-9.

Brady, H. R. and G. G. Singer (1995). "Acute renal failure." *Lancet* 346(8989): 1533-40.

Brose, K., K. S. Bland, et al. (1999). "Slit proteins bind Robo receptors and have an evolutionarily conserved role in repulsive axon guidance." *Cell* 96(6): 795-806.

Caramelo, C. and M. V. Alvarez Arroyo (1998). "Polymorphonuclear neutrophils in acute renal failure: new insights." *Nephrol Dialysis Transplant* 13(9): 2185-8.

Caron, E. and A. Hall (1998). "Identification of two distinct mechanisms of phagocytosis controlled by different Rho GTPases." *Science* 282(5394): 1717-21.

Chen, J., S. De, et al. (2004). "Impaired platelet responses to thrombin and collagen in AKT-1-deficient mice." *Blood* 104(6): 1703-10.

Chintala M S et al 1994 JPET 271:1203-1208.

Cho, J., B. C. Furie, et al. (2008). "A critical role for extracellular protein disulfide isomerase during thrombus formation in mice." *J Clin Invest* 118(3): 1123-31.

Combadiere, C., S. Potteaux, et al. (2003). "Decreased atherosclerotic lesion formation in CX3CR1/apolipoprotein E double knockout mice." *Circulation* 107(7): 1009-16.

Devarajan, P. (2006). "Update on mechanisms of ischemic acute kidney injury." *J Am Soc Nephrol* 17(6): 1503-20.

Fay, W., Parker, A., Ansari, M., Zheng, X., and Ginsburg, D. 1999. Vitronectin inhibits the thrombotic response to arterial injury in mice. *Blood* 93:1825-1830.

Fiorina, P., M. J. Ansari, et al. (2006). "Role of CXC chemokine receptor 3 pathway in renal ischemic injury." *J Am Soc Nephrol* 17(3): 716-23.

Foreman, K. E., A. A. Vaporciyan, et al. (1994). "C5a-induced expression of P-selectin in endothelial cells." *J Clin Invest* 94(3): 1147-55.

Friedewald, J. J. and H. Rabb (2004). "Inflammatory cells in ischemic acute renal failure." *Kidney Int* 66(2): 486-91.

Furuichi, K., T. Wada, et al. (2003). "CCR2 signaling contributes to ischemia-reperfusion injury in kidney." *J Am Soc Nephrol* 14(10): 2503-15.

Gawaz, M. (2008). "The evolving science of atherothrombotic disease." *European Heart Journal Supplements* 10(suppl I): 14.

Gawaz, M., H. Langer, et al. (2005). "Platelets in inflammation and atherogenesis." *J Clin Invest* 115(12): 3378-84.

Gosling, J., S. Slaymaker, et al. (1999). "MCP-1 deficiency reduces susceptibility to atherosclerosis in mice that overexpress human apolipoprotein B." *J Clin Invest* 103(6): 773-8.

Guan, H., G. Zu, et al. (2003). "Neuronal repellent Slit2 inhibits dendritic cell migration and the development of immune responses." *J Immunol* 171(12): 6519-26.

Gueler, F., W. Gwinner, et al. (2004). "Long-term effects of acute ischemia and reperfusion injury." *Kidney Int* 66(2): 523-7.

Hagberg, I. A. and T. Lyberg (2000). "Blood platelet activation evaluated by flow cytometry: optimised methods for clinical studies." *Platelets* 11(3): 137-50.

Hall, K. T., L. Boumsell, et al. (1996). "Human CD100, a novel leukocyte semaphorin that promotes B-cell aggregation and differentiation." *Proc Natl Acad Sci USA* 93(21): 11780-5.

Hartwig, J. H., S. Kung, et al. (1996). "D3 phosphoinositides and outside-in integrin signaling by glycoprotein IIb-IIIa mediate platelet actin assembly and filopodial extension induced by phorbol 12-myristate 13-acetate." *J Biol Chem* 271(51): 32986-93.

Hjorthaug, H. S, and H. C. Aasheim (2007). "Ephrin-Al stimulates migration of CD8+CCR7+ T lymphocytes." *Eur J Immunol* 37(8): 2326-36.

Hou, S. H., D. A. Bushinsky, et al. (1983). "Hospital-acquired renal insufficiency: a prospective study." *Am J Med* 74(2): 243-8.

Huo, Y., A. Schober, et al. (2003). "Circulating activated platelets exacerbate atherosclerosis in mice deficient in apolipoprotein E." *Nat Med* 9(1): 61-7.

Jackson, S. P., C. L. Yap, et al. (2004). "Phosphoinositide 3-kinases and the regulation of platelet function." *Biochem Soc Trans* 32(Pt 2): 387-92.

Jo, S. K., M. H. Rosner, et al. (2007). "Pharmacologic treatment of acute kidney injury: why drugs haven't worked and what is on the horizon." *Clin J Am Soc Nephrol* 2(2): 356-65.

Jo, S. K., S. A. Sung, et al. (2006). "Macrophages contribute to the initiation of ischaemic acute renal failure in rats." *Nephrol Dialysis Transplant* 21(5): 1231-9.

Jones, C. A., Londin, N. R., Chen, H., Park, K. W., Sauvaget, D., Stockton, R. A., Wythe, J. D., Suh, W., Larrieu-Lahargue, F., Mukoutama, Y.-s., et al. 2008. Robo4 stabilizes the vascular network by inhibiting pathologic angiogenesis and endothelial hyperpermeability. *Nat Med* 14:448-453.

Jones, D. A., L. V. McIntire, et al. (1994). "A two-step adhesion cascade for T cell/endothelial cell interactions under flow conditions." *J Clin Invest* 94(6): 2443-50.

Jones, S., Tucker, K. L., Kaiser, W. J., Barrett, N. E., Lowry, P. J., Zimmer, A., Hunt, S. P., Emerson, M., and Gibbins, J. M. 2008. Peripheral tachykinins and the neurokinin receptor NK1 are required for platelet thrombus formation. *Blood* 111:605-612.

Kandel, E. S. and N. Hay (1999). "The regulation and activities of the multifunctional serine/threonine kinase Akt/PKB." *Exp Cell Res* 253(1): 210-29.

Kanellis, J., G. E. Garcia, et al. (2004). "Modulation of inflammation by slit protein in vivo in experimental crescentic glomerulonephritis." *Am J Pathol* 165(1): 341-52.

Kashiwagi, H., M. Shiraga, et al. (2005). "Negative regulation of platelet function by a secreted cell repulsive protein, semaphorin 3A." *Blood* 106(3): 913-21.

Kato, N., Y. Yuzawa, et al. (2009). "The E-selectin ligand basigin/CD147 is responsible for neutrophil recruitment in renal ischemia/reperfusion." *J Am Soc Nephrol* 20(7): 1565-76.

Kelly, K. J., W. W. Williams, Jr., et al. (1994). "Antibody to intercellular adhesion molecule 1 protects the kidney against ischemic injury." *Proceedings of the National Academy of Sciences of the United States of America* 91(2): 812-6.

Kerlin, B., Cooley, B., Isermann, B., Hernandez, I., Sood, R., Zogg, M., Hendrickson, S., Mosesson, M., Lord, S., and Weiler, H. 2004. Cause-effect relation between hyperfibrinoginemia and vascular disease. *Blood* 103:1728-1734.

Kidd, T., K. S. Bland, et al. (1999). "Slit is the midline repellent for the robo receptor in Drosophila." *Cell* 96(6): 785-94.

Kidd, T., K. Brose, et al. (1998). "Roundabout controls axon crossing of the CNS midline and defines a novel subfamily of evolutionarily conserved guidance receptors." *Cell* 92(2): 205-15.

Kim, C. and M. C. Dinauer (2001). "Rac2 is an essential regulator of neutrophil nicotinamide adenine dinucleotide phosphate oxidase activation in response to specific signaling pathways." *J Immunol* 166(2): 1223-32.

Kirk, R. I., M. R. Sanderson, et al. (2000). "Threonine phosphorylation of the beta 3 integrin cytoplasmic tail, at a site recognized by PDK1 and Akt/PKB in vitro, regulates Shc binding." *J Biol Chem* 275(40): 30901-6.

Klagsbrun, M. and A. Eichmann (2005). "A role for axon guidance receptors and ligands in blood vessel development and tumor angiogenesis." *Cytokine Growth Factor Rev* 16(4-5): 535-48.

Korkeila, M., E. Ruokonen, et al. (2000). "Costs of care, long-term prognosis and quality of life in patients requiring renal replacement therapy during intensive care." *Intensive Care Med* 26(12): 1824-31.

Kovacsovics, T. J., C. Bachelot, et al. (1995). "Phosphoinositide 3-kinase inhibition spares actin assembly in activating platelets but reverses platelet aggregation." *J Biol Chem* 270(19): 11358-66.

Kroll, M. (2001). Mechanisms of Coagulation. *Manual of coagulation disorders*. M. Kroll. Massachusetts, Wiley-Blackwell: 1-8.

Kuijpers, M. J., V. Schulte, et al. (2003). "Complementary roles of glycoprotein VI and alpha2beta1 integrin in collagen-induced thrombus formation in flowing whole blood ex vivo." *FASEB J* 17(6): 685-7.

Kumanogoh, A., T. Shikina, et al. (2005). "Nonredundant roles of Sema4A in the immune system: defective T cell priming and Th1/Th2 regulation in Sema4A-deficient mice." *Immunity* 22(3): 305-16.

Kutryk, M. J., Kuliszewski, M. A., Jaffe, R., Tio, F. O., Janicki, C., L., S. W., Sparkes, J. D., and Strauss, B. H. 2007. Low-energy gamma-emitting stents inhibit intimal hyperplasia with minimal "edge effects" in a pig coronary artery model. *Cardiovasc Revasc Med* 8:28-37.

Lai, C. F., L. Chaudhary, et al. (2001). "Erk is essential for growth, differentiation, integrin expression, and cell function in human osteoblastic cells." *J Biol Chem* 276(17): 14443-50.

Legrand, M., E. G. Mik, et al. (2008). "Renal hypoxia and dysoxia after reperfusion of the ischemic kidney." *Mol Med* 14(7-8): 502-16.

Lesnik, P., C. A. Haskell, et al. (2003). "Decreased atherosclerosis in CX3CR1−/− mice reveals a role for fractalkine in atherogenesis." *J Clin Invest* 111(3): 333-40.

Li, L., L. Huang, et al. (2007). "NKT cell activation mediates neutrophil IFN-gamma production and renal ischemia-reperfusion injury." *J Immunol* 178(9): 5899-911.

Li, L., L. Huang, et al. (2008). "The chemokine receptors CCR2 and CX3CR1 mediate monocyte/macrophage trafficking in kidney ischemia-reperfusion injury." *Kidney Int* 74(12): 1526-37.

Li, L., L. Huang, et al. "IL-17 produced by neutrophils regulates IFN-gamma-mediated neutrophil migration in mouse kidney ischemia-reperfusion injury." *J Clin Invest* 120(1): 331-42.

Li, L., L. Huang, et al. (2010). "IL-17 produced by neutrophils regulates IFN-gamma-mediated neutrophil migration in mouse kidney ischemia-reperfusion injury." *J Clin Invest* 120(1): 331-42.

Li, L and Okusa, M D 2006. Nat Clin Pract Nephr 2:432-444.

Li, Z., G. Zhang, et al. (2006). "Sequential activation of p38 and ERK pathways by cGMP-dependent protein kinase leading to activation of the platelet integrin alphaIIb beta3." *Blood* 107(3): 965-72.

Libby, P. (2002). "Inflammation in atherosclerosis." *Nature* 420(6917): 868-74.

Licht, C., F. G. Pluthero, et al. (2009). "Platelet-associated complement factor H in healthy persons and patients with atypical HUS." *Blood* 114(20): 4538-45.

Liu, D., J. Hou, et al. (2006). "Neuronal chemorepellent Slit2 inhibits vascular smooth muscle cell migration by suppressing small GTPase Rac1 activation." *Circ Res* 98(4): 480-9.

Lo, B., L. Li, et al. (2005). "Requirement of VPS33B, a member of the Sec1/Munc18 protein family, in megakaryocyte and platelet alpha-granule biogenesis." *Blood* 106(13): 4159-66.

Lyck, R., Y. Reiss, et al. (2003). "T-cell interaction with ICAM-1/ICAM-2 double-deficient brain endothelium in vitro: the cytoplasmic tail of endothelial ICAM-1 is necessary for transendothelial migration of T cells." *Blood* 102(10): 3675-83.

Mannon, R., Kopp, J., Ruiz, P., Griffiths, R., Bustos, M., Platt, J., Klotman, P., and Coffman, T. 1999. Chronic rejection in mouse kidney allografts. *Kidney Int* 55:1935-1944.

Massberg, S., K. Brand, et al. (2002). "A critical role of platelet adhesion in the initiation of atherosclerotic lesion formation." *J Exp Med* 196(7): 887-96.

Mazharian, A., S. Roger, et al. (2007). "Protease-activating receptor-4 induces full platelet spreading on a fibrinogen matrix: involvement of ERK2 and p38 and Ca2+ mobilization." *J Biol Chem* 282(8): 5478-87.

McCarty, O. J., M. K. Larson, et al. (2005). "Rac1 is essential for platelet lamellipodia formation and aggregate stability under flow." *J Biol Chem* 280(47): 39474-84.

McCarty, O. J., Y. Zhao, et al. (2004). "Evaluation of the role of platelet integrins in fibronectin-dependent spreading and adhesion." *J Thromb Haemost* 2(10): 1823-33.

Meadows, T. A. and D. L. Bhatt (2007). "Clinical aspects of platelet inhibitors and thrombus formation." *Circ Res* 100(9): 1261-75.

Moroi, M., S. M. Jung, et al. (1996). "Analysis of platelet adhesion to a collagen-coated surface under flow conditions: the involvement of glycoprotein VI in the platelet adhesion." *Blood* 88(6): 2081-92.

Nash, K., A. Hafeez, et al. (2002). "Hospital-acquired renal insufficiency." *Am Kidney Dis* 39(5): 930-6.

Nemoto, T., M. J. Burne, et al. (2001). "Small molecule selectin ligand inhibition improves outcome in ischemic acute renal failure." *Kidney Int* 60(6): 2205-14.

Okusa, M. D. (2002). "The inflammatory cascade in acute ischemic renal failure." *Nephron* 90(2): 133-8.

Osborn, L., C. Hession, et al. (1989). "Direct expression cloning of vascular cell adhesion molecule 1, a cytokine-induced endothelial protein that binds to lymphocytes." *Cell* 59(6): 1203-11.

Paller, M. S. (1989). "Effect of neutrophil depletion on ischemic renal injury in the rat." *J Lab & Clin Med* 113(3): 379-86.

Pieters, R., D. R. Huismans, et al. (1988). "Adaptation of the rapid automated tetrazolium dye based (MTT) assay for chemosensitivity testing in childhood leukemia." *Cancer Lett* 41(3): 323-32.

Pleines, I., A. Eckly, et al. (2010). "Multiple alterations of platelet functions dominated by increased secretion in mice lacking Cdc42 in platelets." *Blood* 115(16): 3364-73.

Prasad, A., A. Z. Fernandis, et al. (2004). "Slit protein-mediated inhibition of CXCR4-induced chemotactic and chemoinvasive signaling pathways in breast cancer cells." *J Biol Chem* 279(10): 9115-24.

Prasad, A., Z. Qamri, et al. (2007). "Slit-2/Robo-1 modulates the CXCL12/CXCR4-induced chemotaxis of T cells." *J Leukoc Biol* 82(3): 465-76.

Prevost, N., D. S. Woulfe, et al. (2005). "Eph kinases and ephrins support thrombus growth and stability by regulating integrin outside-in signaling in platelets." *Proc Natl Acad Sci USA* 102(28): 9820-5.

Robinson, L. A., Tu, L., Steeber, D. A., Preis, O., Platt, J. L., and Tedder, T. F. 1998. The role of adhesion molecules in human leukocyte attachment to porcine vascular endothelium: implications for xenotransplantation." *J Immunol* 161:6931-6938.

Ronca, F., Andersen, J. S., Paech, V., and Margolis, R. U. 2001. Characterization of Slit protein interactions with glypican-1. *J Biol Chem* 276:29141-29147.

Ruggeri, Z. M. (2002). "Platelets in atherothrombosis." *Nat Med* 8(11): 1227-34.

Saederup, N., L. Chan, et al. (2008). "Fractalkine deficiency markedly reduces macrophage accumulation and atherosclerotic lesion formation in CCR2−/− mice: evidence for independent chemokine functions in atherogenesis." *Circulation* 117(13): 1642-8.

Salmela, K., L. Wramner, et al. (1999). "A randomized multicenter trial of the anti-ICAM-1 monoclonal antibody (enlimomab) for the prevention of acute rejection and delayed onset of graft function in cadaveric renal transplantation: a report of the European Anti-ICAM-1 Renal Transplant Study Group." *Transplantation* 67(5): 729-36.

Siljander, P. R., I. C. Munnix, et al. (2004). "Platelet receptor interplay regulates collagen-induced thrombus formation in flowing human blood." *Blood* 103(4): 1333-41.

Singbartl, K., S. A. Green, et al. (2000). "Blocking P-selectin protects from ischemia/reperfusion-induced acute renal failure." *FASEB Journal* 14(1): 48-54.

Star, R. A. (1998). "Treatment of acute renal failure." *Kidney Int* 54(6): 1817-31.

Stojanovic, A., J. A. Marjanovic, et al. (2006). "A phosphoinositide 3-kinase-AKT-nitric oxide-cGMP signaling pathway in stimulating platelet secretion and aggregation." *J Biol Chem* 281(24): 16333-9.

Sullivan, T. P., Eaglstein, W. H., Davis, S. C., and Mertz, P. 2001. The pig as a model for human wound healing. *Wound Repair Regen* 9:66-76.

Sun, C. X., M. A. Magalhaes, et al. (2007). "Rac1 and Rac2 differentially regulate actin free barbed end formation downstream of the fMLP receptor." *J Cell Biol* 179(2): 239-45.

Thadhani, R., M. Pascual, et al. (1996). "Acute renal failure." *New End J Med* 334(22): 1448-60.

Tole, S., I. M. Mukovozov, et al. (2009). "The axonal repellent, Slit2, inhibits directional migration of circulating neutrophils." *J Leukoc Biol* 86(6): 1403-15.

Trumel, C., B. Payrastre, et al. (1999). "A key role of adenosine diphosphate in the irreversible platelet aggregation induced by the PAR1-activating peptide through the late activation of phosphoinositide 3-kinase." *Blood* 94(12): 4156-65.

von Hundelshausen, P. and C. Weber (2007). "Platelets as Immune Cells: Bridging Inflammation and Cardiovascular Disease." *Circ Res* 100(1): 27-40.

Werbowetski-Ogilvie, T. E., M. Seyed Sadr, et al. (2006). "Inhibition of medulloblastoma cell invasion by Slit." *Oncogene* 25(37): 5103-12.

Wong, K., X. R. Ren, et al. (2001). "Signal transduction in neuronal migration: roles of GTPase activating proteins and the small GTPase Cdc42 in the Slit-Robo pathway." *Cell* 107(2): 209-21.

Woulfe, D., H. Jiang, et al. (2004). "Defects in secretion, aggregation, and thrombus formation in platelets from mice lacking Akt2." *J Clin Invest* 113(3): 441-50.

Wu, J. Y., L. Feng, et al. (2001). "The neuronal repellent Slit inhibits leukocyte chemotaxis induced by chemotactic factors." *Nature* 410(6831): 948-52.

Xue, J. L., F. Daniels, et al. (2006). "Incidence and mortality of acute renal failure in Medicare beneficiaries, 1992 to 2001." *J Am Soc Nephrol* 17(4): 1135-42.

Yan, M., C. Di Clano-Oliveira, et al. (2007). "Coronin function is required for chemotaxis and phagocytosis in human neutrophils." *J Immunol* 178(9): 5769-78.

Yang, L., J. R. Kowalski, et al. (2006). "Endothelial cell cortactin phosphorylation by Src contributes to polymorphonuclear leukocyte transmigration in vitro." *Circ Res* 98(3): 394-402.

Yiin, J. J., B. Hu, et al. (2009). "Slit2 inhibits glioma cell invasion in the brain by suppression of Cdc42 activity." *Neuro Oncol.*

Yin, H., A. Stojanovic, et al. (2008). "The role of Akt in the signaling pathway of the glycoprotein Ib-IX induced platelet activation." *Blood* 111(2): 658-665.

You, X., Mungrue, I., Kalair, W., Afroze, T., Ravi, B., Sadi, A., Gros, R., and Husain, M. 2003. Conditional expression of a dominant-negative c-Myb in vascular smooth muscle cells inhibits arterial remodeling after injury. *Circ Res* 92:314-321.

Zaidi, S., You, X., Ciura, S., O'Blenes, S., Husain, M., and Rabinovich, M. 2000. Suppressed smooth muscle proliferation and inflammatory cell invasion after arterial injury in elafin overexpressing mice. *J Clin Invest* 105:1687-1695.

Zarbock, A. and K. Ley (2009). "Neutrophil adhesion and activation under flow." *Microcirculation* 16(1): 31-42.

Zhang, B., U. M. Dietrich, et al. (2009). "Repulsive axon guidance molecule Slit3 is a novel angiogenic factor." *Blood* 114(19): 4300-9.

Zhu, L., W. Bergmeier, et al. (2007). "Regulated surface expression and shedding support a dual role for semaphorin 4D in platelet responses to vascular injury." *Proc Natl Acad Sci USA* 104(5): 1621-6.

Zhu, L., T. J. Stalker, et al. (2009). "Disruption of SEMA4D ameliorates platelet hypersensitivity in dyslipidemia and confers protection against the development of atherosclerosis." *Arterioscler Thromb Vasc Biol* 29(7): 1039-45.

The invention claimed is:

1. A method of inhibiting platelet coagulation comprising administering a Slit protein or a functional variant thereof an animal in need thereof; wherein the functional variant has 90% identity to the Slit protein or is a conservative amino acid substituted variant of the Slit protein; wherein the Slit protein or functional variant thereof inhibits platelet adhesion, spreading and/or clotting.

2. The method of claim 1, for treating a subject with a platelet-coagulation related condition or disease.

3. The method of claim 2, wherein the platelet-coagulation related condition or disease is thrombosis, clot formation, atherosclerosis, cardiovascular disease, pulmonary embolism or hypercoagulable state.

4. The method of claim 1 for treating a subject at risk of excessive platelet coagulation.

5. The method of claim 4, for treating a subject at risk of a narrowing artery comprising instilling the Slit protein or nucleic acid during balloon angioplasty.

6. The method of claim 1, wherein the Slit protein or functional variant thereof is Slit1, Slit2 or Slit3.

7. The method of claim 6, wherein the Slit protein or functional variant thereof is Slit2.

8. The method of claim 1, wherein the Slit protein or functional variant thereof is Slit2-N.

9. The method of claim 1, comprising administering Slit1, Slit2 or Slit3 protein.

10. The method of claim 1, comprising administering Slit2 or Slit2-N.

* * * * *

UNITED STATES PATENT AND TRADEMARK OFFICE
CERTIFICATE OF CORRECTION

PATENT NO. : 8,399,404 B2
APPLICATION NO. : 13/100678
DATED : March 19, 2013
INVENTOR(S) : Lisa Annette Robinson It is certified that error appears in the above-identified patent and that said Letters Patent is hereby corrected as shown below:

In the Claims

Claim 1 at column 45, line 62, "thereof an" should read "thereof to an".

Signed and Sealed this
Twenty-second Day of October, 2013

Teresa Stanek Rea
*Deputy Director of the United States Patent and Trademark Office*